US006911341B2

(12) United States Patent
Bestetti et al.

(10) Patent No.: US 6,911,341 B2
(45) Date of Patent: Jun. 28, 2005

(54) VECTORS, HOST CELLS, AND METHODS FOR PRODUCTION OF URIDINE PHOSPHORYLASE AND PURINE NUCLEOSIDE PHOSPHORYLASE

(75) Inventors: Giuseppina Bestetti, Agrate Brianza (IT); Simona Cali' , Abbiategrasso (IT); Daniela Ghisotti, Milan (IT); Gaetano Orsini, Varese (IT); Giancarlo Tonon, Milan (IT); Gabriele Zuffi, Novata Milanese (IT)

(73) Assignee: Keryos SpA, Milan (IT)

(*) Notice: Subject to any disclaimer, the term of this patent is extended or adjusted under 35 U.S.C. 154(b) by 322 days.

(21) Appl. No.: 09/891,865

(22) Filed: Jun. 25, 2001

(65) Prior Publication Data

US 2003/0059870 A1 Mar. 27, 2003

Related U.S. Application Data

(63) Continuation of application No. PCT/EP99/10416, filed on Dec. 23, 1999.

(30) Foreign Application Priority Data

Dec. 23, 1998 (IT) ........................................ MI98A2792

(51) Int. Cl.$^7$ .......................... C12N 15/00; C07H 21/04

(52) U.S. Cl. .................. 435/320.1; 536/23.2; 536/23.4; 536/23.7

(58) Field of Search ........................... 435/320.1, 252.3, 435/193; 536/23.2, 23.4, 23.7

(56) References Cited

U.S. PATENT DOCUMENTS

| | | | | |
|---|---|---|---|---|
| 4,347,315 A | * 8/1982 | Krenitsky et al. | ............ | 435/87 |
| 4,835,104 A | 5/1989 | Yokozeki et al. | ............ | 435/87 |
| 5,563,049 A | 10/1996 | Kojima et al. | ................ | 435/88 |
| 6,197,552 B1 | 3/2001 | Yokozeki et al. | ............. | 435/88 |

FOREIGN PATENT DOCUMENTS

| | | |
|---|---|---|
| EP | 0002192 | 6/1979 |
| EP | 0038568 | 10/1981 |
| JP | 06-253854 | 9/1994 |
| JP | 6-253854 | 9/1994 |

OTHER PUBLICATIONS

Bulow et al. (1991) Trends Biotech 9:226–231.*

Novagen 1997 Catalog, pp. 42–43 and 156.*

Sambrook et al. "Molecular Cloning, A Laboratory Manual, Second Edition", Cold Spring Harbor Press, 1989, pp. 1.5–1.6.*

Ausubel et al. Current Protocols in Molecular Biology, John Wiley and Sons, Inc., 1995, p. 16.1.1.*

Database GenBank Accession No. L08752, Apr. 1993.*

Branden et al. "Introduction to Protein Structure", Garland Publishing Inc., New York, 1991, p. 247.*

Witkowski et al. (1999) Biochemistry 38:11643–11650.*

Hershfield, M.S. et al.; "Use of site–directed mutagenesis to enhance the epitope–shielding effect of covalent modification of proteins with polyethylene glycol"; Proceedings of the Ntional Academy of Science of USA, vol. 88, 1991, pps. 7185–7189.

Brykun, I.A. et al.; "Cloning the *Escherichia coli* uridine phosphorylase gene udp and its expression in the recombinant plasmids"; Genetika, vol. XXV, No. 10, 1989, pps. 1717–1724, (russian language).

Walton, L. et al.; "Nucleotide sequence of the *Escherichia coli* uridine phosphorylase (udp) gene"; Nucleic Acids Research, vol. 17, No. 16, 1989, p. 6741.

Takehara, M. et al.; "Molecular cloning and nucleotide sequence of purine nucleoside phosphorylase and uridine phosphorylase genes from *Klebsiella* sp.", Bioscience, Biotechnology and Biochemistry, vol. 59, No. 10, 1995, pps. 1987–1990.

Krenitsky, T.A. et al.; "Purine nucleoside synthesis, an efficient method employing nucleoside phosphorylases", Biochemistry, vol. 20, 1981, pps. 3615–3621.

Mikhailopulo, I.A. et al.; "1–deaza and 3–deazapurines in the reaction of microbiological transglycosylation", Biotechnology Letters, vol. 14, No. 10, Oct. 1992, pps. 885–890.

Krenitsky, T.A. et al.; "An enzymic synthesis of purine D–arabinonucleosides", Carbohydrate Research, vol. 97, 1981, pps. 139–146.

Mikhailopuolo, A.I. et al.; "Benzimidazoles in the reaction of enzymatic transglycosylation", Nucleosides & Nucleotides, vol. 14, No. 3–5, 1995, pps. 477–480.

Mayer, M.P.; "A new set of useful cloning and expression vectors derived from pBlueScript", Gene, NL, Elsevier Biomedical Press Amsterdam, vol. 163, No. 1, Sep. 22, 1995, pps. 41–46.

Zintchenko, A.I. et al.; "Substrate specificity of uridine and purine nucleoside phosphorylases of the wohole cells of *Escherichia coli*", Nucleic Acids Research Symposium Series, vol. 18, 1987, pps. 137–140.

PCT International Search Report (PCT/ISA/210) 9 pages from PCT/EP 99/10416.

PCT Partial International Search Results Communication (PCT/ISA/206) 4 pages from PCT/EP/99/0416.

* cited by examiner

*Primary Examiner*—David J. Steadman
(74) *Attorney, Agent, or Firm*—Darby & Darby

(57) ABSTRACT

Strains of genetically modified prokaryotic micro-organisms capable of expressing polypeptides having the enzyme activity of the enzymes uridine posphorylase (UdP) and purine nucleoside phosphorylase (PNP) are described; the strains in question can be used, both in the form of whole cells and in the form of crude or purified extracts, to catalyse transglycosylation reactions between a donor nucleoside and an acceptor base with particularly high yields. The associated plasmid vectors are also described.

7 Claims, 6 Drawing Sheets

FIG. 2A

```
RBS                                 EcoRI               KpnI                                  SalI                SphI     HindIII
AGGAAAACAGCT ATG ACC ATG ATT ACG AAT TCG AGC TCG GTA CCC GGG GAT CCT CTA GAG TCG ACC TGC AGG CAT GCA AGC TTG
                 thr met ile thr asn ser ser ser val pro gly asp pro leu glu ser thr cys arg his ala ser leu
```

FIG. 2B

```
RBS                                 EcoRI                                                              SalI
AGGAAAACAGCT ATG ACC ATG ATT ACG AAT TCT TCC ATG GCT ACC CCA..........TGG GCG TAA AGAGTAAGTCGACCTGC....
                 thr met ile thr asn ser ser met ala thr pro..........trp ala stop
```

FIG. 2C

```
RBS                                                 KpnI                                                       SalI
AGGAAAACAGCT ATG ACC ATG ATT ACG AAT TCG AGC TCG GTA CCA TCC ATG TCC .......CTG CTG TAA TTCTCTTGTCGCAATG....
                 thr met ile thr asn ser ser ser val pro ser met ser........leu leu stop
```

FIG. 2D

```
SalI/NheI  RBS EcoRI                                                  SalI          SphI
GTCGACTAGCAGGAGGAATTCTTCC ATG GCT ACC CCA......... TGG GCG TAA AGAGTAAGTCGACCTGCAGGCATGCAA
                          met ala thr pro......... trp ala stop
```

VECTORS, HOST CELLS, AND METHODS FOR PRODUCTION OF URIDINE PHOSPHORYLASE AND PURINE NUCLEOSIDE PHOSPHORYLASE

This is a continuation of international application Serial No. PCT/EP99/10416, filed 23 Dec. 1999, the entire disclosure of which is hereby incorporated by reference.

The present invention relates to novel genetically modified bacterial strains capable of expressing polypeptides having the enzyme activity of the enzymes UdP and PNP; the strains in question can be used to catalyse transglycosylation reactions between a donor nucleoside and an acceptor base.

Natural nucleosides or the modified analogues thereof have important applications, both directly and as intermediates, in the field of drugs having an anti-viral and anti-tumour action, as well as in the preparation of oligonucleotides for therapeutic and diagnostic use.

Nucleosides can be prepared using methods of chemical synthesis which normally require a large number of steps processes for the protection and deprotection of labile groups and the use of reagents and operating conditions which, on an industrial level, may be both difficult to apply and economically disadvantageous. In addition, those reactions do not generally have high overall yields owing also to the formation of mixtures of stereo- and regio-isomers from which the compound of interest has to be separated.

An alternative approach to the preparation of nucleosides and modified analogues thereof is based on interconversion between a sugar-donating nucleoside and an acceptor base by means of enzymes which catalyse the general reversible reactions (Hutchinson, Trends Biotechnol. 8, 348–3 53, 1990) given below in scheme 1:

Scheme 1

Reaction 1 pyrimidine-β-(deoxy)ribonucleoside + Pi pyrimidine base + α-(deoxy)ribose-1-phosphate Reaction 2 purine base + α-(deoxy)ribose-1-phosphate purine-β-(deoxy)ribonucleoside + Pi where Pi=organic phosphate.

Reaction 1 is catalysed by the enzyme uridine phosphorylase or UdP (E.C.2.4.2.3.) while reaction 2 is catalysed by the enzyme purine nucleoside phosphorylase or PNP (E.C.2.4.2.1.).

The UdP and PNP enzymes can be used individually to catalyse transglycosylation reactions between a donor pyrimidine nucleoside and an acceptor pyrimidine base or between a donor purine nucleoside and an acceptor purine base, respectively. In addition, when the two enzymes are used in combination, it is possible to transfer the sugar from a donor pyrimidine nucleoside to a purine or pyrimidine acceptor base as well as from a donor purine nucleoside to a pyrimidine or purine acceptor base, depending on the starting materials used. In each case the phosphorolysis reactions involve a configuration change at position 1 of the sugar to give an α-sugar-1-phosphate which constitutes the intermediate substrate of the transglycosylation reactions and which is subsequently transferred to the acceptor base, with restoration of the original β configuration.

Those enzyme reactions can advantageously be carried out starting from a mixture of a donor nucleoside and an acceptor base in the simultaneous presence of the two enzymes and without isolating the intermediate sugar phosphate or in two steps comprising phosphorolysis with formation of the intermediate sugar phosphate, its isolation and subsequent condensation with the acceptor base.

With regard to chemical synthesis, an important advantage of transglycosylation reactions catalysed by phosphorylases is the maintenance of stereo-selectivity and regio-selectivity, as a result of which the end product retains the β configuration of natural nucleosides.

The UdP and PNP enzymes which participate physiologically in the catabolism and interconversion reactions of nucleosides are the product, respectively, of the udp and deoD genes, occurring widely in nature, and have been identified and studied in both prokaryotic and eukaryotic organisms (Parks and Agarwal Enzymes 7, 3rd ed., 483–514, Academic Press, New York; Munch-Petersen, Metabolism of nucleotides, nucleosides and nucleobases in micro-organisms, Academic Press, London, 1982).

From the point of view of use as catalysts for the synthesis of nucleosides and modified analogues thereof the enzymes of prokaryotic organisms are generally preferred because they have a lower substrate specificity and they can catalyse transglycosylation reactions starting also from donor nucleosides containing modified sugars and from acceptor bases comprising both purine or pyrimidine structures and various nitrogen-containing heterocyclic systems (Stoeclder et al., Biochemistry 19, 102–107, 1980, Browska et al., Z. Naturforsch., 45, 59–70, 1990).

The transglycosylation reactions can be carried out using purified or partially purified enzyme preparations (Krenitsky et al., Biochemistry 20, 3615–3621, 1981; EP-002192) or, alternatively, using the whole bacterial cells of microorganisms selected because they contain the necessary enzymes (Utagawa et al., Agric. Biol. Chem. 49, 3239–3246,1985) or whole cells cultivated in the presence of inducers of the production of those enzymes (Doskocil et al., Collect. Czech. Chem. Commun. 42, 370–383, 1977).

For biocatalysis reactions carried out at a preparative level, the use of whole cells both obviates the need to extract and purify the enzymes and enables the cells to be recovered easily at the end of the reaction, for example by centrifugation or ultrafiltration, and to be re-used for other, subsequent, reaction cycles; alternatively, it is possible to use the UdP and PNP enzymes extracted from the cells in the form of a crude or purified soluble cell fraction. Both UdP and PNP are enzymes characterised by good thermal stability which enables the transglycosylation reactions to be carried out at temperatures of up to approximately 60° C. without significant activity losses and enables the recovered enzyme preparations to be re-used. Approaches have also been described where the recycling of cells used as catalysts was carried out by micro-encapsulation in both hydrophilic gels (Votruba et al., Collect. Czech. Chem. Commun. 59, 2303–2330, 1994) and hydrophobic gels (Yokozeki et al., Eur. J. Appl. Microbiol. Biotechnol., 14, 225–231, 1982).

The main limitations of the methods known hitherto for the preparation of natural nucleosides and modified analogues thereof by transglycosylation reactions using bacterial cells reside in the low enzyme concentration obtainable, even after induction, and in the impossibility of using optimised amounts of the two enzyme activities required to catalyse the transfer of the sugar from a donor nucleoside to an acceptor base.

Both in the case of selection of wild-type bacterial strains and in the case of cultivation of strains under induction conditions, cells are obtained that contain levels of UdP and PNP which are generally not higher than 10 times the base levels (F. Ling et al., Process Biochem. 29,355–361,1994) and which are in non-predeterminable ratios. Furthermore, because one of the two enzymes (generally PNP) is present in the induced cells in lower amounts, it is usually necessary to use an excess of cells such as to ensure the presence of the limiting enzyme at levels compatible with acceptable overall kinetics of the interconversion reaction. From an operating point of view, this means that a significant portion of the reaction mixture is constituted by the cell suspension, with consequent restriction of the volume that can be used to solubilise the substrates and, finally, with a lower volumetric yield of end product.

The present invention therefore relates to the construction of genetically modified bacterial strains capable of solving the problems described above and, in particular, of catalysing transglycosylation reactions between a donor nucleoside and an acceptor base with high yields which are foreseeable and, above all, reproducible on an industrial scale and with particularly rapid enzyme kinetics.

The literature has described the cloning and expression of some recombinant phosphorylases, such as, for example, human UdP (Watanabe and Uchida, Biochem. Biophys. Res. Commun. 216, 265–272, 1996), murine UdP (Watanabe et al., J. Biol. Chem. 270, 12191–12196, 1995), of *Escherichia coli* (Mikhailov et al, Biochem. Internat. 26, 607–615, 1992) and human PNP (Erion et al., Biochemistry 36, 11725–11734, 1997), of the thermophilic micro-organism *Bacillis stearothernophilus* (Hamamoto et al., Biosci. Biotech. Biochem. 61, 272–275, 1997; Hamamoto et al., Biosci. Biotech. Biochem. 61, 27&280, 1997) in addition to UdP and PNP from *Klebsiella* sp (Takehara et al., Biosci. Biotech. Biochem. 59, 1987–1990, 1995). In particular, Japanese patent application JP-06-253854 describes the expression in *E. coli* of bacterial plasmids containing the gene sequences of the enzymes purine and/or pyriridine nucleoside phosphorylase derived solely from thermophilic bacteria, that is bacteria having optimum growth at temperatures of from 50 to 60° C., such as, for example, *Bacillus steardermophilus.*

Novel genetically modified bacterial strains that contain the genes coding for polypeptides having the enzyme activity of the enzymes uridine phosphorylase (UdP) and/or purine nucleoside phosphorylase (PNP), both separately and together, have now been found and constitute part of the subject matter of the present invention. The cultivation of these novel strains enables both high levels of biomass and high levels of expression of the recombinant enzymes to be obtained; the novel strains according to the present invention can also be used either directly or after extraction of the soluble cell fraction as catalysts for the production of natural nucleosides and modified analogues thereof with substantial improvements in the process in comparison with the prior art.

In contrast to what has been described in JP-06-253854, the plasmid vectors according to the present invention can be obtained by cloning both separately and simultaneously the udp and deoD genes of mesophilic bacteria, that is bacteria having optimum growth at temperatures of from 30 to 37° C. such as, for example, *E. coli*. To be more precise, the gene sequences preferably used for the purposes of the present invention are the *E. coli* sequences that encode the udp and deoD genes and that are deposited in the EMBL data bank with the accession numbers X15689 (udp) and M60917 (deoD); however, it is also possible to use other widely available sequences, such as, for example, AC CG01747 (udp) and AC CG00327 (deoD).

The expression plasmid vectors which may be used for the purposes of the invention and which form part of the subject matter thereof are therefore characterised in that they comprise:

a) at least one gene sequence of a mesophilic bacterium coding for a polypeptide having enzyme UdP and/or enzyme PNP activity; and b) at least one gene sequence coding for antibiotic resistance.

The at least one sequence coding for antibiotic resistance is preferably a sequence coding for tetracycline, kanamycin and/or ampicillin resistance. The plasmid vectors of the present invention can be obtained by cloning either the sequence coding for udp and/or the sequence coding for deoD or, optionally, the sequence coding for tetracycline and/or kanamycin resistance into the plasmid pUC18 (Yanish and Perron, Gene 33, 103–119, 1985; EMBL accession number L08752) which already contains the ampicillin resistance gene.

The relative position of the sequences coding for udp and deoD is not, however, relevant for the purposes of the invention: that is to say, the sequence coding for udp can be positioned either downstream or upstream of the sequence coding for deoD. Furthermore, and as it will be appreciated from the Examples which follow, the gene sequences coding for udp and deoD may also be fused together so to express novel fusion proteins wherein the enzymes UdP and PNP are either covalently bonded together (UdP-PNP) or, alternatively, the novel fusion protein may have the formula UdP-(L)-PNP wherein L is a polipeptide linker of more than one aminoacidic unit. In these novel fusion proteins, the relative position of the two components is not however relevant for the purposes of the invention: that is to say, the PNP component can be either at the $NH_2$-terminal or at the COOH-terminal position of the fused proteins. The novel proteins thus obtainable, which are a further object of the present invention, are characterized by possessing a bifunctional activity as they are able to perform both the activity of the enzyme UdP and that of the enzyme PNP.

An additional object of the present invention is then represented by the method for producing the above mentioned fusion proteins, said method comprising:

(a) producing a plasmid expression vector as above indicated;

(b) transforming a host bacteria cell with said expression vector; and (c) isolating and purifying the fusion protein from the transformed bacteria cell.

BRIEF DESCRIPTION OF THE DRAWINGS

FIGS. 2A to 2D. 5' and 3' sequences of upd and deoD genes cloned in plasmid pUC18. Res ction sites of different constructs are underlined. The bases of nucleotide sequences of upd and d oD genes and the amino acid residues of PNP and UdP proteins are reported in italics. (A) Plasmid pUC18: 5' sequence of lacZ gene. (B) Plasmid pGM678 and pGM707: sequence of lacZ-deoD fused gene. (C) plasmid pGM679 and pGM708: sequence of lacZ-upd fused genes. (D) Plasmid pGM712 and pGM716: 5' and 3' sequence of deoD gene.

The methods for transforming a host bacteria cell with an expression vector and for isolating and purifying the expressed peptide are well known to any skilled in this art and are for example disclosed in Swartz J R, *Escherichia coli* recombinant DNA technology, and in Neidahrt F C et al. (edts), *Escherichia coli* and *Salmonella typhimurium*: Cellular and molecular biology, $2^{nd}$ edition, pp 1693–1711, ASM, Washington, herein incorporated as a reference.

The hosts preferably used for the expression of the recombinant enzymes according to the present invention are bacterial cells of *Escherichia coli*; the strains K12 (preferably DH5α or MG1655) and/or the B strains are of particular interest. Alternatively, however, it is possible to use cells of other prokaryotic micro-organisms which are acceptable for industrial use because they are not dangerous to operators and the environment and they can be readily cultivated to obtain high levels of biomass.

As will also be seen from the Examples, the presence of a bacterial promoter, and in particular of the Sac promoter, is not an essential element for the purposes of the present invention because it has been found that cell growth and the expression of polypeptides do not depend on the presence of an inducer (IPTG). For ease of performance, the gene sequence encoding a polypeptide having enzyme UdP activity and/or enzyme PNP activity is cloned into the plasmid pUC18 in the reading frame relative to the lac promoter.

Finally, the sequence coding for tetracycline resistance is preferably the Tet gene of pBR322; the sequence coding for kanamycin resistance is the kan gene of pET29c.

Figure 1:
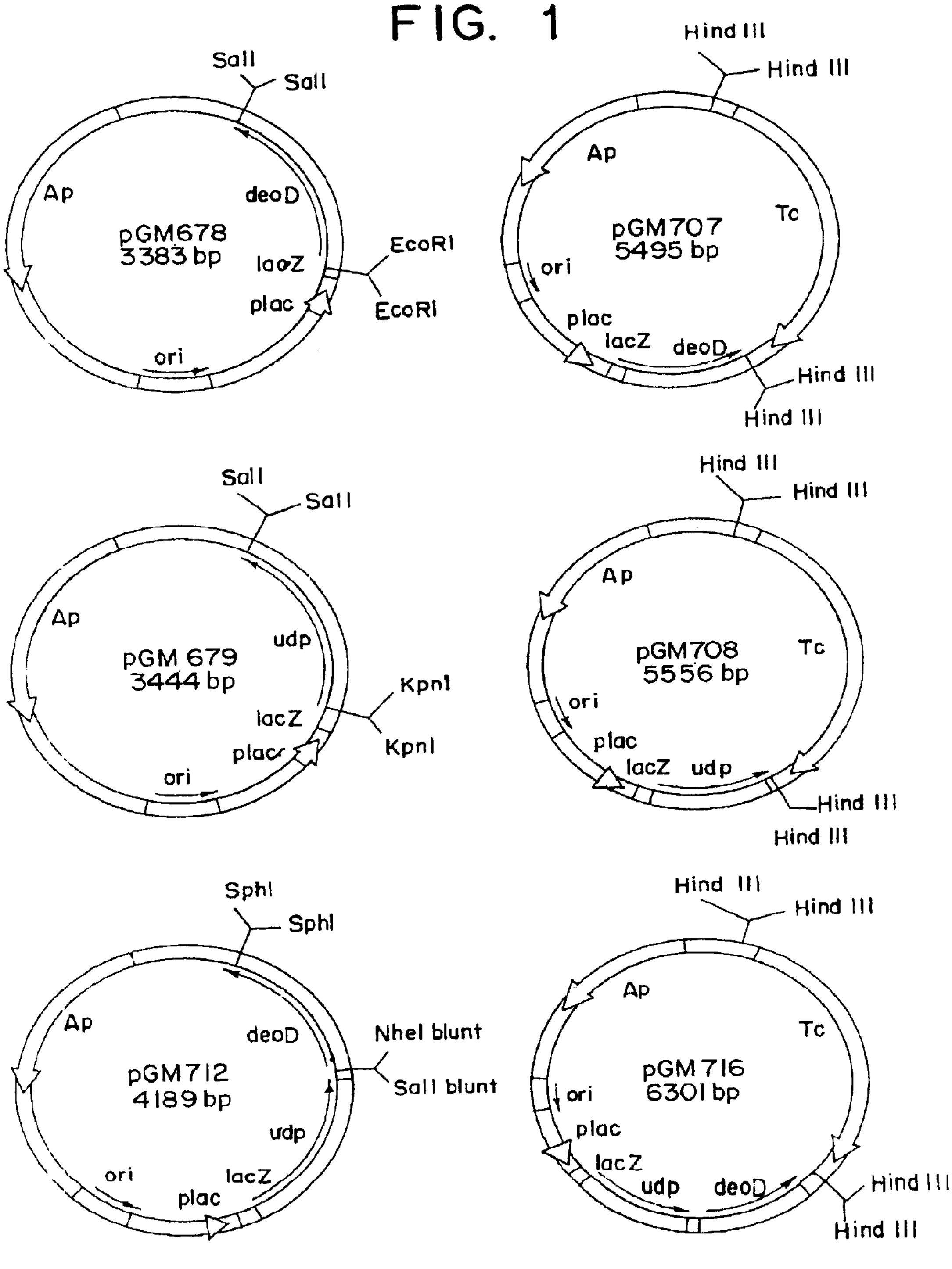
FIG. 1. Cloning vectors for the expression of UdP and PNP enzymes.
Figure 3A:
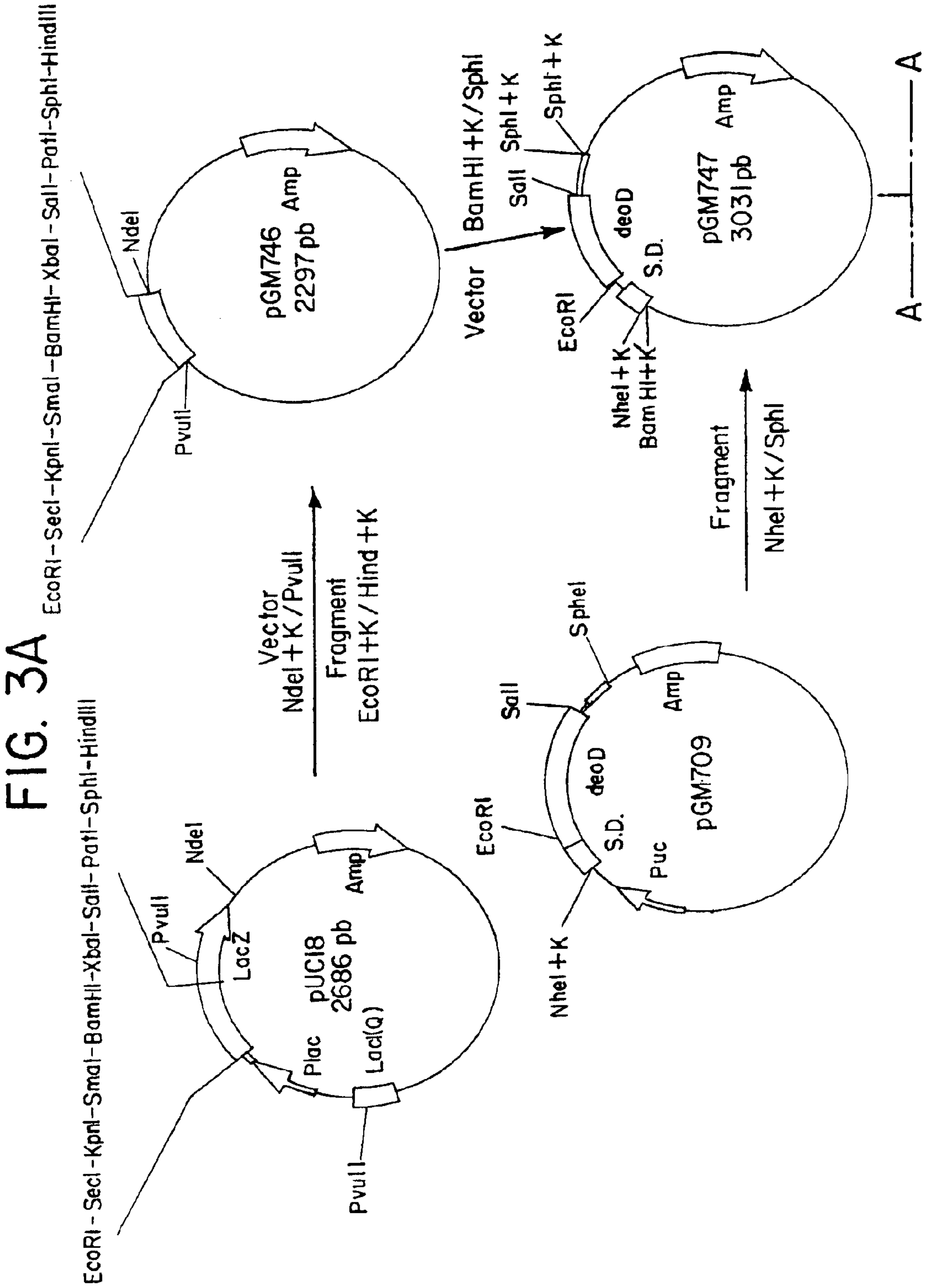
FIGS. 3A and 3B. Construction of cloning vectors for the expression of UdP and PNP enzymes.
Figure 3B:
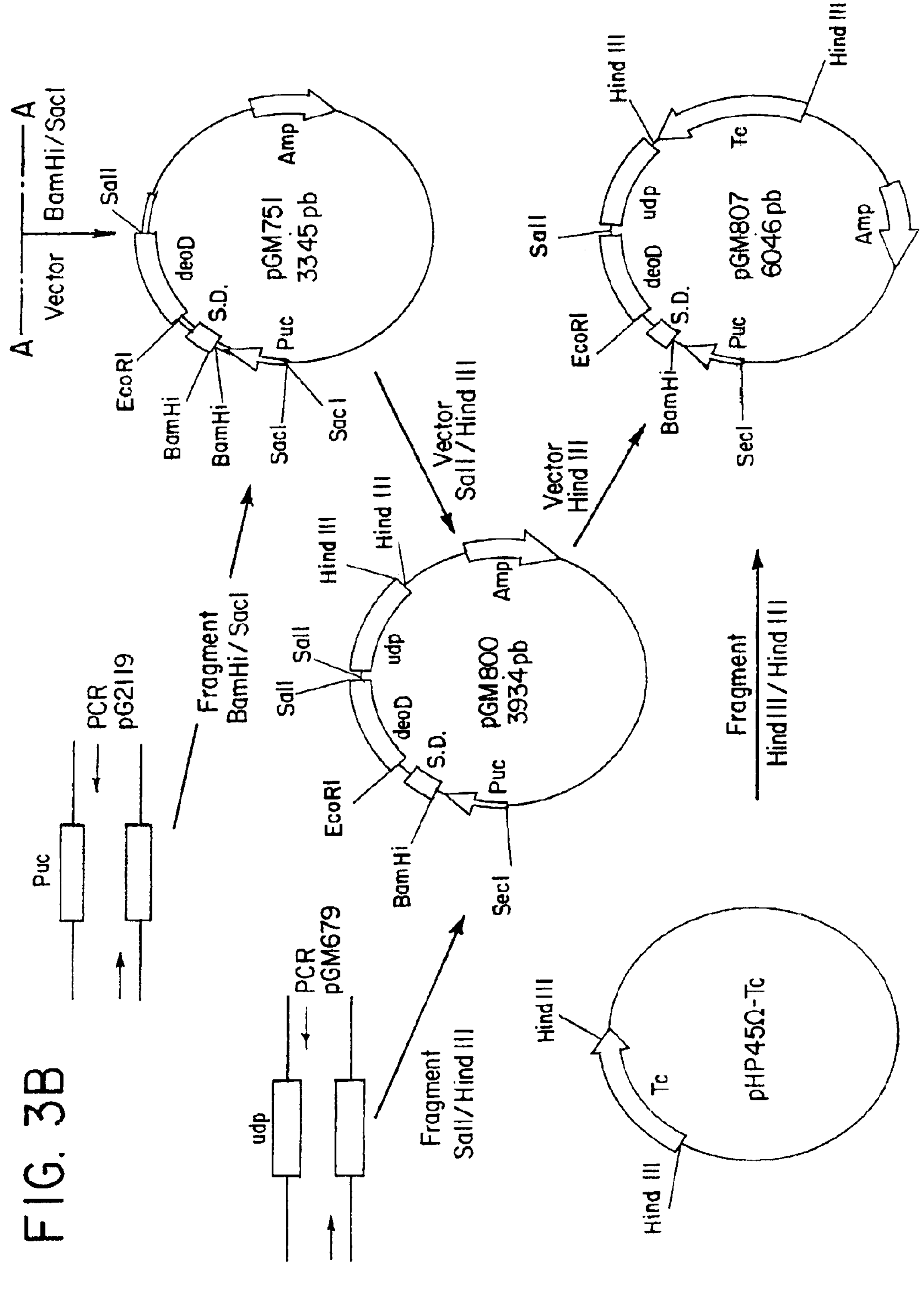
Figure 4:
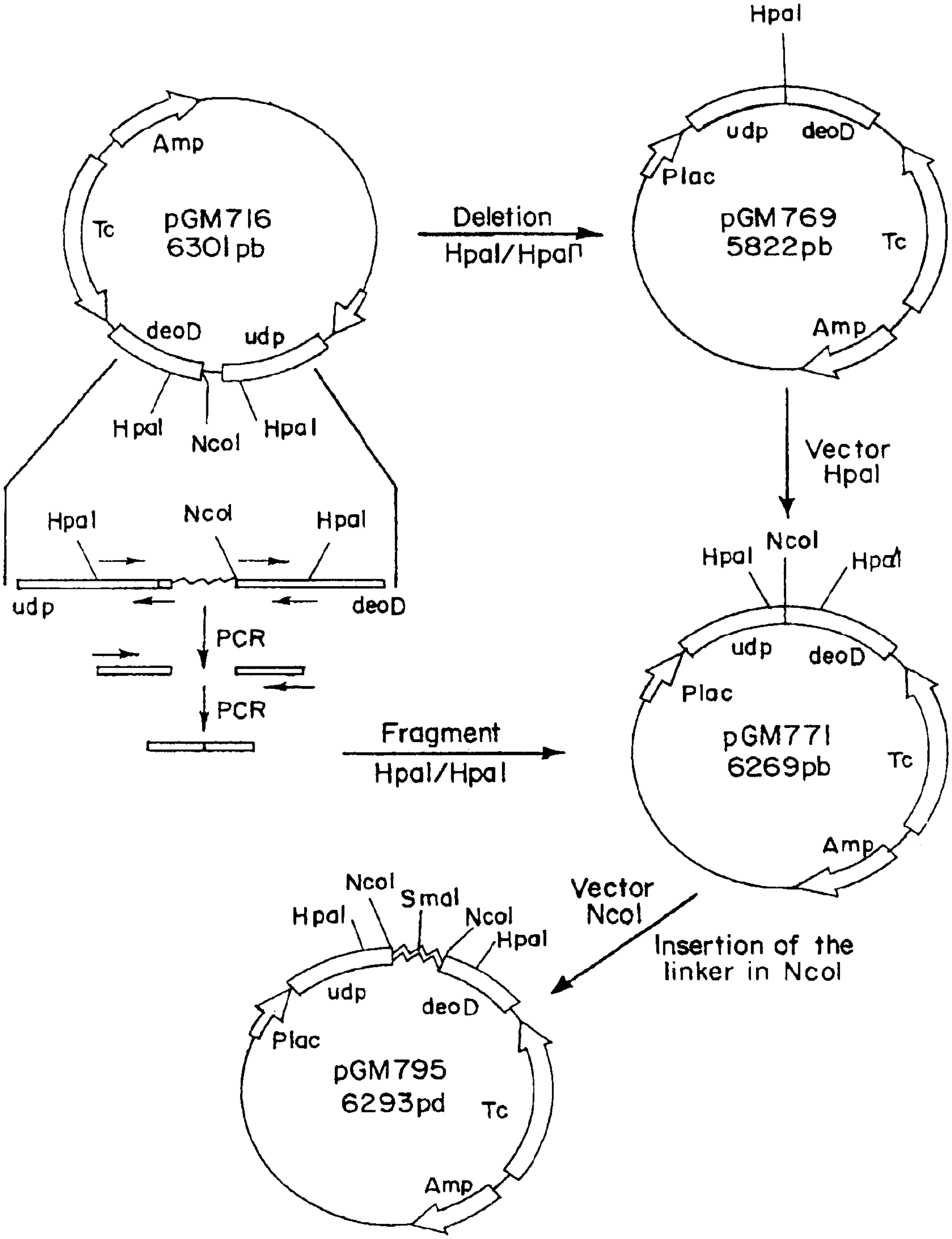
FIG. 4. Construction of cloning vectors for the expression of UdP-(L)-PNP enzymes.

Thus, in accordance with well-known methods which will become clear from the Examples, the following plasmids, which are represented in FIGS. 1, 3 and 4, were constructed:

pGM679: udp gene cloned into plasmid pUC18 (SEQ ID NO 1). In the sequence numbering, coordinate 1 of pGM679 coincides with that of the pUC18 vector sequence; from nucleotide 1 to 242: pUC18 sequence; from 243 to 1021: *E. coli* udp gene sequence; from 1022 to 3444: pUC18 sequence.

pGM708: udp gene cloned into plasmid pUC18 together with the tetracycline resistance gene (SEQ ID NO 2). In the sequence numbering, coordinate 1 of pGM708 coincides with that of the pUC18 vector sequence; from nucleotide 1 to 242: pUC18 sequence; from 243 to 1021: *E. coli* udp gene sequence; from 1022 to 1039: pUC18 sequence; from 1040 to 1482: pHP45Ω sequence; from 1483 to 2883: pBR322 Tet gene sequence; from 2884 to 3151: pBP45Ω sequence; from 3152 to 5556: pUC18 sequence.

pGM678: deoD gene cloned into plasmid pUC18 (SEQ ID NO 3). In the sequence numbering, coordinate 1 of pGM678 coincides with that of the pUC18 vector sequence; from nucleotide 1 to 230: pUC18 sequence; from 231 to 960: *E. coli* deoD gene sequence; from 961 to 3383: pUC18 sequence.

pGM707: deoD gene cloned into plasmid pUC18 together with the tetracycline resistance gene (SEQ ID NO 4). In the sequence numbering, coordinate 1 of pGM707 coincides with that of the pUC18 vector sequence; from nucleotide 1 to 230: pUC18 sequence; from 231 to 960: *E. coli* deoD gene sequence; from 961 to 978: pUC18 sequence; from 979 to 1422: pHP45Ω sequence; from 1423 to 2822: pBR322 Tet gene sequence; from 2823 to 3090: pHP45Ω sequence; from 3091 to 5495: pUC18 sequence.

pGM712: udp and deoD genes cloned into plasmid pUC18 (SEQ ID NO 5). In the sequence numbering, coordinate 1 of pGM712 coincides with that of the pUC18 vector sequence; from nucleotide 1 to 242: pUC18 sequence; from 243 to 1021: *E. coli* udp gene sequence; from 1022 to 1025: pUC18 sequence; from 1026 to 1036: pBAD24 sequence; from 1037 to 1766: *E. coli* deoD gene sequence; from 1767 to 1792: pBAD24 sequence; from 1793 to 4189: pUC18 sequence.

pGM716: udp and deoD genes cloned into plasmid pUC18 together with the tetracycline resistance gene (SEQ ID NO 6). In the sequence numbering, coordinate 1 of pGM716 coincides with that of the pUC18 vector sequence; from nucleotide 1 to 242: pUC18 sequence; from 243 to 1021: *E. coli* udp gene sequence; from 1022 to 1025: pUC18 sequence; from 1026 to 1036: pBAD24 sequence; from 1037 to 1766: *E. coli* deoD gene sequence; from 1767 to 1792: pBAD24 sequence; from 1793 to 1794: pUC18 sequence; from 1795 to 2228: pHP45Ω sequence; from 2229 to 3628: pBR322 Tet gene sequence; from 3629 to 3896: pHP45Ω sequence; from 3897 to 6301: pUC18 sequence.

pGM709: gene deoD cloned in pBAD24 (SEQ ID NO 7). In the sequence numbering, coordinate 1 of pGM709 coincides with that of the pBAD24 vector sequence; from nucleotide 1 to 1311: pBAD24 sequence; from 1312 to 2042: sequence corresponding to 230–960 of pGM678; from 2043 to 5241: pBAD24 sequence.

pGM769: pGM716 with deletion of HpaI fragment (SEQ ID NO 8). In the sequence numbering, coordinate 1 of pGM769 coincides with that of pGM716 sequence; from nucleotide 1 to 914: pGM716 sequence; from nucleotide 915 to 5822: sequence corresponding to 1394–6301 of pGM716.

pGM771: genes udp and deoD cloned in pUC18 so to create a fusion between the two proteins; the plasmid also bears the tetracycline resistance gene (SEQ ID NO 9). In the sequence numbering, coordinate 1 of pGM771 coincides with that of pGM716 sequence; from nucleotide 1 to 1011: pGM716 sequence; from nucleotide 1012 to 6269: sequence corresponding to 1044–6301 of pGM716.

pGM795: genes udp and deoD cloned in pUC18 so to create a fusion between the two proteins bonded to each other via an aminoacidic linker, the plasmid also bears the tetracycline resistance gene (SEQ ID NO 10). In the sequence numbering, coordinate 1 of pGM795 coincides with that of pGM716 sequence; from nucleotide 1 to 1011: pGM771 sequence; from 1012 to 1041: linker sequence; from 1042 to 6299: sequence corresponding to 1044–6301 of pGM716.

pGM746: cloning vector derived from pUC18 (SEQ ID NO 11). In the sequence numbering, coordinate 1 of pGM746 coincides with that of the pUC18 vector sequence; from nucleotide 1 to 54: pUC18 sequence; from 55 to 109: pUC18 polylinker sequence; from 110 to 2297 pUC18 sequence.

pGM747: deoD gene cloned into pGM746 without upstream promoter (SEQ ID NO 12). In the sequence numbering, coordinate 1 of pGM747 coincides with that of pGM746from nucleotide 1 to 79: pGM746 sequence; from 80 to 837:sequence corresponding to 1301–2058 of pGM709; from 838 to 3031: pGM746 sequence.

pGM751: deoD gene cloned downstream promoter ptac (SEQ ID NO 13). In the sequence numbering, coordinate 1 of pGM751 coincides with that of pGM747; from nucleotide 1 to 72: pGM747 sequence; from 73 to 171: ptac sequence from pGZ119; from 172 to 3128: pGM747 sequence.

pGM800: genes udp and deoD cloned downstream ptac promoter into a vector derived from pUC18 (SEQ ID NO 14). In the sequence numbering, coordinate 1 of pGM800 coincides with that of pGM751; from nucleotide 1 to 923: pGM751 sequence; from 924 to 1741: udp sequence corresponding to 203–1020 of pGM679; from 1742 to 3934: pGM751 sequence.

pGM807: genes udp and deoD cloned downstream p/ac promoter into a vector containing the tetracycline resistance gene (SEQ ID NO 15). In the sequence numbering, coordinate 1 of pGM807 coincides with that of pGM800; from nucleotide 1 to 1742: pGM800 sequence; from 1743 to 3855: Tc sequence from pHP45α; from 3856 to 6046: pGM800 sequence.

The recombinant strains so obtained express polypeptides having enzyme UdP and PNP activity in large amounts, minimising any compatibility and/or solubility problems which can be caused by the presence of heterologous proteins.

In particular, the bacterial strains called DH5α/pGM678, MG1655/pGM678, DH5α/pGM707 and MG1655/pGM707 which overexpress the enzyme PNP; the strains DH5α/pGM679, MG1655/pMG679, DH5α/pGM708 and MG1655/pGM708 which overexpress the enzyme UdP; the strains DH5α/pGM712, DH5 α/pGM716, MG1655/pGM716, DH5α/pGM800 and DH5α/pGM807 which overexpress the enzymes PNP and UdP simultaneously in the same cell; and the strains DH5α/pGM771, MG1655/pGM771, DH5α/pGM795, MG1655/pGM795, which overexpress the bifunctional fusion proteins UdP-(L)-PNP, were constructed. The efficiency of these novel strains, both as producers of the enzymes PNP and UdP and as biocatalysts for the preparation of nucleosides by bioconversion reactions, was compared with a preparation of *Enterobacter aerogenes* cells cultivated in the presence of inducers because that micro-organism, according to the data available in the literature, has hitherto been regarded as one of the best for catalysing transglycosylation reactions (Utagawa et al., Agric. Biol. Chem. 49, 1053–1058, 1985; Utagawa et al., Agric. Biol. Chem. 49, 2711–2717, 1985). The present invention relates also to the use of the novel recombinant strains in the production of polypeptides having enzyme UdP activity and/or enzyme PNP activity and/or as catalysts of transglycosylation reactions between a donor nucleoside and an acceptor base.

The enzyme activity of the recombinant strains was determined by incubating directly the cell suspension, or cell extracts obtained by mechanical and/or enzymatic lysis, in phosphate buffer with a pyrimidine nucleoside (for example uridine) to test for UdP activity or with a purine nucleoside (for example inosine) to test for PNP activity and by determining the formation of the pyrimidine base (uracil) or purine base (hypoxanthine), respectively, by reverse phase high pressure liquid chromatography (RP-HPLC), as indicated in Example 7.

Applying that test, the enzyme activities of UdP and PNP were measured in the recombinant bacterial strains to which the present invention relates and in the comparison *E. aerogenes* strain, to give the results indicated in Tables 1 and 2, which show that the recombinant strains of the present invention have enzyme activities up to approximately 10–30 times higher than that of the comparison strain cultivated under induction conditions and up to approximately 120–1000 times higher than that of the non-transformed *E. coli* host strains.

TABLE 1

Comparison of the enzyme activities of uridine phosphorylase (UdP) and purine nucleoside phosphorylase (PNP) in recombinant *E. coli* strains and in the comparison *E. aerogenes* strain.

| Novel bacterial strains according to the invention | UdP activity units/g of wet cells | PNP activity units/g of wet cells |
|---|---|---|
| wild-type MG1655 | 4.5 ± 0.2 | 3.5 ± 0.2 |
| MG1655/pGM707 | 7.5 ± 0.1 | 2400.0 ± 50.0 |
| MG1655/pGM708 | 1550.0 ± 60.0 | 6.5 ± 0.5 |
| MG1655/pGM716 | 5400.0 ± 450.0 | 850.0 ± 30.0 |
| Comparison strain | | |
| Non-induced *E. aerogenes* ATCC 13048 | 3.7 ± 0.2 | 3.0 ± 0.2 |
| Induced *E. aerogenes* ATCC 13048 | 168.3 ± 2.9 | 19.0 ± 2.2 |

TABLE 2

Comparison of the enzyme activities of uridine phosphorylase (UdP) and purine nucleoside phosphorylase (PNP) assayed into the cell extracts of the recombinant *E. coli* strains MG1655 and DH5α, in the corresponding wild-type strains and in the non-induced and induced comparison *E. aerogenes* strains.

| Novel bacterial strains according to the invention | UdP activity units/g of wet cells | PNP activity units/g of wet cells |
|---|---|---|
| non-transformed MG1655 | 9 ± 0.4 | 5 ± 0.3 |
| MG1655/pGM707 | 15 ± 0.2 | 996 ± 29 |
| MG1655/pGM708 | 3100 ± 120 | 10 ± 0.7 |
| MG1655/pGM716 | 6000 ± 160 | 643 ± 11 |
| non-transformed DH5α | 10 ± 1.0 | 3 ± 0.2 |
| DH5α/pGM707 | 14 ± 0.2 | 1000 ± 20 |
| DH5α/pGM708 | 10400 ± 750 | 4 ± 0.6 |
| DH5α/pGM716 | 6200 ± 150 | 600 ± 10 |
| *E. aerogenes* ATCC 13048 | 7.4 ± 0.4 | 4.5 ± 0.3 |
| Induced *E. aerogenes* ATCC 13048 | 335 ± 5 | 29 ± 3.3 |

The surprisingly high level of enzyme activity of these novel recombinant strains is confirmed by an indirect comparison with the strains described in JP-06-253854: the strains considered in the present invention permit enzyme activities from 340 to 1040 times (as regards the activity of UdP) and from 120 to 200 times (as regards the activity of PNP) higher than the enzyme activities of the non-transformed wild-type strains; the strains described in JP-06-253 854, on the other hand, have an enzyme activity in *E. coli* 150 and 91 times higher, respectively, than that of the corresponding wild-type strain. It is also noteworthy that the enzyme activity of the strains of the present invention was determined at 30° C. while that of the strains of JP-06-253854 was established while operating at 70° C., or at a temperature which permits markedly higher kinetics.

Figure 5:
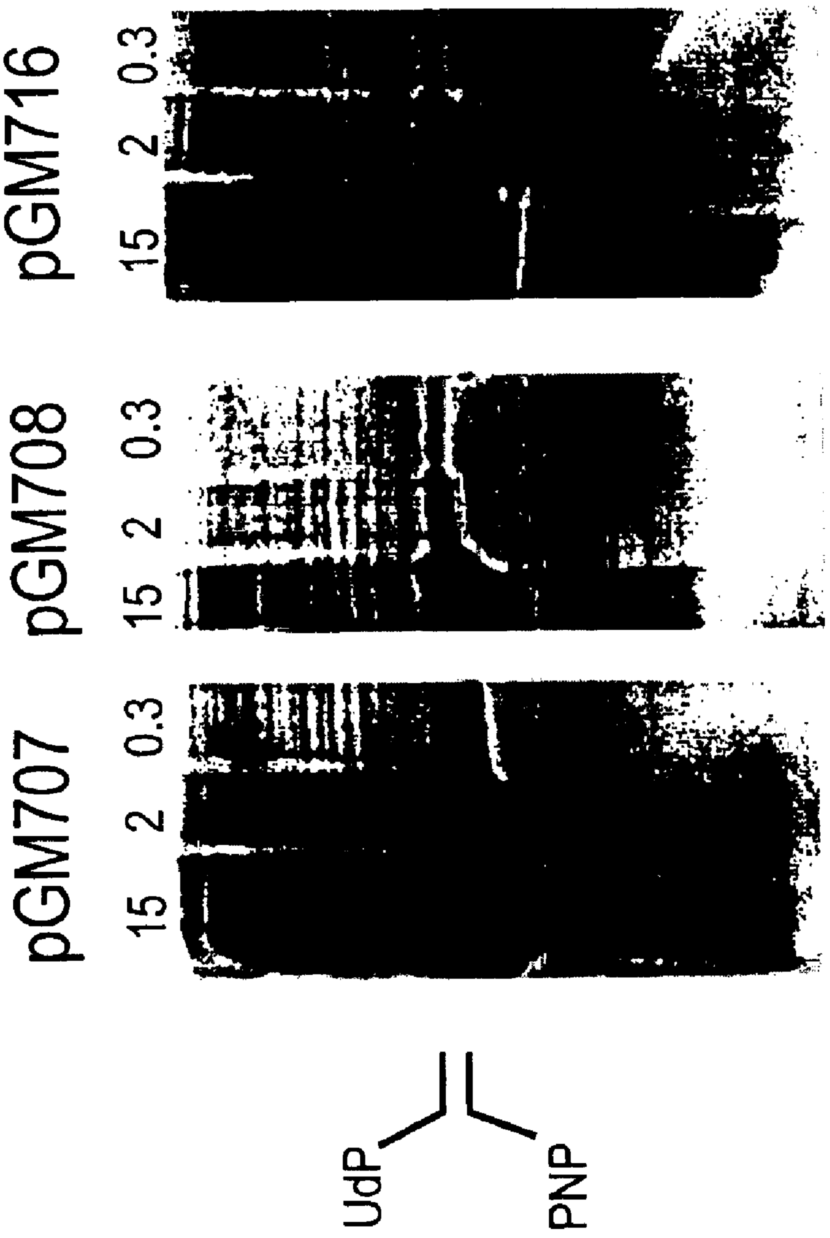
FIG. 5. Expression of PNP and UdP in recombinant *E. coli* strains. Gel electrophoresis (SDS-PAGE) of total protein exctracts from strains MG1655/pGM707, MG1655/pGM708, and MGl655/pGM716 grown overnight in LD medium supplemented with 12.5 mg/liter of tetracycline. Lanes 15, 2, and 0.3 correspond to protein extracted from 15, 2, and 0.3 ml of bacterial culture.

This high level of enzyme activity is also confirmed by the overexpression of the enzymes UdP and PNP which can be demonstrated both by electrophoretic analysis (FIG. 5) and by quantitative determination by RP-HPLC analysis which demonstrated levels of specific expression of from 55 to 120 milligrams of UdP/gram of wet cell paste and/or from 15 to 65 milligrams of PNP/gram of wet cell paste, as indicated in the example of Table 3.

TABLE 3

| Quantitative determination of UdP and PNP expression levels by RP-HPLC analysis. | | |
|---|---|---|
| Bacterial strains of the present invention | mg UdP/g wet cell paste | mg PNP/g wet cell paste |
| MG1655/pGM707 | — | 60 |
| MG1655/pGM716 | 55 | 15 |
| DH5α/pGM707 | — | 65 |
| DH5α/pGM708 | 120 | — |
| DH5α/pGM716 | 60 | 15 |

The whole cells of the recombinant strains described in the present invention, or their crude or purified extracts, can advantageously be used as biocatalysts for the preparation of natural nucleosides and modified analogues thereof starting from a sugar-donating nucleoside and from an acceptor base by means of bioconversion reactions which require the presence of only one type of phosphorylase (UdP or PNP) or the simultaneous presence of UdP and PNP according to the following general schemes:

a) pyrimidine nucleoside P1+pyrimidine base P2→pyrimidine nucleoside P2+pyrimidine base P1, in the presence of recombinant cells that overexpress UdP;

b) purine nucleoside P1+purine base P2→purine nucleoside P2+purine base P1, in the presence of recombinant cells that overexpress PNP, c) pyrimidine nucleoside+purine base→purine nucleoside+pyrimidine base, in the presence of a mixture of recombinant cells that overexpress UdP and PNP separately or of cells of a single recombinant strain that co-expresses UdP and PNP, d) purine nucleoside+pyrimidine base→pyrimidine nucleoside+pyrimidine base, in the presence of a mixture of recombinant cells that overexpress UdP and PNP separately or of cells of a single recombinant strain that co-express UdP and PNP.

According to the information given in the literature, in the bioconversion reactions catalysed by UdP and PNP, there come into consideration as donor nucleosides both natural or modified nucleosides containing D-ribose and 2'-deoxyribose, and nucleosides containing the ribose group modified in the 2', 3' and/or 5' positions and, in particular, nucleosides in which the sugar is constituted by β-D-arabinose, α-L-xylose, 3'-deoxyribose, 3',5 '-dideoxyribose, 2',3'-dideoxyribose, 5'-deoxyribose, 2',5'-dideoxyribose, 2'-amino-2'-deoxyribose, 3'-amino-3'-deoxyribose, 2'-fluoro-2'-deoxyribose. The acceptor bases which can be used in the bioconversion reactions catalysed by UdP and PNP are natural or substituted pyrimidine and purine bases, in particular purine bases substituted in the 1, 2 and/or 6 positions, pyrimidine bases substituted in the 3 and/or 5 positions and also other heterocyclic systems containing one or more nitrogen atoms, such as, for example, purine, 2-azapurine, 8-azapurine and substituted analogues thereof, 1-deazapurine (imidazopyridine), 3-deazapurine, 7-deazapurine and substituted analogues thereof, triazole and substituted analogues thereof, pyrazole and substituted analogues thereof, imidazole compounds and substituted analogues thereof.

Another method of preparing natural and modified nucleosides made possible by the present invention is to use recombinant cells or corresponding crude or purified cell extracts to catalyse the phosphorolysis reaction of a donor nucleoside (using UdP or PNP, depending on the base present in the donor nucleoside) and obtain α-sugar-1-phosphate which can optionally be isolated by chromatography, extraction or precipitation techniques and used in the subsequent reaction of transferring the sugar onto a suitable acceptor base in the presence of UdP or PNP (depending on the nature of the acceptor base).

The availability of recombinant bacterial strains which overexpress the UdP and PNP enzymes separately also enables the conditions of the transglycosylation reactions to be fixed, in terms of optimum activity of each of the two enzymes, by means of preliminary tests in which the reaction is carried out in the presence of mixtures containing varying proportions of cells of each of the two strains. For each transglycosylation reaction it is therefore possible to define, on an analytical scale, the optimum ratios of UdP and PNP enzyme activity while, in the subsequent preparative scale-up, it is possible to use either a mixture of cells of the two strains that express UdP and PNP individually, or only the strain that co-expresses UdP and PNP if their ratios are already optimum, or optionally the strain that co-expresses UdP and PNP, integrated with cells of strains expressing UdP or PNP. Such optimisation of the reaction conditions can be carried out using crude or purified cell extracts prepared from the cell paste of recombinant strains overexpressing UdP and PNP.

By way of example of optimisation of the bioconversion reactions in the present invention, a detailed description is given of the procedures relating to the preparation of 9-β-D-arabinofuranosyladenine(Ara-A) and 1-β-D-ribofuranosyl-1,2,4triazole-3-carboxamide (ribavirin) which indicated that the best results were obtained with UdP:PNP activity ratios of 2:1 and 1:1, respectively, and with a concentration of 10 units/ml of UdP and 5 units/ml of PNP for Ara-A and 10 units/ml of either UdP or PNP for ribavirin. These enzyme activity ratios, or others found to be optimum for the reaction concerned, can be readily implemented using the recombinant strains described in the present invention, in order to optimise the concentration of cells to be used as biocatalysts, while at the same time obtaining the maximum bioconversion yield compatible with the constants of equilibrium of the enzyme reactions and a reduction in the reaction times. Analogously, it is possible to optimise all the transglycosylation reactions for the preparation of nucleosides and modified analogues thereof.

When the novel recombinant strains expressing the fusion proteins UdP-PNP or UdP-(L)-PNP (or the corresponding crude or purified extracts) are used for the bioconversion reactions, there is the advantage of using bifunctionals polipeptides in which the components having the activity of enzymes UdP and PNP are present in the stechiometric ratio 1:1. Furthermore, as nucleosides production via bioconversion is carried out by way of two successive reactions catalyzed respectively by UdP and PNP, the use of biocatalysts based on the bifunctionals fusion proteins UdP-PNP or UdP-(L)-PNP according to the present invention may improve the overall kinetic of the reactions thanks to a more efficient transfer of intermediates products from a reaction site to the other one.

The novel recombinant strains described in the present invention enable natural nucleosides and modified nucleosides to be prepared with significantly better results than those obtained by the enzyme techniques known hitherto which are based on the use of isolated enzymes or on the use of bacterial cells of wild-type micro-organism strains and cultivated micro-organism strains under conditions for inducing the activities of the phosphorylase enzymes.

A comparison of various transglycosylation reactions which were carried out using constant ratios between the concentration of donor nucleoside (60 mM) and acceptor base (20 mM) and in which a productivity parameter was calculated (Simon et al., Angew Chem 24, 539–553, 1985) which, in addition to specific activity, also takes into account operating factors, such as, for example, intra-cellular and extra-cellular transport phenomena and the volumetric concentration of the end products, indicates that the use of the recombinant strains or of the corresponding crude or purified extracts to which the present invention relates is always characterised by greater bioconversion efficiency and by higher productivity per unit of time and of volume compared with the use of conventional micro-organisms (Table 4).

TABLE 4

Comparison of the efficiency of transglycosylation reactions catalysed by recombinant *Escherichia coli* cells (E) and by control *Enterobacter aerogenes* cells (C). The reactions were carried out at 60° C. for the time indicated, using the same concentrations of donor nucleoside (60 mM) and of acceptor base (20 mM). The bioconversion yield was calculated relative to the acceptor base by RP-HPLC analysis of the reaction mixture. The efficiency of the reaction is expressed by the productivity index P, calculated by the following formula $P = n \cdot m^{-1} \cdot t^{-1} \cdot 1000$ where n = concentration of the end product (g/l); m = wet cell paste (g/l of reaction mixture) and t = reaction time in hours.

| Product | Nucleoside 60 mM | Base 20 mM | Cell paste g/100 ml C | Cell paste g/100 ml E | t hours C | t hours E | Bioconversion % C | Bioconversion % E | P C | P E |
|---|---|---|---|---|---|---|---|---|---|---|
| Ribavirin | Uridine | 1,2,4-triazole-3-carbox-amide | 5 | 0.1 | 25 | 6 | 85 | 92 | 3 | 750 |
| 2'-deoxy-guanosine | 2'-deoxy-uridine | Guanine | 5 | 0.5 | 4 | 2 | 80 | 86 | 25 | 550 |
| 2'-deoxy-adenosine | 2'-deoxy-uridine | Adenine | 1 | 0.05 | 2 | 1 | 95 | 95 | 240 | 9600 |
| Thymidine | 2'-deoxy-uridine | Thymine | 0.5 | 0.05 | 1 | 3 | 59 | 60 | 600 | 2000 |
| 2'-deoxy-ribofuranosyl-2,6-diamino-purine | 2'-deoxy-uridine | 2,6-diamino-purine | 2 | 0.05 | 2 | 1.5 | 89 | 91 | 125 | 6660 |
| Ara-A | Ara-U | Adenine | 5 | 0.5 | 20 | 2 | 85 | 87 | 5 | 480 |

In particular, as shown in the example given in Table 5 regarding the preparation of Ara-A from Ara-U and adenine, the use of the recombinant strains enables conventional bioconversion processes to be improved both from the technical point of view and from the economic point of view and enables higher bioconversion yields, shorter reaction times, and a higher volumetric yield of end products to be obtained using a lower concentration of cells or corresponding crude or purified extract.

TABLE 5

Comparison of the operating conditions for the preparation of Ara-A by transglycosylation catalysed by recombinant *E. coli* cells and by a comparison *E. aerogenes* preparation.

| Operating conditions | Recombinant *E. coli* Cells | *E. aerogenes* Cells |
|---|---|---|
| Strain | MG1655/pGM716 or DH5α/pGM716 | Induced *E. aerogenes* ATCC 13048 |
| Ara-U: Adenine ratio | 75:75 (mM) | 40:40 (mM) |
| Cell concentration | 0.5% | 5% |
| Reaction time | 4 hours | 20 hours |
| Bioconversion yield | 70% | 55% |
| Volumetric yield | 14 g Ara-A/litre | 5 g Ara-A/litre |

A further advantage derived from the use of the recombinant strains to which the present invention relates is the simplification of the processes for recovering and re-using the cell biomass or the corresponding crude or purified cell extract resulting from the presence of a lower cell concentration; thus, for example, any recovery of the cells or the extract by filtration or ultrafiltration and their subsequent recycling is considerably faster when the recombinant strains described in the present invention are used. In some cases, in particular when substrates having a high affinity for enzymes are used, the concentration of recombinant cells or of the corresponding crude or purified cell extract is reduced to such low values that it may be economically advantageous to avoid having to recover them, with a further simplification of the production process.

The purpose of the Examples given below is to illustrate the present invention without constituting a limitation of the field of application thereof.

EXAMPLE NO. 1

Cloning of the udp Gene of *Escherichia coli* into an Expression Vector

The *E. coli* udp gene sequence was found in the EMBL data bank with the accession number X15689. The gene was amplified by PCR with the oligonucleotides 5'-ATCGGTACCATCCATGTCCAAGTCTGATGTTTTTCATCTC-3' (SEQ ID NO:16) and 5'-AGACGGTCGACAAGAGAATTACAGGAGACGACGC-3' (SEQ ID NO:17) from the *E. coli* strain K12 MG1655 (Singer et al., Microbiol. Rev. 53, 1-24, 1989). The amplified region comprises the entire sequence of the udp gene starting from the start codon ATG up to 7 bp downstream of the stop codon TAA. A KpnI restriction site was inserted at the 5' of the gene, followed by our bases selected at random. A SalI site is present at the 3' of the gene. The amplified fragment, digested with KpnI and SalI, was cloned into the polylinker region of the pUC18 vector which carries the ampicillin resistance gene (Yanish and Perron, Gene 33, 103–119, 1985; EMB accession number L08752). After transformation of the DH5α strain (Hanahan, J. Mol. Biol. 166, 557–580, 1983), the pGM679 plasmid was obtained (FIG. 1). In the construct, a fusion is created between the first codons of the lacZ gene of pUC18 and the entire udp sequence (FIG. 2) an the transcription is under the control of the lac promoter of the vector.

The cloned region was completely sequenced and it was found to be completely identical with the data bank sequence. The pGM679 plasmid sequence is listed.

The pBR322 Tet gene, which confers tetracycline resistance (Bolivar et al., Gene 2, 95–113, 1977; EMBL accession number J01749) was then inserted into the pGM679 plasmid. The gene, preceded by its promoter, was obtained by HindIII digestion from the interposon pBP45W708-Tet (Fellay et al, Gene 52, 147–154, 1987) and cloned into the HindIII site of pGM679. The resultant plasmid was named pGM708 (FIG. 1). Its complete sequence is listed.

EXAMPLE NO. 2

Cloning of the deoD Gene of *Escherichia coli* into an Expression Vector

The *E. coli* deoD gene sequence was found in the EMBL data bank with the accession number M60917. The gene was amplified by PCR with the oligonucleotides 5'-CTGAATTCTTCCATGGCTACCCCACACATTAATGCAG-3' (SEQ ID NO:18) and 5'-TCATGGTCGACTTACTCTTTATCGCCCAGCAGAACG-3' (SEQ ID NO:19) from the *E. coli* strain K12 M1655 (Singer et al., Microbiol. Rev. 53, 1–24, 1989). The amplified region comprises the entire sequence of the deoD gene starting fro the start codon ATG up to the stop codon TAA. EcoRI restriction site was inserted at the 5' of the gene, followed by four bases selected at random. A SalI site is presented at the 3' of the gene. The amplified fragment, digested with EcoRI and SalI, was cloned into the polylinker region of the pUC18 vector, which carries the gene for ampicillin resistance (Yanish and Perron, Gene 33, 103–119, 1985; EMBL accession number L08752). After transformation of the DH5α strain (Hanahan, J. Mol. Biol. 166, 557–580, 1983), the pGM678 plasmid was obtained (FIG. 1). In the construct, a fusion is created between the first codons of the lacZ gene of pUG18 and the entire deoD sequence (FIG. 2) and the transcription is under the control of the lac promoter of the vector. The cloned region was completely sequenced and was found to be completely identical with the data bank sequence. The pGM678 plasmid sequence is listed.

The Tet gene, which confers tetracycline resistance, was then inserted into the pGM678 plasmid, in a manner analogous to that described in Example No. 1. The resultant plasmid was called pGM707 (FIG. 1). Its complete sequence is listed.

The deoD gene was also cloned in a different vector as reported herebelow.

The region PvuII-NdeI of pUC18 plasmid (end filled with Klenow) containing the replication origin was linked to the fragment EcoRI (filled)-HindIII (filled) containing the polylinker to obtain the resulting plasmid pGM746whose sequence is listed. pGM746 was subsequently digested with BamHI (filled)-SphI and linked to fragment NheI (filled)-SphI of plasmid pGM709 in which is contained the deoD gene preceded by a Shine-Dalgamno sequence for the ribosome binding site (see example 3). The resulting plasmid was called pGM747 and its sequence is also listed.

The region containing the tac promoter was obtained by PCR amplification with oligonucleoties 5'-ATTGAGCTCGACATCATAACGGTTCTGGC (SEQ ID NO:20) and 5'-ATTGGATCCTGTGTGAAATTGTTATCCGC (SEQ ID NO:21) of plasmid pGZ119 (Lessl et al., J. Bacteriol. 74, 2493–2500, 1992), digestion of the fragment with BamHI-SacI and insertion in BamHI-SacI of pGM747 upstream deoD gene starting from tac promoter and expresses the PNP enzyme identical to the wild-type one. The pGM751 sequence is listed.

EXAMPLE NO. 3

Cloning of the udp and deoD Genes into a Single Expression Vector

The udp and deoD genes were cloned into the same vector in order to express the UdP and PNP enzymes simultaneously inside the same cell. This was effected by inserting the deoD gene into the pGM679 plasmid, downstream of udp. For the construction, the EcoRI-SalI fragment of pGM678, containing the deoD gene, was cloned into the pBAD24 vector (Guzman et al., J. Bacteriol. 177, 41214230, 1995; EMBL accession number X81838) obtaining plasmid pGM709. The fragment NheI (with the ends filled)—SphI of this construct was cloned into pGM679, digested SalI (filled)—SphI, to give pGM712 (FIG. 1). In pGM712, both of the udp and deoD genes are transcribed starting from the lac promoter, but the translation of deoD is independent of that of udp because a sequence for the attachment of ribosomes is present upstream of deoD (FIG. 2). It will be appreciated that the PNP protein expressed by pGM712 is identical to the wild protein because the fusion with the first codons of lacZ at the 5' of the gene was eliminated (FIG. 2). The complete pGM712 sequence is listed.

The Tet gene, which confers tetracycline resistance, was subsequently inserted into the pGM712 plasmid as described in Example No. 1. The resultant plasmid was called pGM716 (FIG. 1). Its complete sequence is listed.

The udp and deoD genes were also cloned in a different vector in which they are simultaneously expressed in this order starting from tac promoter, as herebelow reported.

The fragment SalI-HindIII, obtained by PCR amplification using the pGM679 DNA as a template an the oligonucleotides 5'-TCCAGTCGACACAGGAAACAGCTATGA (SEQ ID NO:22) and 5'-TACGAAGCTTA AGAGAATTACAGCAGACG (SEQ ID NO:23), was inserted into plasmid pGM751, digested with SalI-HindIII, in order to obtain plasmid pGM800 bearing gene udp cloned downstream deoD. Both genes are transcribed starting from ptac but the transduction is independent. The complete sequence of pGM800 is listed.

The gene Tc for tetracycline resistance was subsequently inserted into pGM800 according to an analogous process to that reported in example 1, thus obtaining plasmid pGM807 (FIG. 3) whose sequence is also listed.

EXAMPLE NO. 4

Cloning of Fusion Proteins UdP-PNP and UdP-(L)-PNP

The sequence coding for UdP and PNP have been fused to each other either directly or separated by a short aminoacidic linker. The plasmids were obtained by subsequent steps starting from pGM716. In particular, plasmid pGM716 was digested with HpaI and closed again so to have the decision in the terminal part of gene udp and in the starting part of deaD and create plasmid pGM769 with a unique site HpaI. The 3' portion of udp was amplified by PCR with the oligonucleotides 5'-GGCCGTTAACCGCACCCAGCAAGAG (SEQ D NO:24) and 5'-AGCCATGGACAGCAGACGACGCGCC (SEQ ID NO:25); the 5' portion of deaD was amplified in the same way with the oligonucleotides 5'-GCTGTCCATGGCTACCCCACACATTAAT (SEQ ID NO:26') and 5'-CCGGGTTAACTTTGGAATCGGTGCAGG (SEQ ID NO:27). Subsequently, using the product of the two PCRs as a template and the two extreme sequences, the compete region was amplified: the obtained fragment creates a fusion between udp and deaD, replacing the udp stop codon with a codon for serine, followed by deaD ATG codon. The fragment was digested with HpaI (site present at the two extremities) and cloned in pGM769 HpaI site. The resulting plasmid was called pQM771 (FIG. 4). In pGM771, the fused protein UdP-PNP is then transcribed starting from lac promoter. The plasmid sequence is listed.

Plasmid pM771 was subsequently modified by inserting the 5'-CATGGGCGGTGGCAGCCCGGGCATTCTGGC-CATG (SEQ ID NO:28) linker in the unique NcoI site, immediately upstream the starting deaD ATG. The resulting plasmid, called pGM795 (FIG. 4) expresses a fusion protein formed by UdP+ a 11 aminoacid linker (ser-met-gly-gly-gly-ser-pro-gly-ile-leu-ala) (SEQ ID NO:29)+PNP. The pGM795 sequence is listed.

EXAMPLE NO. 5

Transformation of *E. coli*

The *E. coli* strain K12 DH5α, which carries the recAl mutation (Hanahan, J. Mol. Biol. 166, 557–580, 1983) and the wild-type strain MG1655 (Singer et al., Microbiol.Rev. 53, 1–24, 1989) were transformed with plasmids pGM678, pGM679, pGM707, pGM708, pGM712, pGM716, pGM771, pGM795, pGM751, pGM800and pGM807. The genotype of the strains and some characteristics of the recombinant strains are given in Tables 6 and 7. The pGM678, pGM679, pGM712, pGM751 and pGM807 transformants were selected on medium containing ampicillin (50 μg/ml) and the pGM707, pGM708, pGM716, pGM771, pGM795 and and pGM907. pGM771, pGM795 and pGM807 transformants were selected on medium containing tetracycline (12.5 μg/ml).

TABLE 6

Genotype of the host strains

| Strain | Genotype | Reference |
|---|---|---|
| *E. coli* K12 DH5α | F,ϕ80dlacZΔMl5, Δ(lacZYA-argF)UI69, deoR, recA1, endA1, hsdR17($r_{K-}$, $m_{K+}$), phoA, supE44, N, thi 1, gyrA96, relA1 | Hanahan, J. Mol. Biol. 166, 557–580, 1983 |
| *E. coli* K12 MG1655 | LAM-rph-1 | Singer et al., Microbiol. Rev. 53, 1–24, 1989 |

TABLE 7

Characteristics of the novel recombinant strains

| Name of the strain | Expression of the cloned proteins | Resistence |
|---|---|---|
| DH5α/pGM678 | purine nucleoside phosphorylase | ampicillin |
| DH5α/pGM679 | uridine phosphorylase | ampicillin |
| DH5α/pGM707 | purine nucleoside phosphorylase | tetracycline/ ampicillin |
| DH5α/pGM708 | uridine phosphorylase | tetracycline/ ampicillin |
| DH5α/pGM712 | purine nucleoside phosphorylase and uridine phosphorylase | ampicillin |
| DH5α/pGM716 | purine nucleoside phosphorylase and uridine phosphorylase | tetracycline/ ampicillin |
| MG1655/pGM678 | purine nucleoside phosphorylase | ampicillin |
| MG1655/pGM679 | uridine phosphorylase | ampicillin |
| MG1655/pGM707 | purine nucleoside phosphorylase | tetracycline/ ampicillin |
| MG1655/pGM708 | uridine phosphorylase | tetracycline/ ampicillin |
| MG1655/pGM716 | purine nucleoside phosphorylase and uridine phosphorylase | tetracycline/ ampicillin |
| DH5α/pGM771 | fusion protein UdP-PNP | tetracycline/ ampicillin |
| DH5α/pGM795 | fusion protein UdP-(L)-PNP | tetracycline/ ampicillin |
| MG1655/pGM771 | fusion protein UdP-PNP | tetracycline/ ampicillin |
| MG1655/pGM795 | fusion protein UdP-(L)-PNP | tetracycline/ ampicillin |
| DH5α/pGM751 | purina nucleoside phosphorylase | ampicillin |

TABLE 7-continued

Characteristics of the novel recombinant strains

| Name of the strain | Expression of the cloned proteins | Resistence |
|---|---|---|
| DH5α/pGM800 | purine nucleoside phosphorylase and uridine phosphorylase | ampicillin |
| DH5α/pGM807 | purine nucleoside phosphorylase and uridine phosphorylase | tetracycline/ ampicillin |

The presence of the plasmid in the transformed strains was confirmed by extraction of the plasmid DNA and analysis on 0.6% agarose gel.

The growth of the transformed strains in LD broth (composition per liter: 10 g Bactotryptone (Difco), 5 g Yeast extract (Difco), 5 g NaCl) or in solid medium (LD+10 g/l agar), to which was added ampicillin (50 μg/ml) or tetracycline (12.5 μg/ml, only for the strains transformed with pGM707, pGM708, pGM716, pGM771, pGM795 and pGM807) is comparable to that of the control strains transformed with the pUC18 vector. In addition, the strains transformed with the plasmids pGM707, pGM708, pGM716, pGM771, pGM795 and pGM807, carrying both resistance genes, do not demonstrate differences in growth in the presence of ampicillin and tetracycline.

EXAMPLE NO. 6

Evaluation of the Expression of the UdP and PNP Proteins in the Recombinant Strains.

Precultures of the recombinant strains were obtained by inoculating single clones into LD medium to which an antibiotic had been added and by incubating without agitation at 37° C. overnight. The cultures were diluted 1:20 in LD medium+antibiotic in a flat-bottomed flask and incubated at 37° C. with agitation until the stationary phase was reached, corresponding to cell density values of approximately 2 units of optical density at 600 nm. The total proteins extracted from 1 ml of culture were separated on 15% polyacrylamide gel under reducing conditions (SDS-PAGE) and the proteins were visualised by staining with Coomassie Blue. The PNP and UdP proteins were identified on the basis of the molecular weight of approximately 26.6 kDa for PNP and 28.2 kDa for UdP. The result obtained from the extracts of strains MG1655/pGM707, pGM708 and pGM716 is given in FIG. 5. Electrophoretic analysis shows that, in all the samples studied, overexpression of UdP and PNP has occurred, because the corresponding protein bands represent a significant percentage of the total cell proteins; this result is confirmed by the quantitative determination of the enzyme activities which is given in Tables 1 and 2 and by the quantitative determination of UdP and PNP expression effected by reverse phase high pressure liquid chromatography (RP-BPLC). For that purpose, the soluble extract was analysed on a C4-Vydac analytical column, dimensions 4.6×250 mm, using a mobile phase constituted by acetonitrile-$H_2O$ containing 0.1% trifluoroacetic acid and operating in accordance with the following parameters: flow rate of 0.75 ml/minute; elution with a gradient from 40% acetonitrile to 65% acetonitrile in 30 minutes; temperature of 45° C.; UV detection at a wavelength of 215 nm. Under the analysis conditions applied, the elution times for UdP and PNP were approximately 13 minutes and 15 minutes, respectively The quantitative determination was carried out by comparing the area of the peak of interest with the area of the peak of standard UdP and PNP preparations separated under the same conditions as the samples.

Because, in the recombinant strains, the deoD and udp genes are cloned under the control of the lac promoter, the growth of the cells and the expression of the UdP and PNP proteins were monitored both in the absence and in the presence of 40 mg/l of IPTG as transcription inducer. The results obtained indicated that the presence of IPTG does not modify cell growth and does not increase the level of PNP and UdP expression (possibly due to the insufficient amount of repressor in those strains). This last result indicates that, in the recombinant strains to which the present invention relates, the expression of the deoD and udp genes is constitutive and reaches very high levels without phenomena of cell damages or diminished cell vitality.

EXAMPLE NO. 7

Determination of the Enzyme Activity of Uridine Phosphorylase and Purine Nucleoside Phosphorylase Expressed Intracellularly in Recombinant Bacterial Cells.

The strains were grown as described in Example No. 5. The cells were harvested by centrifugation, weighed in the form of wet cell paste and stored at −20° C. until enzyme analysis was carried out.

The activity of the UdP enzyme was determined in a phosphorolysis test by incubating for 5 minutes at 30° C. the soluble fraction (cell extract) obtained by sonication of a known amount of a suspension of the cell paste and by centrifugation of the homogenate in 100 mM-pH 7 phosphate buffer containing 60 mM of the uridine substrate. The enzyme reaction was blocked by acidification with 0.1N HCl; the suspension was filtered and analysed by RP-HPLC on a C18 column (Hypersyl 100; 4.6×250 mm), eluting under isocratic conditions with a mobile phase constituted by 0.02 M $K_2HPO_4$ in methanol-$H_2O$ (4:96 v/v) and adjusted to pH 4.5 with $NH_4OH$. The amount of uracil formed in the reaction was determined by reference to a standard curve and the enzyme activity of the cell preparation was calculated in μmol uracil/min/g wet cell paste (units/g). The activity of the PNP enzyme was determined in a phosphorolysis test by incubating for 10 minutes at 30° C. the soluble fraction (cell extract) obtained by sonication of a known amount of a suspension of the cell paste and by centrifugation of the homogenate in 100 mM-pH 7 phosphate buffer containing 50 mM of the inosine substrate. The enzyme reaction was blocked by acidification with 0.1N HCl; the suspension was filtered and analysed by RP-HPLC on a C18 column (Hypersyl 100; 4.6×250 mm), eluting under isocratic conditions with a mobile phase constituted by 0.02 M $K_2HPO_4$ in methanol-$H_2O$ (4:96 v/v) and adjusted to pH 4.5 with $NH_4OH$. The amount of hypoxanthine formed in the reaction was determined by reference to a standard curve and the enzyme activity of the cell preparation was calculated in μmol hypoxanthine/min/g wet cell paste (units/g).

EXAMPLE NO. 8

Fermentation of the Recombinant Strains.

The recombinant strains to which the present invention relates were cultivated at high biomass either under batch mode or under fed-batch mode fermentation conditions.

The batch-mode fermentations were carried out using a fermenter having a working volume of 10 liters which was filled with 9 liters of medium having the following composition (per liter): 0.6 g $KH_2PO_4$; 3.2 g $K_2HPO_4$; 20 g Soytone (Difco); 36 g yeast extract (Difco); 1 g $MgSO_4$-$7H_2O$; 0.0125 g tetracycline (or other antibiotic used as a selection marker) and which was inoculated with 1 liter of a bacterial suspension previously cultivated for 20 hours at 30° C. in medium having the following composition, per liter: 20 g tryptone; 10 g yeast extract; 10 g NaCl; 0.0125 g tetracycline.

The fermentation was carried out in accordance with the following operating parameters: 30° C.; air flow of 1 liter/liter of culture/minute; initial agitation 250 rev/min modified automatically to maintain a level of $O_2$ at 20% of the saturation concentration; pH maintained at 7 by additions of $H_3PO_4$ or $NH_4OH$; time 24 hours. When fermentation was complete, the culture medium was centrifuged, the cell pellet was washed in 30 mM-pH 7 phosphate buffer. The biomass obtained (40–50 grams of wet cell paste/liter of culture medium) was stored at −20° C. until it was brought into use.

The fed-batch mode fermentations ,were carried out using a fermenter having a working volume of 10 liters which was filled with 7 liters of medium at pH 6.8–7 having the following composition, per liter: 13.3 g $KH_2PO_4$; 4 g $(NH_4)_2HOP_4$; 1.25 g Soytone (Difco); 0.125 g yeast extract (Difco); 1.7 g citric acid; 2.5 g glycerol; 1.5 g $MgSO_4$-$7H_2O$; 0.08 g $CaCl_2$; 0.01 g thiamine, 0.0125 g tetracycline (or other antibiotic selector); 0.08 g $FeSO_4$-$7H_2O$; 0.02 g $MnSO_4$—$H_2O$; 0.03 g $ZnSO_4$-$7H_2O$; 0.003 g $H_3BO_3$; 0.06 g $CuSO_4$-$5H_2O$; 0.008 g $CoCl_2$-$6H_2O$; 0.004 g $NaMoO_4$-$2H_2O$. The fermenter was inoculated with 1 liter of bacterial suspension previously cultivated for 18–20 hours at 30° C. in medium having the following composition, per liter: 13.3 g $KH_2PO_4$; 4 g $NH_4)2HPO_4$; 5 g Soytone (Difco); 1.7 g citric acid; 10 g glycerol; 0.01 g thiamine; 0.0125 g tetracycline; 0.05 g $CaCl_2$-$2H_2O$; 1 g $MgSO_4$-$7H_2O$; 0.03 g $FeSO_4$-$7H_2O$; 0.01 g $MnSO_4$—$H_2O$; 0.01 g $ZnSO_4$-$7H_2O$; 0.003 g $H_3BO_3$; 0.02 g $CuSO_4$-$5H_2O$; 0.002 g $CoCl_2$-$6H_2O$; 0.002 g $NaMoO_4$-$2H_2O$.

The fermentation was carried out in accordance with the following operating parameters: 30° C.; air flow of 1–1.2 liter/liter of culture/minute; initial agitation 150 rev/min modified automatically to maintain a level of $O_2$ at 20% of the saturation concentration for approximately 8–10 hours (batch phase) and subsequently a level of $O_2$ at 10% of the saturation concentration (fed-batch phase); pH maintained at 6.8–7 by additions of $H_3PO_4$ or $NH_4OH$. During the fed-batch phase, the fermentation was automatically supplied with a total of 2 liters of a solution having the following composition, per liter: 400 g glycerol; 200 g Soytone; 20 g yeast extract; 3 g $MgSO_4$-$7H_2O$; 0.0125 g tetracycline. When fermentation was completed (after approximately 50 hours) the culture medium was centrifuged, the cell pellet was washed in 30 mM-pH 7 phosphate buffer. The biomass obtained (150–200 grams of wet cell paste/liter of culture medium) was stored at −20° C. until it was brought into use.

EXAMPLE NO. 9

Transglycosylation Reactions on a Laboratory Scale and Calculation of the Productivity Index The transglycosylation reactions were carried out using various sugar-donating nucleosides at a concentration of 60 mM (uridine, 2'-deoxyuridine, Ara-U) and various acceptor bases at a concentration of 20 mM (1,2,4triazole-3-carboxamide, guanine, adenine, thymine, 2,6-diaminopurine) at pH 7 in phosphate buffer (30 mM) in the presence of various concentrations of cell paste or corresponding crude or purified extract derived either from cultures of the control micro-organism *E. aerogenes* or from cultures of the recombinant *E. coli* strain MG1655/pGM716 which overexpresses the UdP and PNP enzymes. The reactions were carried out at 60° C. for various periods of time (from 1 hour to 25 hours) and the percentage bioconversion, relative to the initial concentration of acceptor base, was determined by RP-HPLC analysis of the diluted reaction mixture. The results obtained are given in Table 2.

The productivity index P was calculated for each reaction by applying the following formula:

$$P=n \cdot m^{-1} \cdot t^{-1} \cdot 1000$$

where n=concentration of the end product (g/l)
m=wet cell paste (g/l of reaction mixture)
t=reaction time in hours.

The productivity index represents an overall measure of the efficiency of the reaction because it takes into account both the characteristics of the enzyme-substrate interaction itself and operating parameters, such as the reaction time, the amount of cells used and the volumetric yield of end product.

EXAMPLE NO. 10

Optimisation of the Use of Recombinant *E. coli* Cells in Transglycosylation Reactions The preparation of ribavirin starting from uridine (60 mM) and 1,2,4-triazole-3-carboxamide (40 mm) and of Ara-A starting from Ara-U (40 mM) and adenine (40 mM) were studied as examples of optimisation of the use of recombinant *E. coli* cells in bioconversion reactions. In each case, the reactions were carried out at 60° C. in the presence of 30 mM of potassium phosphate at pH 7 and in the presence of various amounts of cell paste obtained by fermentation of the strains MG1655/pGM707 (overexpressing the UdP enzyme) and MG1655/pGM708 (overexpressing the PNP enzyme). At predetermined intervals, aliquots of the reaction mixture were taken and analysed by RP-HPLC in order to determine the percentage bioconversion (calculated relative to the concentration of acceptor base).

The study was initially carried out by incubating the reaction mixture for 20 hours in the presence of a limiting concentration of cell paste (with total enzyme activity equal to or less than 2 units/ml) and by operating in such a manner as to have ratios of UdP enzyme units and PNP enzyme units varying in the following proportions 5:1, 2:1; 1:1 ; 1:2; 1:5.

The results obtained in the two bioconversion reactions are given in Table 8.

TABLE 8

Study of the transglycosylation reaction conditions
The reactions were carried out for 20 hours at 60° C. in the presence of limiting concentrations of cell paste.

| Preparation of ribavirin | | | Preparation of Ara-A | | |
|---|---|---|---|---|---|
| UdP units/ml | PNP units/ml | Bioconversion yield % | UdP units/ml | PNP units/ml | Bioconversion yield % |
| 1 | 0.2 | 60.7 | 1 | 0.2 | 54.0 |
| 1 | 0.5 | 77.3 | 1 | 0.5 | 65.2 |
| 1 | 1 | 81.6 | 1 | 1 | 63.8 |
| 0.5 | 1 | 80.0 | 0.5 | 1 | 26.4 |
| 0.2 | 1 | 78.1 | 0.2 | 1 | 9.2 |

The results given in the Table demonstrate that the optimum UdP and PNP activity ratios are 1:1 and 1:0.5, respectively, for the reaction for the formation of ribavirin and Ara-A.

These data were confirmed in the subsequent study in which enzyme concentrations 10 times higher were used, with the same proportions being maintained between the UdP units and the PNP units; in this study, the reaction kinetics were also determined by taking samples of reaction mixture at intervals of 1 hour for RP-BPLC analysis and calculation of the percentage bioconversion.

Tables 9 and 10 show, for the ribavirin and Ara-A preparation reactions, respectively, the optimum parameters in terms of percentage bioconversion and reaction time for the various proportions of UdP and PNP studied.

TABLE 9

Optimisation of the reaction conditions for the preparation of ribavirin

| UdP units/ml | PNP units/ml | Reaction time hours | Bioconversion % |
|---|---|---|---|
| 10 | 2 | 20 | 89.4 |
| 10 | 5 | 4 | 89.5 |
| 10 | 10 | 2 | 91.2 |
| 5 | 10 | 2 | 91.2 |
| 2 | 10 | 2 | 91.1 |

TABLE 10

Optimisation of the reaction conditions for the preparation of Ara-A.

| UdP units/ml | PNP units/ml | Reaction time hours | Bioconversion % |
|---|---|---|---|
| 10 | 2 | 3 | 70.5 |
| 10 | 5 | 2 | 70.8 |
| 10 | 10 | 2 | 70.6 |
| 5 | 10 | 6 | 70.1 |
| 2 | 10 | 6 | 70.0 |

The results of the optimisation study indicate that ribavirin can be obtained in two hours with a bioconversion yield of 91% using 10 units/ml of either UdP or PNP while Ara-A can be obtained in two hours with a bioconversion yield of approximately 71% using 10 units/ml of Udp and 5 units/ml of PNP.

On the basis of the enzyme activity titre of the recombinant *E. coli* strains described in the present invention, it is therefore possible to calculate the amount of cell paste necessary to prepare ribavirin and Ara-A under optimum conditions. In the case, for example, of the strains MG1655/pGM707 and MG1655/pGM716 having the specific activities given in Table 1, 0.4 and 0.2 gram of wet cell paste/100 ml of reaction mixture, respectively, will be used for the preparation of ribavirin and Ara-A.

EXAMPLE NO. 11

Pilot-Scale Preparation of Ara-A by Transglycosylation Reaction Carried Out with the *E. aerogenes* Comparison Strain, with the Recombinant *E. coli* Strains and with the Corresponding Cell Extracts.

The process for the preparation of Ara-A by transglycosylation catalysed by *E. aerogenes* cells or by recombinant cells of *E. coli* MG1655/pGM716 or DH5α/pGM716 overexpressing UdP and PNP was studied on a reaction scale of 1000 liters.

50 kg of wet cell paste obtained by fermenting *E. aerogenes* were resuspended in approximately 200 liters of 30 mM phosphate buffer at pH 7 and mixed with 800 liters of phosphate buffer in which had been dissolved at elevated temperature 5.4 kg of adenine (final concentration 40 mM) and 8.9 kg of Ara-U (final concentration 40 mM). The mixture was maintained at 60° C., with agitation, for 20 hours, diluted to approximately 3000 liters with hot $H_2O$ and subjected to diafiltration on a membrane, collecting approximately 5000 liters of ultrafiltrate. The bioconversion yield determined by RP-HPLC was approximately 55%. The residue containing the cell paste is used for a subsequent reaction. The ultrafiltrate was concentrated to approximately 1000 liters and cooled to collect the precipitate constituted by Ara-A contaminated with non-reacted adenine (approximately 30 g of adenine per 100 g of Ara-A). 5 kg of Ara-A (total yield approximately 46%) with a degree of purity higher than 99.5% were finally obtained after crystallisation with $H_2O$.

5 kg of wet cell paste or the corresponding crude or purified extract obtained by fermenting the strain MG1655/pGM716 or the strain DH5α/pGM716 were resuspended in approximately 20 liters of 30 mM phosphate buffer at pH 7 and mixed with 980 liters of phosphate buffer in which had been dissolved at elevated temperature 10.1 kg of adenine (final concentration approximately 74.6 mM) and 18.3 kg of Ara-U (final concentration approximately 74.6 mM). The mixture was maintained at 60° C., with agitation, for 4 hours to obtain a bioconversion yield of approximately 70%. The cell paste was recovered in order to be used again in subsequent reactions by dilution at elevated temperature and diafiltration in accordance with the procedure described above. The ultrafiltrate was concentrated to a volume of approximately 1000 liters, cooled to collect the precipitate constituted by Ara-A which was subsequently crystallised from water to obtain approximately 14 kg of Ara-A with a degree of purity higher than 99.5%. According to an alternative procedure, in which the cells were not recovered and the diafiltration step was omitted, at the end of the reaction the mixture was heated to approximately 90° C. and filtered at elevated temperature to eliminate the cells, and the filtrate was cooled to precipitate Ara-A contaminated with non-reacted adenine (approximately 20 g of adenine per 100 g of Ara-A). 14 kg of Ara-A (total yield 65%) having a degree of purity higher than 99.5% were finally obtained after crystallisation from reaction of 1000 liters. Similar results were obtained starting from a mixture of the cell pastes or the corresponding crude or purified extracts obtained by fermenting the recombinant *E. coli* strains MG1655/p707 or MG1655/p708 and the strains DH5α/pGM707 or DH5α/pGM707 overexpressing UdP and PNP, respectively.

What is claimed is:

1. A plasmid vector having the sequence of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:12, SEQ ID NO:13, SEQ ID NO:14, or SEQ ID NO:15.

2. A method for producing a first protein having uridine phosphorylase activity and a second protein having purine nucleoside phosphorylase activity in the same cell, said method comprising culturing a host bacterial cell harboring a plasmid expression vector having the sequence as depicted in SEQ ID NO: 6 or a plasmid expression vector having the sequence as depicted in SEQ ID NO: 15, wherein the proteins are produced.

3. The method of claim 2, further comprising the steps of isolating and purifying the proteins from the host bacterial cell.

4. A method for producing a fusion protein having both uridine phosphorylase activity and purine nucleoside phosphorylase activity, said method comprising culturing a host bacterial cell harboring a plasmid expression vector having the sequence as depicted in SEQ ID NO: 9, wherein the protein is produced.

5. The method of claim 4, further comprising the steps of isolating and purifying the protein from the host bacterial cell.

6. A method for producing a fusion protein having both uridine phosphorylase activity and puring nucleoside phosphorylase activity, said method comprising culturing a host bacterial cell harboring a plasmid expression vector having the sequence as depicted in SEQ ID NO: 10, wherein the protein is produced.

7. The method of claim 6, further comprising the steps of isolating and purifying the fusion protein from the host bacterial cell.

* * * * *

SEQUENCE LISTING

```
<160> NUMBER OF SEQ ID NOS: 29

<210> SEQ ID NO 1
<211> LENGTH: 3444
<212> TYPE: DNA
<213> ORGANISM: Artificial Sequence
<220> FEATURE:
<223> OTHER INFORMATION: plasmid
<220> FEATURE:
<221> NAME/KEY: gene
<222> LOCATION: (243)..(1021)
<223> OTHER INFORMATION: udp

<400> SEQUENCE: 1

gcgcccaata cgcaaaccgc ctctccccgc gcgttggccg attcattaat gcagctggca     60

cgacaggttt cccgactgga aagcgggcag tgagcgcaac gcaattaatg tgagttagct    120

cactcattag gcaccccagg ctttacactt tatgcttccg gctcgtatgt tgtgtggaat    180

tgtgagcgga taacaatttc acacaggaaa cagctatgac catgattacg aattcgagct    240

cggtaccatc catgtccaag tctgatgttt ttcatctcgg cctcactaaa aacgatttac    300

aaggggctac gcttgccatc gtccctggcg acccggatcg tgtggaaaag atcgccgcgc    360

tgatggataa gccggttaag ctggcatctc accgcgaatt cactacctgg cgtgcagagc    420

tggatggtaa acctgttatc gtctgctcta ccggtatcgg cggcccgtct acctctattg    480

ctgttgaaga gctggcacag ctgggcattc gcaccttcct gcgtatcggt acaacgggcg    540

ctattcagcc gcatattaat gtgggtgatg tcctggttac cacggcgtct gtccgtctgg    600

atggcgcgag cctgcacttc gcaccgctgg aattcccggc tgtcgctgat ttcgaatgta    660

cgactgcgct ggttgaagct gcgaaatcca ttggcgcgac aactcacgtt ggcgtgacag    720

cttcttctga taccttctac ccaggtcagg aacgttacga tacttactct ggtcgcgtag    780

ttcgtcactt taaaggttct atggaagagt ggcaggcgat gggcgtaatg aactatgaaa    840

tggaatctgc aaccctgctg accatgtgtg caagtcaggg cctgcgtgcc ggtatggtag    900

cgggtgttat cgttaaccgc acccagcaag agatcccgaa tgctgagacg atgaaacaaa    960

ccgaaagcca tgcggtgaaa atcgtggtgg aagcggcgcg tcgtctgctg taattctctt   1020

gtcgacctgc aggcatgcaa gcttggcact ggccgtcgtt ttacaacgtc gtgactggga   1080
```

-continued

```
aaaccctggc gttacccaac ttaatcgcct tgcagcacat ccccctttcg ccagctggcg   1140

taatagcgaa gaggcccgca ccgatcgccc ttcccaacag ttgcgcagcc tgaatggcga   1200

atggcgcctg atgcggtatt ttctccttac gcatctgtgc ggtatttcac accgcatatg   1260

gtgcactctc agtacaatct gctctgatgc cgcatagtta agccagcccc gacacccgcc   1320

aacacccgct gacgcgccct gacgggcttg tctgctcccg gcatccgctt acagacaagc   1380

tgtgaccgtc tccgggagct gcatgtgtca gaggttttca ccgtcatcac cgaaacgcgc   1440

gagacgaaag ggcctcgtga tacgcctatt tttataggtt aatgtcatga taataatggt   1500

ttcttagacg tcaggtggca cttttcgggg aaatgtgcgc ggaaccccta tttgtttatt   1560

tttctaaata cattcaaata tgtatccgct catgagacaa taaccctgat aaatgcttca   1620

ataatattga aaaaggaaga gtatgagtat tcaacatttc cgtgtcgccc ttattccctt   1680

ttttgcggca ttttgccttc ctgtttttgc tcacccagaa acgctggtga aagtaaaaga   1740

tgctgaagat cagttgggtg cacgagtggg ttacatcgaa ctggatctca acagcggtaa   1800

gatccttgag agttttcgcc ccgaagaacg ttttccaatg atgagcactt ttaaagttct   1860

gctatgtggc gcggtattat cccgtattga cgccgggcaa gagcaactcg gtcgccgcat   1920

acactattct cagaatgact tggttgagta ctcaccagtc acagaaaagc atcttacgga   1980

tggcatgaca gtaagagaat tatgcagtgc tgccataacc atgagtgata acactgcggc   2040

caacttactt ctgacaacga tcggaggacc gaaggagcta accgcttttt tgcacaacat   2100

gggggatcat gtaactcgcc ttgatcgttg ggaaccggag ctgaatgaag ccataccaaa   2160

cgacgagcgt gacaccacga tgcctgtagc aatggcaaca acgttgcgca aactattaac   2220

tggcgaacta cttactctag cttcccggca acaattaata gactggatgg aggcggataa   2280

agttgcagga ccacttctgc gctcggccct tccggctggc tggtttattg ctgataaatc   2340

tggagccggt gagcgtgggt ctcgcggtat cattgcagca ctggggccag atggtaagcc   2400

ctcccgtatc gtagttatct acacgacggg gagtcaggca actatggatg aacgaaatag   2460

acagatcgct gagataggtg cctcactgat taagcattgg taactgtcag accaagttta   2520

ctcatatata ctttagattg atttaaaact tcatttttaa tttaaaagga tctaggtgaa   2580

gatccttttt gataatctca tgaccaaaat cccttaacgt gagttttcgt tccactgagc   2640

gtcagacccc gtagaaaaga tcaaaggatc ttcttgagat cctttttttc tgcgcgtaat   2700

ctgctgcttg caaacaaaaa aaccaccgct accagcggtg gtttgtttgc cggatcaaga   2760

gctaccaact ctttttccga aggtaactgg cttcagcaga gcgcagatac caaatactgt   2820

ccttctagtg tagccgtagt taggccacca cttcaagaac tctgtagcac cgcctacata   2880

cctcgctctg ctaatcctgt taccagtggc tgctgccagt ggcgataagt cgtgtcttac   2940

cgggttggac tcaagacgat agttaccgga taaggcgcag cggtcgggct gaacgggggg   3000

ttcgtgcaca cagcccagct tggagcgaac gacctacacc gaactgagat acctacagcg   3060

tgagctatga gaaagcgcca cgcttcccga agggagaaag gcggacaggt atccggtaag   3120

cggcagggtc ggaacaggag agcgcacgag ggagcttcca gggggaaacg cctggtatct   3180

ttatagtcct gtcgggtttc gccacctctg acttgagcgt cgatttttgt gatgctcgtc   3240

aggggggcgg agcctatgga aaaacgccag caacgcggcc tttttacggt tcctggcctt   3300

ttgctggcct tttgctcaca tgttctttcc tgcgttatcc cctgattctg tggataaccg   3360

tattaccgcc tttgagtgag ctgataccgc tcgccgcagc cgaacgaccg agcgcagcga   3420

gtcagtgagc gaggaagcgg aaga                                          3444
```

-continued

<210> SEQ ID NO 2
<211> LENGTH: 5556
<212> TYPE: DNA
<213> ORGANISM: Artificial Sequence
<220> FEATURE:
<223> OTHER INFORMATION: plasmid
<220> FEATURE:
<221> NAME/KEY: gene
<222> LOCATION: (243)..(1021)
<223> OTHER INFORMATION: udp
<220> FEATURE:
<221> NAME/KEY: gene
<222> LOCATION: (1483)..(2883)
<223> OTHER INFORMATION: tetracycline resistance

<400> SEQUENCE: 2
gcgcccaata cgcaaaccgc ctctccccgc gcgttggccg attcattaat gcagctggca 60
cgacaggttt cccgactgga aagcgggcag tgagcgcaac gcaattaatg tgagttagct 120
cactcattag gcaccccagg ctttacactt tatgcttccg gctcgtatgt tgtgtggaat 180
tgtgagcgga taacaatttc acacaggaaa cagctatgac catgattacg aattcgagct 240
cggtaccatc catgtccaag tctgatgttt ttcatctcgg cctcactaaa aacgatttac 300
aaggggctac gcttgccatc gtccctggcg acccggatcg tgtggaaaag atcgccgcgc 360
tgatggataa gccggttaag ctggcatctc accgcgaatt cactacctgg cgtgcagagc 420
tggatggtaa acctgttatc gtctgctcta ccggtatcgg cggcccgtct acctctattg 480
ctgttgaaga gctggcacag ctgggcattc gcaccttcct gcgtatcggt acaacgggcg 540
ctattcagcc gcatattaat gtgggtgatg tcctggttac cacggcgtct gtccgtctgg 600
atggcgcgag cctgcacttc gcaccgctgg aattcccggc tgtcgctgat ttcgaatgta 660
cgactgcgct ggttgaagct gcgaaatcca ttggcgcgac aactcacgtt ggcgtgacag 720
cttcttctga taccttctac ccaggtcagg aacgttacga tacttactct ggtcgcgtag 780
ttcgtcactt taaaggttct atggaagagt ggcaggcgat gggcgtaatg aactatgaaa 840
tggaatctgc aaccctgctg accatgtgtg caagtcaggg cctgcgtgcc ggtatggtag 900
cgggtgttat cgttaaccgc acccagcaag agatcccgaa tgctgagacg atgaaacaaa 960
ccgaaagcca tgcggtgaaa atcgtggtgg aagcggcgcg tcgtctgctg taattctctt 1020
gtcgacctgc aggcatgcaa gctttatgct tgtaaaccgt tttgtgaaaa aatttttaaa 1080
ataaaaaagg ggacctctag ggtccccaat taattagtaa tataatctat taaaggtcat 1140
tcaaaaggtc atccaccgga tcagcttagt aaagccctcg ctagatttta atgcggatgt 1200
tgcgattact tcgccaacta ttgcgataac aagaaaaagc cagcctttca tgatatatct 1260
cccaatttgt gtagggctta ttatgcacgc ttaaaaataa taaaagcaga cttgacctga 1320
tagtttggct gtgagcaatt atgtgcttag tgcatctaac gcttgagtta agccgcgccg 1380
cgaagcggcg tcggcttgaa cgaattgtta gacattattt gccgactacc ttggtgatct 1440
cgcctttcac gtagtggaca aattcttcca actgatctgc gcgccgagat gcgccgcgtg 1500
cggctgctgg agatggcgga cgcgatggat atgttctgcc aagggttggt ttgcgcattc 1560
acagttctcc gcaagaattg attggctcca attcttggag tggtgaatcc gttagcgagg 1620
tgccgccggc ttccattcag gtcgaggtgg cccggctcca tgcaccgcga cgcaacgcgg 1680
ggaggcagac aaggtatagg gcggcgccta caatccatgc caacccgttc catgtgctcg 1740
ccgaggcggc ataaatcgcc gtgacgatca gcggtccagt gatcgaagtt aggctggtaa 1800
gagccgcgag cgatccttga agctgtccct gatggtcgtc atctacctgc ctggacagca 1860

-continued

```
tggcctgcaa cgcgggcatc ccgatgccgc cggaagcgag aagaatcata atggggaagg   1920
ccatccagcc tcgcgtcgcg aacgccagca agacgtagcc cagcgcgtcg gccgccatgc   1980
cggcgataat ggcctgcttc tcgccgaaac gtttggtggc gggaccagtg acgaaggctt   2040
gagcgagggc gtgcaagatt ccgaataccg caagcgacag gccgatcatc gtcgcgctcc   2100
agcgaaagcg gtcctcgccg aaaatgaccc agagcgctgc cggcacctgt cctacgagtt   2160
gcatgataaa gaagacagtc ataagtgcgg cgacgatagt catgccccgc gcccaccgga   2220
aggagctgac tgggttgaag gctctcaagg gcatcggtcg acgctctccc ttatgcgact   2280
cctgcattag gaagcagccc agtagtaggt tgaggccgtt gagcaccgcc gccgcaagga   2340
atggtgcatg caaggagatg gcgcccaaca gtcccccggc cacggggcct gccaccatac   2400
ccacgccgaa acaagcgctc atgagcccga agtggcgagc ccgatcttcc ccatcggtga   2460
tgtcggcgat ataggcgcca gcaaccgcac ctgtggcgcc ggtgatgccg gccacgatgc   2520
gtccggcgta gaggatccac aggacgggtg tggtcgccat gatcgcgtag tcgatagtgg   2580
ctccaagtag cgaagcgagc aggactgggc ggcggccaaa gcggtcggac agtgctccga   2640
gaacgggtgc gcatagaaat tgcatcaacg catatagcgc tagcagcacg ccatagtgac   2700
tggcgatgct gtcggaatgg acgatatccc gcaagaggcc cggcagtacc ggcataacca   2760
agcctatgcc tacagcatcc agggtgacgg tgccgaggat gacgatgagc gcattgttag   2820
atttcataca cggtgcctga ctgcgttagc aatttaactg tgataaacta ccgcattaaa   2880
gctcatgcgg atcagtgagg gtttgcaact gcgggtcaag gatctggatt tcgatcacgg   2940
cacgatcatc gtgcgggagg gcaagggctc caaggatcgg gccttgatgt tacccgagag   3000
cttggcaccc agcctgcgcg agcaggggaa ttgatccggt ggatgacctt ttgaatgacc   3060
tttaatagat tatattacta attaattggg gaccctagag gtcccctttt ttattttaaa   3120
aatttttttca caaaacggtt tacaagcata aagcttggca ctggccgtcg ttttacaacg   3180
tcgtgactgg gaaaaccctg gcgttaccca acttaatcgc cttgcagcac atcccccttt   3240
cgccagctgg cgtaatagcg aagaggcccg caccgatcgc ccttcccaac agttgcgcag   3300
cctgaatggc gaatggcgcc tgatgcggta ttttctcctt acgcatctgt gcggtatttc   3360
acaccgcata tggtgcactc tcagtacaat ctgctctgat gccgcatagt taagccagcc   3420
ccgacacccg ccaacacccg ctgacgcgcc ctgacgggct tgtctgctcc cggcatccgc   3480
ttacagacaa gctgtgaccg tctccgggag ctgcatgtgt cagaggtttt caccgtcatc   3540
accgaaacgc gcgagacgaa agggcctcgt gatacgccta tttttatagg ttaatgtcat   3600
gataataatg gtttcttaga cgtcaggtgg cacttttcgg ggaaatgtgc gcggaacccc   3660
tatttgttta tttttctaaa tacattcaaa tatgtatccg ctcatgagac aataaccctg   3720
ataaatgctt caataatatt gaaaaaggaa gagtatgagt attcaacatt tccgtgtcgc   3780
ccttattccc ttttttgcgg cattttgcct tcctgttttt gctcacccag aaacgctggt   3840
gaaagtaaaa gatgctgaag atcagttggg tgcacgagtg ggttacatcg aactggatct   3900
caacagcggt aagatccttg agagttttcg ccccgaagaa cgttttccaa tgatgagcac   3960
ttttaaagtt ctgctatgtg gcgcggtatt atcccgtatt gacgccgggc aagagcaact   4020
cggtcgccgc atacactatt ctcagaatga cttggttgag tactcaccag tcacagaaaa   4080
gcatcttacg gatggcatga cagtaagaga attatgcagt gctgccataa ccatgagtga   4140
taacactgcg gccaacttac ttctgacaac gatcggagga ccgaaggagc taaccgcttt   4200
tttgcacaac atgggggatc atgtaactcg ccttgatcgt tgggaaccgg agctgaatga   4260
```

-continued

```
agccatacca aacgacgagc gtgacaccac gatgcctgta gcaatggcaa caacgttgcg   4320

caaactatta actggcgaac tacttactct agcttcccgg caacaattaa tagactggat   4380

ggaggcggat aaagttgcag gaccacttct gcgctcggcc cttccggctg gctggtttat   4440

tgctgataaa tctggagccg gtgagcgtgg gtctcgcggt atcattgcag cactggggcc   4500

agatggtaag ccctcccgta tcgtagttat ctacacgacg gggagtcagg caactatgga   4560

tgaacgaaat agacagatcg ctgagatagg tgcctcactg attaagcatt ggtaactgtc   4620

agaccaagtt tactcatata tactttagat tgatttaaaa cttcattttt aatttaaaag   4680

gatctaggtg aagatccttt ttgataatct catgaccaaa atcccttaac gtgagttttc   4740

gttccactga gcgtcagacc ccgtagaaaa gatcaaagga tcttcttgag atcctttttt   4800

tctgcgcgta atctgctgct tgcaaacaaa aaaaccaccg ctaccagcgg tggtttgttt   4860

gccggatcaa gagctaccaa ctctttttcc gaaggtaact ggcttcagca gagcgcagat   4920

accaaatact gtccttctag tgtagccgta gttaggccac cacttcaaga actctgtagc   4980

accgcctaca tacctcgctc tgctaatcct gttaccagtg gctgctgcca gtggcgataa   5040

gtcgtgtctt accgggttgg actcaagacg atagttaccg gataaggcgc agcggtcggg   5100

ctgaacgggg ggttcgtgca cacagcccag cttggagcga acgacctaca ccgaactgag   5160

atacctacag cgtgagctat gagaaagcgc cacgcttccc gaagggagaa aggcggacag   5220

gtatccggta agcggcaggg tcggaacagg agagcgcacg agggagcttc caggggggaaa  5280

cgcctggtat ctttatagtc ctgtcgggtt tcgccacctc tgacttgagc gtcgattttt   5340

gtgatgctcg tcaggggggc ggagcctatg gaaaaacgcc agcaacgcgg cctttttacg   5400

gttcctggcc ttttgctggc cttttgctca catgttcttt cctgcgttat cccctgattc   5460

tgtggataac cgtattaccg cctttgagtg agctgatacc gctcgccgca gccgaacgac   5520

cgagcgcagc gagtcagtga gcgaggaagc ggaaga                             5556


<210> SEQ ID NO 3
<211> LENGTH: 3383
<212> TYPE: DNA
<213> ORGANISM: Artificial Sequence
<220> FEATURE:
<223> OTHER INFORMATION: plasmid
<220> FEATURE:
<221> NAME/KEY: gene
<222> LOCATION: (231)..(960)
<223> OTHER INFORMATION: deoD

<400> SEQUENCE: 3

gcgcccaata cgcaaaccgc ctctccccgc gcgttggccg attcattaat gcagctggca     60

cgacaggttt cccgactgga aagcgggcag tgagcgcaac gcaattaatg tgagttagct    120

cactcattag gcaccccagg ctttacactt tatgcttccg gctcgtatgt tgtgtggaat    180

tgtgagcgga taacaatttc acacaggaaa cagctatgac catgattacg aattcttcca    240

tggctacccc acacattaat gcagaaatgg gcgatttcgc tgacgtagtt ttgatgccag    300

gcgacccgct gcgtgcgaag tatattgctg aaactttcct tgaagatgcc cgtgaagtga    360

acaacgttcg cggtatgctg ggcttcaccg gtacttacaa aggccgcaaa atttccgtaa    420

tgggtcacgg tatgggtatc ccgtcctgct ccatctacac caaagaactg atcaccgatt    480

tcggcgtgaa gaaaattatc cgcgtgggtt cctgtggcgc agttctgccg cacgtaaaac    540

tgcgcgacgt cgttatcggt atgggtgcct gcaccgattc caaagttaac cgcatccgtt    600

ttaaagacca tgactttgcc gctatcgctg acttcgacat ggtgcgtaac gcagtagatg    660
```

-continued

```
cagctaaagc actgggtatt gatgctcgcg tgggtaacct gttctccgct gacctgttct    720
actctccgga cggcgaaatg ttcgacgtga tggaaaaata cggcattctc ggcgtggaaa    780
tggaagcggc tggtatctac ggcgtcgctg cagaatttgg cgcgaaagcc ctgaccatct    840
gcaccgtatc tgaccacatc cgcactcacg agcagaccac tgccgctgag cgtcagacta    900
ccttcaacga catgatcaaa atcgcactgg aatccgttct gctgggcgat aaagagtaag    960
tcgacctgca ggcatgcaag cttggcactg gccgtcgttt tacaacgtcg tgactgggaa   1020
aaccctggcg ttacccaact taatcgcctt gcagcacatc ccccttcgc cagctggcgt    1080
aatagcgaag aggcccgcac cgatcgccct tcccaacagt tgcgcagcct gaatggcgaa   1140
tggcgcctga tgcggtattt tctccttacg catctgtgcg gtatttcaca ccgcatatgg   1200
tgcactctca gtacaatctg ctctgatgcc gcatagttaa gccagccccg acacccgcca   1260
acacccgctg acgcgccctg acgggcttgt ctgctcccgg catccgctta cagacaagct   1320
gtgaccgtct ccgggagctg catgtgtcag aggttttcac cgtcatcacc gaaacgcgcg   1380
agacgaaagg gcctcgtgat acgcctattt ttataggtta atgtcatgat aataatggtt   1440
tcttagacgt caggtggcac ttttcgggga aatgtgcgcg gaacccctat ttgtttattt   1500
ttctaaatac attcaaatat gtatccgctc atgagacaat aaccctgata aatgcttcaa   1560
taatattgaa aaaggaagag tatgagtatt caacatttcc gtgtcgccct tattcccttt   1620
tttgcggcat tttgccttcc tgtttttgct cacccagaaa cgctggtgaa agtaaaagat   1680
gctgaagatc agttgggtgc acgagtgggt tacatcgaac tggatctcaa cagcggtaag   1740
atccttgaga gttttcgccc cgaagaacgt tttccaatga tgagcacttt taaagttctg   1800
ctatgtggcg cggtattatc ccgtattgac gccgggcaag agcaactcgg tcgccgcata   1860
cactattctc agaatgactt ggttgagtac tcaccagtca cagaaaagca tcttacggat   1920
ggcatgacag taagagaatt atgcagtgct gccataacca tgagtgataa cactgcggcc   1980
aacttacttc tgacaacgat cggaggaccg aaggagctaa ccgctttttt gcacaacatg   2040
ggggatcatg taactcgcct tgatcgttgg gaaccggagc tgaatgaagc cataccaaac   2100
gacgagcgtg acaccacgat gcctgtagca atggcaacaa cgttgcgcaa actattaact   2160
ggcgaactac ttactctagc ttcccggcaa caattaatag actggatgga ggcggataaa   2220
gttgcaggac cacttctgcg ctcggccctt ccggctggct ggtttattgc tgataaatct   2280
ggagccggtg agcgtgggtc tcgcggtatc attgcagcac tggggccaga tggtaagccc   2340
tcccgtatcg tagttatcta cacgacgggg agtcaggcaa ctatggatga acgaaataga   2400
cagatcgctg agataggtgc ctcactgatt aagcattggt aactgtcaga ccaagtttac   2460
tcatatatac tttagattga tttaaaactt catttttaat ttaaaaggat ctaggtgaag   2520
atcctttttg ataatctcat gaccaaaatc ccttaacgtg agttttcgtt ccactgagcg   2580
tcagaccccg tagaaaagat caaaggatct tcttgagatc ctttttttct gcgcgtaatc   2640
tgctgcttgc aaacaaaaaa accaccgcta ccagcggtgg tttgtttgcc ggatcaagag   2700
ctaccaactc tttttccgaa ggtaactggc ttcagcagag cgcagatacc aaatactgtc   2760
cttctagtgt agccgtagtt aggccaccac ttcaagaact ctgtagcacc gcctacatac   2820
ctcgctctgc taatcctgtt accagtggct gctgccagtg gcgataagtc gtgtcttacc   2880
gggttggact caagacgata gttaccggat aaggcgcagc ggtcgggctg aacggggggt   2940
tcgtgcacac agcccagctt ggagcgaacg acctacaccg aactgagata cctacagcgt   3000
gagctatgag aaagcgccac gcttcccgaa gggagaaagg cggacaggta tccggtaagc   3060
```

-continued

```
ggcagggtcg gaacaggaga gcgcacgagg gagcttccag gggaaacgc ctggtatctt   3120

tatagtcctg tcgggtttcg ccacctctga cttgagcgtc gatttttgtg atgctcgtca   3180

ggggggcgga gcctatggaa aaacgccagc aacgcggcct ttttacggtt cctggccttt   3240

tgctggcctt ttgctcacat gttctttcct gcgttatccc ctgattctgt ggataaccgt   3300

attaccgcct ttgagtgagc tgataccgct cgccgcagcc gaacgaccga gcgcagcgag   3360

tcagtgagcg aggaagcgga aga                                           3383
```

<210> SEQ ID NO 4
<211> LENGTH: 5495
<212> TYPE: DNA
<213> ORGANISM: Artificial Sequence
<220> FEATURE:
<223> OTHER INFORMATION: plasmid
<220> FEATURE:
<221> NAME/KEY: gene
<222> LOCATION: (231)..(960)
<223> OTHER INFORMATION: deoD
<220> FEATURE:
<221> NAME/KEY: gene
<222> LOCATION: (1423)..(2822)
<223> OTHER INFORMATION: tetracycline resistance

<400> SEQUENCE: 4

```
gcgcccaata cgcaaaccgc ctctccccgc gcgttggccg attcattaat gcagctggca     60

cgacaggttt cccgactgga aagcgggcag tgagcgcaac gcaattaatg tgagttagct    120

cactcattag gcaccccagg ctttacactt tatgcttccg gctcgtatgt tgtgtggaat    180

tgtgagcgga taacaatttc acacaggaaa cagctatgac catgattacg aattcttcca    240

tggctacccc acacattaat gcagaaatgg gcgatttcgc tgacgtagtt ttgatgccag    300

gcgacccgct gcgtgcgaag tatattgctg aaactttcct tgaagatgcc cgtgaagtga    360

acaacgttcg cggtatgctg ggcttcaccg gtacttacaa aggccgcaaa atttccgtaa    420

tgggtcacgg tatgggtatc ccgtcctgct ccatctacac caaagaactg atcaccgatt    480

tcggcgtgaa gaaaattatc cgcgtgggtt cctgtggcgc agttctgccg cacgtaaaac    540

tgcgcgacgt cgttatcggt atgggtgcct gcaccgattc caaagttaac cgcatccgtt    600

ttaaagacca tgactttgcc gctatcgctg acttcgacat ggtgcgtaac gcagtagatg    660

cagctaaagc actgggtatt gatgctcgcg tgggtaacct gttctccgct gacctgttct    720

actctccgga cggcgaaatg ttcgacgtga tggaaaaata cggcattctc ggcgtggaaa    780

tggaagcggc tggtatctac ggcgtcgctg cagaatttgg cgcgaaagcc ctgaccatct    840

gcaccgtatc tgaccacatc cgcactcacg agcagaccac tgccgctgag cgtcagacta    900

ccttcaacga catgatcaaa atcgcactgg aatccgttct gctgggcgat aaagagtaag    960

tcgacctgca ggcatgcaag ctttatgctt gtaaaccgtt ttgtgaaaaa atttttaaaa   1020

taaaaaaggg gacctctagg gtccccaatt aattagtaat ataatctatt aaaggtcatt   1080

caaaaggtca tccaccggat cagcttagta aagccctcgc tagattttaa tgcggatgtt   1140

gcgattactt cgccaactat tgcgataaca agaaaaagcc agcctttcat gatatatctc   1200

ccaatttgtg tagggcttat tatgcacgct taaaaataat aaaagcagac ttgacctgat   1260

agtttggctg tgagcaatta tgtgcttagt gcatctaacg cttgagttaa gccgcgccgc   1320

gaagcggcgt cggcttgaac gaattgttag acattatttg ccgactacct tggtgatctc   1380

gcctttcacg tagtggacaa attcttccaa ctgatctgcg cgccgagatg cgccgcgtgc   1440

ggctgctgga gatggcggac gcgatggata tgttctgcca agggttggtt tgcgcattca   1500
```

-continued

```
cagttctccg caagaattga ttggctccaa ttcttggagt ggtgaatccg ttagcgaggt   1560
gccgccggct tccattcagg tcgaggtggc ccggctccat gcaccgcgac gcaacgcggg   1620
gaggcagaca aggtataggg cggcgcctac aatccatgcc aacccgttcc atgtgctcgc   1680
cgaggcggca taaatcgccg tgacgatcag cggtccagtg atcgaagtta ggctggtaag   1740
agccgcgagc gatccttgaa gctgtccctg atggtcgtca tctacctgcc tggacagcat   1800
ggcctgcaac gcgggcatcc cgatgccgcc ggaagcgaga agaatcataa tggggaaggc   1860
catccagcct cgcgtcgcga acgccagcaa gacgtagccc agcgcgtcgg ccgccatgcc   1920
ggcgataatg gcctgcttct cgccgaaacg tttggtggcg ggaccagtga cgaaggcttg   1980
agcgagggcg tgcaagattc cgaataccgc aagcgacagg ccgatcatcg tcgcgctcca   2040
gcgaaagcgg tcctcgccga aaatgaccca gagcgctgcc ggcacctgtc ctacgagttg   2100
catgataaag aagacagtca taagtgcggc gacgatagtc atgccccgcg cccaccggaa   2160
ggagctgact gggttgaagg ctctcaaggg catcggtcga cgctctccct tatgcgactc   2220
ctgcattagg aagcagccca gtagtaggtt gaggccgttg agcaccgccg ccgcaaggaa   2280
tggtgcatgc aaggagatgg cgcccaacag tcccccggcc acggggcctg ccaccatacc   2340
cacgccgaaa caagcgctca tgagcccgaa gtggcgagcc cgatcttccc catcggtgat   2400
gtcggcgata taggcgccag caaccgcacc tgtggcgccg gtgatgccgg ccacgatgcg   2460
tccggcgtag aggatccaca ggacgggtgt ggtcgccatg atcgcgtagt cgatagtggc   2520
tccaagtagc gaagcgagca ggactgggcg gcggccaaag cggtcggaca gtgctccgag   2580
aacgggtgcg catagaaatt gcatcaacgc atatagcgct agcagcacgc catagtgact   2640
ggcgatgctg tcggaatgga cgatatcccg caagaggccc ggcagtaccg gcataaccaa   2700
gcctatgcct acagcatcca gggtgacggt gccgaggatg acgatgagcg cattgttaga   2760
tttcatacac ggtgcctgac tgcgttagca atttaactgt gataaactac cgcattaaag   2820
ctcatgcgga tcagtgaggg tttgcaactg cgggtcaagg atctggattt cgatcacggc   2880
acgatcatcg tgcgggaggg caagggctcc aaggatcggg ccttgatgtt acccgagagc   2940
ttggcaccca gcctgcgcga gcaggggaat tgatccggtg gatgaccttt tgaatgacct   3000
ttaatagatt atattactaa ttaattgggg accctagagg tcccctttttt tattttaaaa   3060
attttttcac aaaacggttt acaagcataa agcttggcac tggccgtcgt tttacaacgt   3120
cgtgactggg aaaaccctgg cgttacccaa cttaatcgcc ttgcagcaca tccccctttc   3180
gccagctggc gtaatagcga agaggcccgc accgatcgcc cttcccaaca gttgcgcagc   3240
ctgaatggcg aatggcgcct gatgcggtat tttctcctta cgcatctgtg cggtatttca   3300
caccgcatat ggtgcactct cagtacaatc tgctctgatg ccgcatagtt aagccagccc   3360
cgacacccgc caacacccgc tgacgcgccc tgacgggctt gtctgctccc ggcatccgct   3420
tacagacaag ctgtgaccgt ctccgggagc tgcatgtgtc agaggttttc accgtcatca   3480
ccgaaacgcg cgagacgaaa gggcctcgtg atacgcctat ttttataggt taatgtcatg   3540
ataataatgg tttcttagac gtcaggtggc acttttcggg gaaatgtgcg cggaacccct   3600
atttgtttat ttttctaaat acattcaaat atgtatccgc tcatgagaca ataaccctga   3660
taaatgcttc aataatattg aaaaaggaag agtatgagta ttcaacattt ccgtgtcgcc   3720
cttattccct tttttgcggc attttgcctt cctgtttttg ctcacccaga aacgctggtg   3780
aaagtaaaag atgctgaaga tcagttgggt gcacgagtgg gttacatcga actggatctc   3840
aacagcggta agatccttga gagttttcgc cccgaagaac gttttccaat gatgagcact   3900
```

-continued

```
tttaaagttc tgctatgtgg cgcggtatta tcccgtattg acgccgggca agagcaactc   3960

ggtcgccgca tacactattc tcagaatgac ttggttgagt actcaccagt cacagaaaag   4020

catcttacgg atggcatgac agtaagagaa ttatgcagtg ctgccataac catgagtgat   4080

aacactgcgg ccaacttact tctgacaacg atcggaggac cgaaggagct aaccgctttt   4140

ttgcacaaca tgggggatca tgtaactcgc cttgatcgtt gggaaccgga gctgaatgaa   4200

gccataccaa acgacgagcg tgacaccacg atgcctgtag caatggcaac aacgttgcgc   4260

aaactattaa ctggcgaact acttactcta gcttcccggc aacaattaat agactggatg   4320

gaggcggata aagttgcagg accacttctg cgctcggccc ttccggctgg ctggtttatt   4380

gctgataaat ctggagccgg tgagcgtggg tctcgcggta tcattgcagc actggggcca   4440

gatggtaagc cctcccgtat cgtagttatc tacacgacgg ggagtcaggc aactatggat   4500

gaacgaaata gacagatcgc tgagataggt gcctcactga ttaagcattg gtaactgtca   4560

gaccaagttt actcatatat actttagatt gatttaaaac ttcattttta atttaaaagg   4620

atctaggtga agatcctttt tgataatctc atgaccaaaa tcccttaacg tgagttttcg   4680

ttccactgag cgtcagaccc cgtagaaaag atcaaaggat cttcttgaga tccttttttt   4740

ctgcgcgtaa tctgctgctt gcaaacaaaa aaaccaccgc taccagcggt ggtttgtttg   4800

ccggatcaag agctaccaac tctttttccg aaggtaactg gcttcagcag agcgcagata   4860

ccaaatactg tccttctagt gtagccgtag ttaggccacc acttcaagaa ctctgtagca   4920

ccgcctacat acctcgctct gctaatcctg ttaccagtgg ctgctgccag tggcgataag   4980

tcgtgtctta ccgggttgga ctcaagacga tagttaccgg ataaggcgca gcggtcgggc   5040

tgaacggggg gttcgtgcac acagcccagc ttggagcgaa cgacctacac cgaactgaga   5100

tacctacagc gtgagctatg agaaagcgcc acgcttcccg aagggagaaa ggcggacagg   5160

tatccggtaa gcggcagggt cggaacagga gagcgcacga gggagcttcc agggggaaac   5220

gcctggtatc tttatagtcc tgtcgggttt cgccacctct gacttgagcg tcgatttttg   5280

tgatgctcgt caggggggcg gagcctatgg aaaaacgcca gcaacgcggc ctttttacgg   5340

ttcctggcct tttgctggcc ttttgctcac atgttctttc ctgcgttatc ccctgattct   5400

gtggataacc gtattaccgc ctttgagtga gctgataccg ctcgccgcag ccgaacgacc   5460

gagcgcagcg agtcagtgag cgaggaagcg gaaga                              5495
```

<210> SEQ ID NO 5
<211> LENGTH: 4189
<212> TYPE: DNA
<213> ORGANISM: Artificial Sequence
<220> FEATURE:
<223> OTHER INFORMATION: plasmid
<220> FEATURE:
<221> NAME/KEY: gene
<222> LOCATION: (243)..(1021)
<223> OTHER INFORMATION: udp
<220> FEATURE:
<221> NAME/KEY: gene
<222> LOCATION: (1037)..(1766)
<223> OTHER INFORMATION: deoD

<400> SEQUENCE: 5

```
gcgcccaata cgcaaaccgc ctctccccgc gcgttggccg attcattaat gcagctggca     60

cgacaggttt cccgactgga aagcgggcag tgagcgcaac gcaattaatg tgagttagct    120

cactcattag gcaccccagg ctttacactt tatgcttccg gctcgtatgt tgtgtggaat    180

tgtgagcgga taacaatttc acacaggaaa cagctatgac catgattacg aattcgagct    240
```

-continued

```
cggtaccatc catgtccaag tctgatgttt ttcatctcgg cctcactaaa aacgatttac    300
aaggggctac gcttgccatc gtccctggcg acccggatcg tgtggaaaag atcgccgcgc    360
tgatggataa gccggttaag ctggcatctc accgcgaatt cactacctgg cgtgcagagc    420
tggatggtaa acctgttatc gtctgctcta ccggtatcgg cggcccgtct acctctattg    480
ctgttgaaga gctggcacag ctgggcattc gcaccttcct gcgtatcggt acaacgggcg    540
ctattcagcc gcatattaat gtgggtgatg tcctggttac cacggcgtct gtccgtctgg    600
atggcgcgag cctgcacttc gcaccgctgg aattcccggc tgtcgctgat ttcgaatgta    660
cgactgcgct ggttgaagct gcgaaatcca ttggcgcgac aactcacgtt ggcgtgacag    720
cttcttctga taccttctac ccaggtcagg aacgttacga tacttactct ggtcgcgtag    780
ttcgtcactt taaaggttct atggaagagt ggcaggcgat gggcgtaatg aactatgaaa    840
tggaatctgc aaccctgctg accatgtgtg caagtcaggg cctgcgtgcc ggtatggtag    900
cgggtgttat cgttaaccgc acccagcaag agatcccgaa tgctgagacg atgaaacaaa    960
ccgaaagcca tgcggtgaaa atcgtggtgg aagcggcgcg tcgtctgctg taattctctt   1020
gtcgactagc aggaggaatt cttccatggc taccccacac attaatgcag aaatgggcga   1080
tttcgctgac gtagttttga tgccaggcga cccgctgcgt gcgaagtata ttgctgaaac   1140
tttccttgaa gatgcccgtg aagtgaacaa cgttcgcggt atgctgggct tcaccggtac   1200
ttacaaaggc cgcaaaattt ccgtaatggg tcacggtatg ggtatcccgt cctgctccat   1260
ctacaccaaa gaactgatca ccgatttcgg cgtgaagaaa attatccgcg tgggttcctg   1320
tggcgcagtt ctgccgcacg taaaactgcg cgacgtcgtt atcggtatgg gtgcctgcac   1380
cgattccaaa gttaaccgca tccgttttaa agaccatgac tttgccgcta tcgctgactt   1440
cgacatggtg cgtaacgcag tagatgcagc taaagcactg ggtattgatg ctcgcgtggg   1500
taacctgttc tccgctgacc tgttctactc tccggacggc gaaatgttcg acgtgatgga   1560
aaaatacggc attctcggcg tggaaatgga agcggctggt atctacggcg tcgctgcaga   1620
atttggcgcg aaagccctga ccatctgcac cgtatctgac cacatccgca ctcacgagca   1680
gaccactgcc gctgagcgtc agactacctt caacgacatg atcaaaatcg cactggaatc   1740
cgttctgctg ggcgataaag agtaagtcga cctgcaggca tgcaagcttg gcactggccg   1800
tcgttttaca acgtcgtgac tgggaaaacc ctggcgttac ccaacttaat cgccttgcag   1860
cacatccccc tttcgccagc tggcgtaata gcgaagaggc ccgcaccgat cgcccttccc   1920
aacagttgcg cagcctgaat ggcgaatggc gcctgatgcg gtattttctc cttacgcatc   1980
tgtgcggtat ttcacaccgc atatggtgca ctctcagtac aatctgctct gatgccgcat   2040
agttaagcca gccccgacac ccgccaacac ccgctgacgc gccctgacgg gcttgtctgc   2100
tcccggcatc cgcttacaga caagctgtga ccgtctccgg gagctgcatg tgtcagaggt   2160
tttcaccgtc atcaccgaaa cgcgcgagac gaaagggcct cgtgatacgc ctatttttat   2220
aggttaatgt catgataata atggtttctt agacgtcagg tggcactttt cggggaaatg   2280
tgcgcggaac ccctatttgt ttatttttct aaatacattc aaatatgtat ccgctcatga   2340
gacaataacc ctgataaatg cttcaataat attgaaaaag gaagagtatg agtattcaac   2400
atttccgtgt cgcccttatt cccttttttg cggcattttg ccttcctgtt tttgctcacc   2460
cagaaacgct ggtgaaagta aaagatgctg aagatcagtt gggtgcacga gtgggttaca   2520
tcgaactgga tctcaacagc ggtaagatcc ttgagagttt tcgccccgaa gaacgttttc   2580
caatgatgag cacttttaaa gttctgctat gtggcgcggt attatcccgt attgacgccg   2640
```

-continued

```
ggcaagagca actcggtcgc cgcatacact attctcagaa tgacttggtt gagtactcac   2700

cagtcacaga aaagcatctt acggatggca tgacagtaag agaattatgc agtgctgcca   2760

taaccatgag tgataacact gcggccaact tacttctgac aacgatcgga ggaccgaagg   2820

agctaaccgc ttttttgcac aacatggggg atcatgtaac tcgccttgat cgttgggaac   2880

cggagctgaa tgaagccata ccaaacgacg agcgtgacac cacgatgcct gtagcaatgg   2940

caacaacgtt gcgcaaacta ttaactggcg aactacttac tctagcttcc cggcaacaat   3000

taatagactg gatggaggcg gataaagttg caggaccact tctgcgctcg gcccttccgg   3060

ctggctggtt tattgctgat aaatctggag ccggtgagcg tgggtctcgc ggtatcattg   3120

cagcactggg gccagatggt aagccctccc gtatcgtagt tatctacacg acggggagtc   3180

aggcaactat ggatgaacga aatagacaga tcgctgagat aggtgcctca ctgattaagc   3240

attggtaact gtcagaccaa gtttactcat atatacttta gattgattta aaacttcatt   3300

tttaatttaa aaggatctag gtgaagatcc tttttgataa tctcatgacc aaaatccctt   3360

aacgtgagtt ttcgttccac tgagcgtcag accccgtaga aaagatcaaa ggatcttctt   3420

gagatccttt ttttctgcgc gtaatctgct gcttgcaaac aaaaaaacca ccgctaccag   3480

cggtggtttg tttgccggat caagagctac caactctttt tccgaaggta actggcttca   3540

gcagagcgca gataccaaat actgtccttc tagtgtagcc gtagttaggc caccacttca   3600

agaactctgt agcaccgcct acatacctcg ctctgctaat cctgttacca gtggctgctg   3660

ccagtggcga taagtcgtgt cttaccgggt tggactcaag acgatagtta ccggataagg   3720

cgcagcggtc gggctgaacg gggggttcgt gcacacagcc cagcttggag cgaacgacct   3780

acaccgaact gagataccta cagcgtgagc tatgagaaag cgccacgctt cccgaaggga   3840

gaaaggcgga caggtatccg gtaagcggca gggtcggaac aggagagcgc acgagggagc   3900

ttccaggggg aaacgcctgg tatctttata gtcctgtcgg gtttcgccac ctctgacttg   3960

agcgtcgatt tttgtgatgc tcgtcagggg ggcggagcct atggaaaaac gccagcaacg   4020

cggccttttt acggttcctg gccttttgct ggccttttgc tcacatgttc tttcctgcgt   4080

tatcccctga ttctgtggat aaccgtatta ccgcctttga gtgagctgat accgctcgcc   4140

gcagccgaac gaccgagcgc agcgagtcag tgagcgagga agcggaaga              4189


<210> SEQ ID NO 6
<211> LENGTH: 6301
<212> TYPE: DNA
<213> ORGANISM: Artificial Sequence
<220> FEATURE:
<223> OTHER INFORMATION: plasmid
<220> FEATURE:
<221> NAME/KEY: gene
<222> LOCATION: (243)..(1021)
<223> OTHER INFORMATION: udp
<220> FEATURE:
<221> NAME/KEY: gene
<222> LOCATION: (1037)..(1766)
<223> OTHER INFORMATION: deoD
<220> FEATURE:
<221> NAME/KEY: gene
<222> LOCATION: (2229)..(3628)
<223> OTHER INFORMATION: tetracycline resistance

<400> SEQUENCE: 6

gcgcccaata cgcaaaccgc ctctccccgc gcgttggccg attcattaat gcagctggca     60

cgacaggttt cccgactgga aagcgggcag tgagcgcaac gcaattaatg tgagttagct    120

cactcattag gcaccccagg ctttacactt tatgcttccg gctcgtatgt tgtgtggaat    180
```

-continued

```
tgtgagcgga taacaatttc acacaggaaa cagctatgac catgattacg aattcgagct    240
cggtaccatc catgtccaag tctgatgttt ttcatctcgg cctcactaaa aacgatttac    300
aaggggctac gcttgccatc gtccctggcg acccggatcg tgtggaaaag atcgccgcgc    360
tgatggataa gccggttaag ctggcatctc accgcgaatt cactacctgg cgtgcagagc    420
tggatggtaa acctgttatc gtctgctcta ccggtatcgg cggcccgtct acctctattg    480
ctgttgaaga gctggcacag ctgggcattc gcaccttcct gcgtatcggt acaacgggcg    540
ctattcagcc gcatattaat gtgggtgatg tcctggttac cacggcgtct gtccgtctgg    600
atggcgcgag cctgcacttc gcaccgctgg aattcccggc tgtcgctgat ttcgaatgta    660
cgactgcgct ggttgaagct gcgaaatcca ttggcgcgac aactcacgtt ggcgtgacag    720
cttcttctga taccttctac ccaggtcagg aacgttacga tacttactct ggtcgcgtag    780
ttcgtcactt taaaggttct atggaagagt ggcaggcgat gggcgtaatg aactatgaaa    840
tggaatctgc aaccctgctg accatgtgtg caagtcaggg cctgcgtgcc ggtatggtag    900
cgggtgttat cgttaaccgc acccagcaag agatcccgaa tgctgagacg atgaaacaaa    960
ccgaaagcca tgcggtgaaa atcgtggtgg aagcggcgcg tcgtctgctg taattctctt   1020
gtcgactagc aggaggaatt cttccatggc taccccacac attaatgcag aaatgggcga   1080
tttcgctgac gtagttttga tgccaggcga cccgctgcgt gcgaagtata ttgctgaaac   1140
tttccttgaa gatgcccgtg aagtgaacaa cgttcgcggt atgctgggct tcaccggtac   1200
ttacaaaggc cgcaaaattt ccgtaatggg tcacggtatg ggtatcccgt cctgctccat   1260
ctacaccaaa gaactgatca ccgatttcgg cgtgaagaaa attatccgcg tgggttcctg   1320
tggcgcagtt ctgccgcacg taaaactgcg cgacgtcgtt atcggtatgg gtgcctgcac   1380
cgattccaaa gttaaccgca tccgttttaa agaccatgac tttgccgcta tcgctgactt   1440
cgacatggtg cgtaacgcag tagatgcagc taaagcactg ggtattgatg ctcgcgtggg   1500
taacctgttc tccgctgacc tgttctactc tccggacggc gaaatgttcg acgtgatgga   1560
aaaatacggc attctcggcg tggaaatgga agcggctggt atctacggcg tcgctgcaga   1620
atttggcgcg aaagccctga ccatctgcac cgtatctgac cacatccgca ctcacgagca   1680
gaccactgcc gctgagcgtc agactacctt caacgacatg atcaaaatcg cactggaatc   1740
cgttctgctg ggcgataaag agtaagtcga cctgcaggca tgcaagcttt atgcttgtaa   1800
accgttttgt gaaaaaattt ttaaaataaa aaaggggacc tctagggtcc ccaattaatt   1860
agtaatataa tctattaaag gtcattcaaa aggtcatcca ccggatcagc ttagtaaagc   1920
cctcgctaga ttttaatgcg gatgttgcga ttacttcgcc aactattgcg ataacaagaa   1980
aaagccagcc tttcatgata tatctcccaa tttgtgtagg gcttattatg cacgcttaaa   2040
aataataaaa gcagacttga cctgatagtt tggctgtgag caattatgtg cttagtgcat   2100
ctaacgcttg agttaagccg cgccgcgaag cggcgtcggc ttgaacgaat tgttagacat   2160
tatttgccga ctaccttggt gatctcgcct ttcacgtagt ggacaaattc ttccaactga   2220
tctgcgcgcc gagatgcgcc gcgtgcggct gctggagatg gcggacgcga tggatatgtt   2280
ctgccaaggg ttggtttgcg cattcacagt tctccgcaag aattgattgg ctccaattct   2340
tggagtggtg aatccgttag cgaggtgccg ccggcttcca ttcaggtcga ggtggcccgg   2400
ctccatgcac cgcgacgcaa cgcggggagg cagacaaggt atagggcggc gcctacaatc   2460
catgccaacc cgttccatgt gctcgccgag gcggcataaa tcgccgtgac gatcagcggt   2520
ccagtgatcg aagttaggct ggtaagagcc gcgagcgatc cttgaagctg tccctgatgg   2580
```

-continued

```
tcgtcatcta cctgcctgga cagcatggcc tgcaacgcgg gcatcccgat gccgccggaa   2640
gcgagaagaa tcataatggg gaaggccatc cagcctcgcg tcgcgaacgc cagcaagacg   2700
tagcccagcg cgtcggccgc catgccggcg ataatggcct gcttctcgcc gaaacgtttg   2760
gtggcgggac cagtgacgaa ggcttgagcg agggcgtgca agattccgaa taccgcaagc   2820
gacaggccga tcatcgtcgc gctccagcga aagcggtcct cgccgaaaat gacccagagc   2880
gctgccggca cctgtcctac gagttgcatg ataaagaaga cagtcataag tgcggcgacg   2940
atagtcatgc cccgcgccca ccggaaggag ctgactgggt tgaaggctct caagggcatc   3000
ggtcgacgct ctcccttatg cgactcctgc attaggaagc agcccagtag taggttgagg   3060
ccgttgagca ccgccgccgc aaggaatggt gcatgcaagg agatggcgcc caacagtccc   3120
ccggccacgg ggcctgccac catacccacg ccgaaacaag cgctcatgag cccgaagtgg   3180
cgagcccgat cttccccatc ggtgatgtcg gcgatatagg cgccagcaac cgcacctgtg   3240
gcgccggtga tgccggccac gatgcgtccg gcgtagagga tccacaggac gggtgtggtc   3300
gccatgatcg cgtagtcgat agtggctcca agtagcgaag cgagcaggac tgggcggcgg   3360
ccaaagcggt cggacagtgc tccgagaacg ggtgcgcata gaaattgcat caacgcatat   3420
agcgctagca gcacgccata gtgactggcg atgctgtcgg aatggacgat atcccgcaag   3480
aggcccggca gtaccggcat aaccaagcct atgcctacag catccagggt gacggtgccg   3540
aggatgacga tgagcgcatt gttagatttc atacacggtg cctgactgcg ttagcaattt   3600
aactgtgata aactaccgca ttaaagctca tgcggatcag tgagggtttg caactgcggg   3660
tcaaggatct ggatttcgat cacggcacga tcatcgtgcg ggagggcaag ggctccaagg   3720
atcgggcctt gatgttaccc gagagcttgg cacccagcct gcgcgagcag gggaattgat   3780
ccggtggatg accttttgaa tgacctttaa tagattatat tactaattaa ttggggaccc   3840
tagaggtccc ctttttttatt ttaaaaattt tttcacaaaa cggtttacaa gcataaagct   3900
tggcactggc cgtcgtttta caacgtcgtg actgggaaaa ccctggcgtt acccaactta   3960
atcgccttgc agcacatccc cctttcgcca gctggcgtaa tagcgaagag gcccgcaccg   4020
atcgcccttc ccaacagttg cgcagcctga atggcgaatg gcgcctgatg cggtattttc   4080
tccttacgca tctgtgcggt atttcacacc gcatatggtg cactctcagt acaatctgct   4140
ctgatgccgc atagttaagc cagccccgac acccgccaac acccgctgac gcgccctgac   4200
gggcttgtct gctcccggca tccgcttaca gacaagctgt gaccgtctcc gggagctgca   4260
tgtgtcagag gttttcaccg tcatcaccga aacgcgcgag acgaaagggc ctcgtgatac   4320
gcctattttt ataggttaat gtcatgataa taatggtttc ttagacgtca ggtggcactt   4380
ttcggggaaa tgtgcgcgga acccctattt gtttattttt ctaaatacat tcaaatatgt   4440
atccgctcat gagacaataa ccctgataaa tgcttcaata atattgaaaa aggaagagta   4500
tgagtattca acatttccgt gtcgccctta ttcccttttt tgcggcattt tgccttcctg   4560
tttttgctca cccagaaacg ctggtgaaag taaaagatgc tgaagatcag ttgggtgcac   4620
gagtgggtta catcgaactg gatctcaaca gcggtaagat ccttgagagt tttcgccccg   4680
aagaacgttt tccaatgatg agcactttta aagttctgct atgtggcgcg gtattatccc   4740
gtattgacgc cgggcaagag caactcggtc gccgcataca ctattctcag aatgacttgg   4800
ttgagtactc accagtcaca gaaaagcatc ttacggatgg catgacagta agagaattat   4860
gcagtgctgc cataaccatg agtgataaca ctgcggccaa cttacttctg acaacgatcg   4920
gaggaccgaa ggagctaacc gcttttttgc acaacatggg ggatcatgta actcgccttg   4980
```

-continued atcgttggga accggagctg aatgaagcca taccaaacga cgagcgtgac accacgatgc 5040
ctgtagcaat ggcaacaacg ttgcgcaaac tattaactgg cgaactactt actctagctt 5100
cccggcaaca attaatagac tggatggagg cggataaagt tgcaggacca cttctgcgct 5160
cggcccttcc ggctggctgg tttattgctg ataaatctgg agccggtgag cgtgggtctc 5220
gcggtatcat tgcagcactg gggccagatg gtaagccctc ccgtatcgta gttatctaca 5280
cgacggggag tcaggcaact atggatgaac gaaatagaca gatcgctgag ataggtgcct 5340
cactgattaa gcattggtaa ctgtcagacc aagtttactc atatatactt tagattgatt 5400
taaaacttca tttttaattt aaaaggatct aggtgaagat cctttttgat aatctcatga 5460
ccaaaatccc ttaacgtgag ttttcgttcc actgagcgtc agaccccgta gaaaagatca 5520
aaggatcttc ttgagatcct ttttttctgc gcgtaatctg ctgcttgcaa acaaaaaaac 5580
caccgctacc agcggtggtt tgtttgccgg atcaagagct accaactctt tttccgaagg 5640
taactggctt cagcagagcg cagataccaa atactgtcct tctagtgtag ccgtagttag 5700
gccaccactt caagaactct gtagcaccgc ctacatacct cgctctgcta atcctgttac 5760
cagtggctgc tgccagtggc gataagtcgt gtcttaccgg gttggactca agacgatagt 5820
taccggataa ggcgcagcgg tcgggctgaa cggggggttc gtgcacacag cccagcttgg 5880
agcgaacgac ctacaccgaa ctgagatacc tacagcgtga gctatgagaa agcgccacgc 5940
ttcccgaagg gagaaaggcg gacaggtatc cggtaagcgg cagggtcgga acaggagagc 6000
gcacgaggga gcttccaggg ggaaacgcct ggtatcttta tagtcctgtc gggtttcgcc 6060
acctctgact tgagcgtcga tttttgtgat gctcgtcagg ggggcggagc ctatggaaaa 6120
acgccagcaa cgcggccttt ttacggttcc tggccttttg ctggcctttt gctcacatgt 6180
tctttcctgc gttatcccct gattctgtgg ataaccgtat taccgccttt gagtgagctg 6240
ataccgctcg ccgcagccga acgaccgagc gcagcgagtc agtgagcgag gaagcggaag 6300
a 6301

<210> SEQ ID NO 7
<211> LENGTH: 5241
<212> TYPE: DNA
<213> ORGANISM: Artificial Sequence
<220> FEATURE:
<223> OTHER INFORMATION: plasmid
<220> FEATURE:
<221> NAME/KEY: gene
<222> LOCATION: (1312)..(2042)
<223> OTHER INFORMATION: deoD

<400> SEQUENCE: 7
atcgatgcat aatgtgcctg tcaaatggac gaagcaggga ttctgcaaac cctatgctac 60
tccgtcaagc cgtcaattgt ctgattcgtt accaattatg acaacttgac ggctacatca 120
ttcacttttt cttcacaacc ggcacggaac tcgctcgggc tggccccggt gcattttta 180 aatacccgcg agaaatagag ttgatcgtca aaaccaacat tgcgaccgac ggtggcgata 240
ggcatccggg tggtgctcaa aagcagcttc gcctggctga tacgttggtc ctcgcgccag 300
cttaagacgc taatccctaa ctgctggcgg aaaagatgtg acagacgcga cggcgacaag 360
caaacatgct gtgcgacgct ggcgatatca aaattgctgt ctgccaggtg atcgctgatg 420
tactgacaag cctcgcgtac ccgattatcc atcggtggat ggagcgactc gttaatcgct 480
tccatgcgcc gcagtaacaa ttgctcaagc agatttatcg ccagcagctc cgaatagcgc 540
ccttcccctt gcccggcgtt aatgatttgc ccaaacaggt cgctgaaatg cggctggtgc 600

-continued

```
gcttcatccg ggcgaaagaa ccccgtattg gcaaatattg acggccagtt aagccattca    660
tgccagtagg cgcgcggacg aaagtaaacc cactggtgat accattcgcg agcctccgga    720
tgacgaccgt agtgatgaat ctctcctggc gggaacagca aaatatcacc cggtcggcaa    780
acaaattctc gtccctgatt tttcaccacc ccctgaccgc gaatggtgag attgagaata    840
taacctttca ttcccagcgg tcggtcgata aaaaaatcga gataaccgtt ggcctcaatc    900
ggcgttaaac ccgccaccag atgggcatta aacgagtatc ccggcagcag gggatcattt    960
tgcgcttcag ccatactttt catactcccg ccattcagag aagaaaccaa ttgtccatat   1020
tgcatcagac attgccgtca ctgcgtcttt tactggctct tctcgctaac caaaccggta   1080
accccgctta ttaaaagcat tctgtaacaa agcgggacca aagccatgac aaaaacgcgt   1140
aacaaaagtg tctataatca cggcagaaaa gtccacattg attatttgca cggcgtcaca   1200
ctttgctatg ccatagcatt tttatccata agattagcgg atcctacctg acgcttttta   1260
tcgcaactct ctactgtttc tccatacccg tttttttggg ctagcaggag ggaattcttc   1320
catggctacc ccacacatta atgcagaaat gggcgatttc gctgacgtag ttttgatgcc   1380
aggcgacccg ctgcgtgcga agtatattgc tgaaactttc cttgaagatg cccgtgaagt   1440
gaacaacgtt cgcggtatgc tgggcttcac cggtacttac aaaggccgca aaatttccgt   1500
aatgggtcac ggtatgggta tcccgtcctg ctccatctac accaaagaac tgatcaccga   1560
tttcggcgtg aagaaaatta tccgcgtggg ttcctgtggc gcagttctgc cgcacgtaaa   1620
actgcgcgac gtcgttatcg gtatgggtgc ctgcaccgat tccaaagtta accgcatccg   1680
ttttaaagac catgactttg ccgctatcgc tgacttcgac atggtgcgta acgcagtaga   1740
tgcagctaaa gcactgggta ttgatgctcg cgtgggtaac ctgttctccg ctgacctgtt   1800
ctactctccg gacggcgaaa tgttcgacgt gatggaaaaa tacggcattc tcggcgtgga   1860
aatggaagcg gctggtatct acggcgtcgc tgcagaattt ggcgcgaaag ccctgaccat   1920
ctgcaccgta tctgaccaca tccgcactca cgagcagacc actgccgctg agcgtcagac   1980
taccttcaac gacatgatca aaatcgcact ggaatccgtt ctgctgggcg ataaagagta   2040
agtcgacctg caggcatgca agcttggctg ttttggcgga tgagagaaga ttttcagcct   2100
gatacagatt aaatcagaac gcagaagcgg tctgataaaa cagaatttgc ctggcggcag   2160
tagcgcggtg gtcccacctg accccatgcc gaactcagaa gtgaaacgcc gtagcgccga   2220
tggtagtgtg gggtctcccc atgcgagagt agggaactgc caggcatcaa ataaaacgaa   2280
aggctcagtc gaaagactgg gcctttcgtt ttatctgttg tttgtcggtg aacgctctcc   2340
tgagtaggac aaatccgccg ggagcggatt tgaacgttgc gaagcaacgg cccggagggt   2400
ggcgggcagg acgcccgcca taaactgcca ggcatcaaat taagcagaag gccatcctga   2460
cggatggcct ttttgcgttt ctacaaactc ttttgtttat ttttctaaat acattcaaat   2520
atgtatccgc tcatgagaca ataaccctga taaatgcttc aataatattg aaaaaggaag   2580
agtatgagta ttcaacattt ccgtgtcgcc cttattccct tttttgcggc attttgcctt   2640
cctgtttttg ctcacccaga aacgctggtg aaagtaaaag atgctgaaga tcagttgggt   2700
gcacgagtgg gttacatcga actggatctc aacagcggta agatccttga gagttttcgc   2760
cccgaagaac gttttccaat gatgagcact tttaaagttc tgctatgtgg cgcggtatta   2820
tcccgtgttg acgccgggca agagcaactc ggtcgccgca tacactattc tcagaatgac   2880
ttggttgagt actcaccagt cacagaaaag catcttacgg atggcatgac agtaagagaa   2940
ttatgcagtg ctgccataac catgagtgat aacactgcgg ccaacttact tctgacaacg   3000
```

-continued

```
atcggaggac cgaaggagct aaccgctttt ttgcacaaca tgggggatca tgtaactcgc   3060
cttgatcgtt gggaaccgga gctgaatgaa gccataccaa acgacgagcg tgacaccacg   3120
atgcctgtag caatggcaac aacgttgcgc aaactattaa ctggcgaact acttactcta   3180
gcttcccggc aacaattaat agactggatg gaggcggata aagttgcagg accacttctg   3240
cgctcggccc ttccggctgg ctggtttatt gctgataaat ctggagccgg tgagcgtggg   3300
tctcgcggta tcattgcagc actggggcca gatggtaagc cctcccgtat cgtagttatc   3360
tacacgacgg ggagtcaggc aactatggat gaacgaaata gacagatcgc tgagataggt   3420
gcctcactga ttaagcattg gtaactgtca gaccaagttt actcatatat actttagatt   3480
gatttacgcg ccctgtagcg gcgcattaag cgcggcgggt gtggtggtta cgcgcagcgt   3540
gaccgctaca cttgccagcg ccctagcgcc cgctcctttc gctttcttcc cttcctttct   3600
cgccacgttc gccggctttc cccgtcaagc tctaaatcgg gggctccctt tagggttccg   3660
atttagtgct ttacggcacc tcgaccccaa aaaacttgat ttgggtgatg gttcacgtag   3720
tgggccatcg ccctgataga cggtttttcg ccctttgacg ttggagtcca cgttctttaa   3780
tagtggactc ttgttccaaa cttgaacaac actcaaccct atctcgggct attcttttga   3840
tttataaggg attttgccga tttcggccta ttggttaaaa aatgagctga tttaacaaaa   3900
atttaacgcg aattttaaca aaatattaac gtttacaatt taaaaggatc taggtgaaga   3960
tcctttttga taatctcatg accaaaatcc cttaacgtga gttttcgttc cactgagcgt   4020
cagaccccgt agaaaagatc aaaggatctt cttgagatcc tttttttctg cgcgtaatct   4080
gctgcttgca aacaaaaaaa ccaccgctac cagcggtggt ttgtttgccg gatcaagagc   4140
taccaactct ttttccgaag gtaactggct tcagcagagc gcagatacca aatactgtcc   4200
ttctagtgta gccgtagtta ggccaccact tcaagaactc tgtagcaccg cctacatacc   4260
tcgctctgct aatcctgtta ccagtggctg ctgccagtgg cgataagtcg tgtcttaccg   4320
ggttggactc aagacgatag ttaccggata aggcgcagcg gtcgggctga acggggggtt   4380
cgtgcacaca gcccagcttg gagcgaacga cctacaccga actgagatac ctacagcgtg   4440
agctatgaga aagcgccacg cttcccgaag ggagaaaggc ggacaggtat ccggtaagcg   4500
gcagggtcgg aacaggagag cgcacgaggg agcttccagg gggaaacgcc tggtatcttt   4560
atagtcctgt cgggtttcgc cacctctgac ttgagcgtcg atttttgtga tgctcgtcag   4620
gggggcggag cctatggaaa aacgccagca acgcggcctt tttacggttc ctggcctttt   4680
gctggccttt tgctcacatg ttctttcctg cgttatcccc tgattctgtg gataaccgta   4740
ttaccgcctt tgagtgagct gataccgctc gccgcagccg aacgaccgag cgcagcgagt   4800
cagtgagcga ggaagcggaa gagcgcctga tgcggtattt tctccttacg catctgtgcg   4860
gtatttcaca ccgcataggg tcatggctgc gccccgacac ccgccaacac ccgctgacgc   4920
gccctgacgg gcttgtctgc tcccggcatc cgcttacaga caagctgtga ccgtctccgg   4980
gagctgcatg tgtcagaggt tttcaccgtc atcaccgaaa cgcgcgaggc agcaaggaga   5040
tggcgcccaa cagtccccccg gccacggggc ctgccaccat acccacgccg aaacaagcgc   5100
tcatgagccc gaagtggcga gcccgatctt ccccatcggt gatgtcggcg atataggcgc   5160
cagcaaccgc acctgtggcg ccggtgatgc cggccacgat gcgtccggcg tagaggatct   5220
gctcatgttt gacagcttat c                                              5241
```

-continued

<210> SEQ ID NO 8
<211> LENGTH: 5822
<212> TYPE: DNA
<213> ORGANISM: Artificial Sequence
<220> FEATURE:
<223> OTHER INFORMATION: pGM716 with deletion of HpaI fragment

<400> SEQUENCE: 8
gcgcccaata cgcaaaccgc ctctccccgc gcgttggccg attcattaat gcagctggca 60
cgacaggttt cccgactgga aagcgggcag tgagcgcaac gcaattaatg tgagttagct 120
cactcattag gcaccccagg ctttacactt tatgcttccg gctcgtatgt tgtgtggaat 180
tgtgagcgga taacaatttc acacaggaaa cagctatgac catgattacg aattcgagct 240
cggtaccatc catgtccaag tctgatgttt ttcatctcgg cctcactaaa aacgatttac 300
aaggggctac gcttgccatc gtccctggcg acccggatcg tgtggaaaag atcgccgcgc 360
tgatggataa gccggttaag ctggcatctc accgcgaatt cactacctgg cgtgcagagc 420
tggatggtaa acctgttatc gtctgctcta ccggtatcgg cggcccgtct acctctattg 480
ctgttgaaga gctggcacag ctgggcattc gcaccttcct gcgtatcggt acaacgggcg 540
ctattcagcc gcatattaat gtgggtgatg tcctggttac cacggcgtct gtccgtctgg 600
atggcgcgag cctgcacttc gcaccgctgg aattccccggc tgtcgctgat ttcgaatgta 660
cgactgcgct ggttgaagct gcgaaatcca ttggcgcgac aactcacgtt ggcgtgacag 720
cttcttctga taccttctac ccaggtcagg aacgttacga tacttactct ggtcgcgtag 780
ttcgtcactt taaaggttct atggaagagt ggcaggcgat gggcgtaatg aactatgaaa 840
tggaatctgc aaccctgctg accatgtgtg caagtcaggg cctgcgtgcc ggtatggtag 900
cgggtgttat cgttaaccgc atccgtttta aagaccatga ctttgccgct atcgctgact 960
tcgacatggt gcgtaacgca gtagatgcag ctaaagcact gggtattgat gctcgcgtgg 1020
gtaacctgtt ctccgctgac ctgttctact ctccggacgg cgaaatgttc gacgtgatgg 1080
aaaaatacgg cattctcggc gtggaaatgg aagcggctgg tatctacggc gtcgctgcag 1140
aatttggcgc gaaagccctg accatctgca ccgtatctga ccacatccgc actcacgagc 1200
agaccactgc cgctgagcgt cagactacct tcaacgacat gatcaaaatc gcactggaat 1260
ccgttctgct gggcgataaa gagtaagtcg acctgcaggc atgcaagctt tatgcttgta 1320
aaccgttttg tgaaaaaatt tttaaaataa aaaaggggac ctctagggtc cccaattaat 1380
tagtaatata atctattaaa ggtcattcaa aaggtcatcc accggatcag cttagtaaag 1440
ccctcgctag attttaatgc ggatgttgcg attacttcgc caactattgc gataacaaga 1500
aaaagccagc ctttcatgat atatctccca atttgtgtag ggcttattat gcacgcttaa 1560
aaataataaa agcagacttg acctgatagt ttggctgtga gcaattatgt gcttagtgca 1620
tctaacgctt gagttaagcc gcgccgcgaa gcggcgtcgg cttgaacgaa ttgttagaca 1680
ttatttgccg actaccttgg tgatctcgcc tttcacgtag tggacaaatt cttccaactg 1740
atctgcgcgc cgagatgcgc cgcgtgcggc tgctggagat ggcggacgcg atggatatgt 1800
tctgccaagg gttggtttgc gcattcacag ttctccgcaa gaattgattg gctccaattc 1860
ttggagtggt gaatccgtta gcgaggtgcc gccggcttcc attcaggtcg aggtggcccg 1920
gctccatgca ccgcgacgca acgcggggag gcagacaagg tatagggcgg cgcctacaat 1980
ccatgccaac ccgttccatg tgctcgccga ggcggcataa atcgccgtga cgatcagcgg 2040
tccagtgatc gaagttaggc tggtaagagc cgcgagcgat ccttgaagct gtccctgatg 2100

-continued

```
gtcgtcatct acctgcctgg acagcatggc ctgcaacgcg ggcatcccga tgccgccgga   2160
agcgagaaga atcataatgg ggaaggccat ccagcctcgc gtcgcgaacg ccagcaagac   2220
gtagcccagc gcgtcggccg ccatgccggc gataatggcc tgcttctcgc cgaaacgttt   2280
ggtggcggga ccagtgacga aggcttgagc gagggcgtgc aagattccga ataccgcaag   2340
cgacaggccg atcatcgtcg cgctccagcg aaagcggtcc tcgccgaaaa tgacccagag   2400
cgctgccggc acctgtccta cgagttgcat gataaagaag acagtcataa gtgcggcgac   2460
gatagtcatg ccccgcgccc accggaagga gctgactggg ttgaaggctc tcaagggcat   2520
cggtcgacgc tctcccttat gcgactcctg cattaggaag cagcccagta gtaggttgag   2580
gccgttgagc accgccgccg caaggaatgg tgcatgcaag gagatggcgc ccaacagtcc   2640
cccggccacg gggcctgcca ccatacccac gccgaaacaa gcgctcatga gcccgaagtg   2700
gcgagcccga tcttccccat cggtgatgtc ggcgatatag gcgccagcaa ccgcacctgt   2760
ggcgccggtg atgccggcca cgatgcgtcc ggcgtagagg atccacagga cgggtgtggt   2820
cgccatgatc gcgtagtcga tagtggctcc aagtagcgaa gcgagcagga ctgggcggcg   2880
gccaaagcgg tcggacagtg ctccgagaac gggtgcgcat agaaattgca tcaacgcata   2940
tagcgctagc agcacgccat agtgactggc gatgctgtcg gaatggacga tatcccgcaa   3000
gaggcccggc agtaccggca taaccaagcc tatgcctaca gcatccaggg tgacggtgcc   3060
gaggatgacg atgagcgcat tgttagattt catacacggt gcctgactgc gttagcaatt   3120
taactgtgat aaactaccgc attaaagctc atgcggatca gtgagggttt gcaactgcgg   3180
gtcaaggatc tggatttcga tcacggcacg atcatcgtgc gggagggcaa gggctccaag   3240
gatcgggcct tgatgttacc cgagagcttg gcacccagcc tgcgcgagca ggggaattga   3300
tccggtggat gacctttga atgaccttta atagattata ttactaatta attggggacc   3360
ctagaggtcc ccttttttat tttaaaaatt ttttcacaaa acggtttaca agcataaagc   3420
ttggcactgg ccgtcgtttt acaacgtcgt gactgggaaa accctggcgt tacccaactt   3480
aatcgccttg cagcacatcc ccctttcgcc agctggcgta atagcgaaga ggcccgcacc   3540
gatcgccctt cccaacagtt gcgcagcctg aatggcgaat ggcgcctgat gcggtatttt   3600
ctccttacgc atctgtgcgg tatttcacac cgcatatggt gcactctcag tacaatctgc   3660
tctgatgccg catagttaag ccagccccga cacccgccaa cacccgctga cgcgccctga   3720
cgggcttgtc tgctcccggc atccgcttac agacaagctg tgaccgtctc cgggagctgc   3780
atgtgtcaga ggttttcacc gtcatcaccg aaacgcgcga gacgaaaggg cctcgtgata   3840
cgcctatttt tataggttaa tgtcatgata ataatggttt cttagacgtc aggtggcact   3900
tttcggggaa atgtgcgcgg aacccctatt tgtttatttt tctaaataca ttcaaatatg   3960
tatccgctca tgagacaata accctgataa atgcttcaat aatattgaaa aaggaagagt   4020
atgagtattc aacatttccg tgtcgccctt attccctttt ttgcggcatt ttgccttcct   4080
gtttttgctc acccagaaac gctggtgaaa gtaaaagatg ctgaagatca gttgggtgca   4140
cgagtgggtt acatcgaact ggatctcaac agcggtaaga tccttgagag ttttcgcccc   4200
gaagaacgtt ttccaatgat gagcactttt aaagttctgc tatgtggcgc ggtattatcc   4260
cgtattgacg ccgggcaaga gcaactcggt cgccgcatac actattctca gaatgacttg   4320
gttgagtact caccagtcac agaaaagcat cttacggatg gcatgacagt aagagaatta   4380
tgcagtgctg ccataaccat gagtgataac actgcggcca acttacttct gacaacgatc   4440
ggaggaccga aggagctaac cgcttttttg cacaacatgg gggatcatgt aactcgcctt   4500
```

-continued

```
gatcgttggg aaccggagct gaatgaagcc ataccaaacg acgagcgtga caccacgatg   4560

cctgtagcaa tggcaacaac gttgcgcaaa ctattaactg gcgaactact tactctagct   4620

tcccggcaac aattaataga ctggatggag gcggataaag ttgcaggacc acttctgcgc   4680

tcggcccttc cggctggctg gtttattgct gataaatctg gagccggtga gcgtgggtct   4740

cgcggtatca ttgcagcact ggggccagat ggtaagccct cccgtatcgt agttatctac   4800

acgacgggga gtcaggcaac tatggatgaa cgaaatagac agatcgctga gataggtgcc   4860

tcactgatta agcattggta actgtcagac caagtttact catatatact ttagattgat   4920

ttaaaacttc atttttaatt taaaaggatc taggtgaaga tcctttttga taatctcatg   4980

accaaaatcc cttaacgtga gttttcgttc cactgagcgt cagaccccgt agaaaagatc   5040

aaaggatctt cttgagatcc tttttttctg cgcgtaatct gctgcttgca aacaaaaaaa   5100

ccaccgctac cagcggtggt ttgtttgccg gatcaagagc taccaactct ttttccgaag   5160

gtaactggct tcagcagagc gcagatacca aatactgtcc ttctagtgta gccgtagtta   5220

ggccaccact tcaagaactc tgtagcaccg cctacatacc tcgctctgct aatcctgtta   5280

ccagtggctg ctgccagtgg cgataagtcg tgtcttaccg ggttggactc aagacgatag   5340

ttaccggata aggcgcagcg gtcgggctga acggggggtt cgtgcacaca gcccagcttg   5400

gagcgaacga cctacaccga actgagatac ctacagcgtg agctatgaga aagcgccacg   5460

cttcccgaag ggagaaaggc ggacaggtat ccggtaagcg gcagggtcgg aacaggagag   5520

cgcacgaggg agcttccagg gggaaacgcc tggtatcttt atagtcctgt cgggtttcgc   5580

cacctctgac ttgagcgtcg atttttgtga tgctcgtcag gggggcggag cctatggaaa   5640

aacgccagca acgcggcctt tttacggttc ctggcctttt gctggccttt tgctcacatg   5700

ttctttcctg cgttatcccc tgattctgtg gataaccgta ttaccgcctt tgagtgagct   5760

gataccgctc gccgcagccg aacgaccgag cgcagcgagt cagtgagcga ggaagcggaa   5820

ga                                                                  5822
```

<210> SEQ ID NO 9
<211> LENGTH: 6269
<212> TYPE: DNA
<213> ORGANISM: Artificial Sequence
<220> FEATURE:
<223> OTHER INFORMATION: udp and deoD cloned in pUC18 so to create a
fusion between the two proteins

<400> SEQUENCE: 9

```
gcgcccaata cgcaaaccgc ctctccccgc gcgttggccg attcattaat gcagctggca     60

cgacaggttt cccgactgga aagcgggcag tgagcgcaac gcaattaatg tgagttagct    120

cactcattag gcaccccagg ctttacactt tatgcttccg gctcgtatgt tgtgtggaat    180

tgtgagcgga taacaatttc acacaggaaa cagctatgac catgattacg aattcgagct    240

cggtaccatc catgtccaag tctgatgttt ttcatctcgg cctcactaaa aacgatttac    300

aaggggctac gcttgccatc gtccctggcg acccggatcg tgtggaaaag atcgccgcgc    360

tgatggataa gccggttaag ctggcatctc accgcgaatt cactacctgg cgtgcagagc    420

tggatggtaa acctgttatc gtctgctcta ccggtatcgg cggcccgtct acctctattg    480

ctgttgaaga gctggcacag ctgggcattc gcaccttcct gcgtatcggt acaacgggcg    540

ctattcagcc gcatattaat gtgggtgatg tcctggttac cacggcgtct gtccgtctgg    600

atggcgcgag cctgcacttc gcaccgctgg aattcccggc tgtcgctgat ttcgaatgta    660
```

-continued

```
cgactgcgct ggttgaagct gcgaaatcca ttggcgcgac aactcacgtt ggcgtgacag    720
cttcttctga taccttctac ccaggtcagg aacgttacga tacttactct ggtcgcgtag    780
ttcgtcactt taaaggttct atggaagagt ggcaggcgat gggcgtaatg aactatgaaa    840
tggaatctgc aaccctgctg accatgtgtg caagtcaggg cctgcgtgcc ggtatggtag    900
cgggtgttat cgttaaccgc acccagcaag agatcccgaa tgctgagacg atgaaacaaa    960
ccgaaagcca tgcggtgaaa atcgtggtgg aagcggcgcg tcgtctgctg tccatggcta   1020
ccccacacat taatgcagaa atgggcgatt tcgctgacgt agttttgatg ccaggcgacc   1080
cgctgcgtgc gaagtatatt gctgaaactt tccttgaaga tgcccgtgaa gtgaacaacg   1140
ttcgcggtat gctgggcttc accggtactt acaaaggccg caaaatttcc gtaatgggtc   1200
acggtatggg tatcccgtcc tgctccatct acaccaaaga actgatcacc gatttcggcg   1260
tgaagaaaat tatccgcgtg ggttcctgtg gcgcagttct gccgcacgta aaactgcgcg   1320
acgtcgttat cggtatgggt gcctgcaccg attccaaagt taaccgcatc cgttttaaag   1380
accatgactt tgccgctatc gctgacttcg acatggtgcg taacgcagta gatgcagcta   1440
aagcactggg tattgatgct cgcgtgggta acctgttctc cgctgacctg ttctactctc   1500
cggacggcga aatgttcgac gtgatggaaa aatacggcat tctcggcgtg gaaatggaag   1560
cggctggtat ctacggcgtc gctgcagaat ttggcgcgaa agccctgacc atctgcaccg   1620
tatctgacca catccgcact cacgagcaga ccactgccgc tgagcgtcag actaccttca   1680
acgacatgat caaaatcgca ctggaatccg ttctgctggg cgataaagag taagtcgacc   1740
tgcaggcatg caagctttat gcttgtaaac cgttttgtga aaaaattttt aaaataaaaa   1800
aggggacctc tagggtcccc aattaattag taatataatc tattaaaggt cattcaaaag   1860
gtcatccacc ggatcagctt agtaaagccc tcgctagatt ttaatgcgga tgttgcgatt   1920
acttcgccaa ctattgcgat aacaagaaaa agccagcctt tcatgatata tctcccaatt   1980
tgtgtagggc ttattatgca cgcttaaaaa taataaaagc agacttgacc tgatagtttg   2040
gctgtgagca attatgtgct tagtgcatct aacgcttgag ttaagccgcg ccgcgaagcg   2100
gcgtcggctt gaacgaattg ttagacatta tttgccgact accttggtga tctcgccttt   2160
cacgtagtgg acaaattctt ccaactgatc tgcgcgccga gatgcgccgc gtgcggctgc   2220
tggagatggc ggacgcgatg gatatgttct gccaagggtt ggtttgcgca ttcacagttc   2280
tccgcaagaa ttgattggct ccaattcttg gagtggtgaa tccgttagcg aggtgccgcc   2340
ggcttccatt caggtcgagg tggcccggct ccatgcaccg cgacgcaacg cggggaggca   2400
gacaaggtat agggcggcgc ctacaatcca tgccaacccg ttccatgtgc tcgccgaggc   2460
ggcataaatc gccgtgacga tcagcggtcc agtgatcgaa gttaggctgg taagagccgc   2520
gagcgatcct tgaagctgtc cctgatggtc gtcatctacc tgcctggaca gcatggcctg   2580
caacgcgggc atcccgatgc cgccggaagc gagaagaatc ataatgggga aggccatcca   2640
gcctcgcgtc gcgaacgcca gcaagacgta gcccagcgcg tcggccgcca tgccggcgat   2700
aatggcctgc ttctcgccga aacgtttggt ggcgggacca gtgacgaagg cttgagcgag   2760
ggcgtgcaag attccgaata ccgcaagcga caggccgatc atcgtcgcgc tccagcgaaa   2820
gcggtcctcg ccgaaaatga cccagagcgc tgccggcacc tgtcctacga gttgcatgat   2880
aaagaagaca gtcataagtg cggcgacgat agtcatgccc cgcgcccacc ggaaggagct   2940
gactgggttg aaggctctca agggcatcgg tcgacgctct cccttatgcg actcctgcat   3000
taggaagcag cccagtagta ggttgaggcc gttgagcacc gccgccgcaa ggaatggtgc   3060
```

-continued

```
atgcaaggag atggcgccca acagtccccc ggccacgggg cctgccacca tacccacgcc   3120
gaaacaagcg ctcatgagcc cgaagtggcg agcccgatct tccccatcgg tgatgtcggc   3180
gatataggcg ccagcaaccg cacctgtggc gccggtgatg ccggccacga tgcgtccggc   3240
gtagaggatc cacaggacgg gtgtggtcgc catgatcgcg tagtcgatag tggctccaag   3300
tagcgaagcg agcaggactg ggcggcggcc aaagcggtcg gacagtgctc cgagaacggg   3360
tgcgcataga aattgcatca acgcatatag cgctagcagc acgccatagt gactggcgat   3420
gctgtcggaa tggacgatat cccgcaagag gcccggcagt accggcataa ccaagcctat   3480
gcctacagca tccagggtga cggtgccgag gatgacgatg agcgcattgt tagatttcat   3540
acacggtgcc tgactgcgtt agcaatttaa ctgtgataaa ctaccgcatt aaagctcatg   3600
cggatcagtg agggtttgca actgcgggtc aaggatctgg atttcgatca cggcacgatc   3660
atcgtgcggg agggcaaggg ctccaaggat cgggccttga tgttacccga gagcttggca   3720
cccagcctgc gcgagcaggg gaattgatcc ggtggatgac cttttgaatg acctttaata   3780
gattatatta ctaattaatt ggggacccta gaggtcccct tttttatttt aaaaattttt   3840
tcacaaaacg gtttacaagc ataaagcttg gcactggccg tcgttttaca acgtcgtgac   3900
tgggaaaacc ctggcgttac ccaacttaat cgccttgcag cacatccccc tttcgccagc   3960
tggcgtaata gcgaagaggc ccgcaccgat cgcccttccc aacagttgcg cagcctgaat   4020
ggcgaatggc gcctgatgcg gtattttctc cttacgcatc tgtgcggtat ttcacaccgc   4080
atatggtgca ctctcagtac aatctgctct gatgccgcat agttaagcca gccccgacac   4140
ccgccaacac ccgctgacgc gccctgacgg gcttgtctgc tcccggcatc cgcttacaga   4200
caagctgtga ccgtctccgg gagctgcatg tgtcagaggt tttcaccgtc atcaccgaaa   4260
cgcgcgagac gaaagggcct cgtgatacgc ctatttttat aggttaatgt catgataata   4320
atggtttctt agacgtcagg tggcactttt cggggaaatg tgcgcggaac ccctatttgt   4380
ttatttttct aaatacattc aaatatgtat ccgctcatga gacaataacc ctgataaatg   4440
cttcaataat attgaaaaag gaagagtatg agtattcaac atttccgtgt cgcccttatt   4500
cccttttttg cggcattttg ccttcctgtt tttgctcacc cagaaacgct ggtgaaagta   4560
aaagatgctg aagatcagtt gggtgcacga gtgggttaca tcgaactgga tctcaacagc   4620
ggtaagatcc ttgagagttt tcgccccgaa gaacgttttc caatgatgag cacttttaaa   4680
gttctgctat gtggcgcggt attatcccgt attgacgccg ggcaagagca actcggtcgc   4740
cgcatacact attctcagaa tgacttggtt gagtactcac cagtcacaga aaagcatctt   4800
acggatggca tgacagtaag agaattatgc agtgctgcca taaccatgag tgataacact   4860
gcggccaact tacttctgac aacgatcgga ggaccgaagg agctaaccgc ttttttgcac   4920
aacatggggg atcatgtaac tcgccttgat cgttgggaac cggagctgaa tgaagccata   4980
ccaaacgacg agcgtgacac cacgatgcct gtagcaatgg caacaacgtt gcgcaaacta   5040
ttaactggcg aactacttac tctagcttcc cggcaacaat taatagactg gatggaggcg   5100
gataaagttg caggaccact tctgcgctcg gcccttccgg ctggctggtt tattgctgat   5160
aaatctggag ccggtgagcg tgggtctcgc ggtatcattg cagcactggg gccagatggt   5220
aagccctccc gtatcgtagt tatctacacg acggggagtc aggcaactat ggatgaacga   5280
aatagacaga tcgctgagat aggtgcctca ctgattaagc attggtaact gtcagaccaa   5340
gtttactcat atatacttta gattgattta aaacttcatt tttaatttaa aaggatctag   5400
gtgaagatcc tttttgataa tctcatgacc aaaatccctt aacgtgagtt ttcgttccac   5460
```

-continued

```
tgagcgtcag accccgtaga aaagatcaaa ggatcttctt gagatccttt ttttctgcgc   5520

gtaatctgct gcttgcaaac aaaaaaacca ccgctaccag cggtggtttg tttgccggat   5580

caagagctac caactctttt tccgaaggta actggcttca gcagagcgca gataccaaat   5640

actgtccttc tagtgtagcc gtagttaggc caccacttca agaactctgt agcaccgcct   5700

acatacctcg ctctgctaat cctgttacca gtggctgctg ccagtggcga taagtcgtgt   5760

cttaccgggt tggactcaag acgatagtta ccggataagg cgcagcggtc gggctgaacg   5820

gggggttcgt gcacacagcc cagcttggag cgaacgacct acaccgaact gagataccta   5880

cagcgtgagc tatgagaaag cgccacgctt cccgaaggga gaaaggcgga caggtatccg   5940

gtaagcggca gggtcggaac aggagagcgc acgagggagc ttccaggggg aaacgcctgg   6000

tatctttata gtcctgtcgg gtttcgccac ctctgacttg agcgtcgatt tttgtgatgc   6060

tcgtcagggg ggcggagcct atggaaaaac gccagcaacg cggccttttt acggttcctg   6120

gccttttgct ggccttttgc tcacatgttc tttcctgcgt tatcccctga ttctgtggat   6180

aaccgtatta ccgcctttga gtgagctgat accgctcgcc gcagccgaac gaccgagcgc   6240

agcgagtcag tgagcgagga agcggaaga                                      6269
```

<210> SEQ ID NO 10
<211> LENGTH: 6299
<212> TYPE: DNA
<213> ORGANISM: Artificial Sequence
<220> FEATURE:
<223> OTHER INFORMATION: udp and deoD cloned in pUC18 so to create a fusion between the two proteins bonded to each other via an aa linker

<400> SEQUENCE: 10

```
gcgcccaata cgcaaaccgc ctctccccgc gcgttggccg attcattaat gcagctggca     60

cgacaggttt cccgactgga aagcgggcag tgagcgcaac gcaattaatg tgagttagct    120

cactcattag gcaccccagg ctttacactt tatgcttccg gctcgtatgt tgtgtggaat    180

tgtgagcgga taacaatttc acacaggaaa cagctatgac catgattacg aattcgagct    240

cggtaccatc catgtccaag tctgatgttt ttcatctcgg cctcactaaa aacgatttac    300

aaggggctac gcttgccatc gtccctggcg acccggatcg tgtggaaaag atcgccgcgc    360

tgatggataa gccggttaag ctggcatctc accgcgaatt cactacctgg cgtgcagagc    420

tggatggtaa acctgttatc gtctgctcta ccggtatcgg cggcccgtct acctctattg    480

ctgttgaaga gctggcacag ctgggcattc gcaccttcct gcgtatcggt acaacgggcg    540

ctattcagcc gcatattaat gtgggtgatg tcctggttac cacggcgtct gtccgtctgg    600

atggcgcgag cctgcacttc gcaccgctgg aattcccggc tgtcgctgat ttcgaatgta    660

cgactgcgct ggttgaagct gcgaaatcca ttggcgcgac aactcacgtt ggcgtgacag    720

cttcttctga taccttctac ccaggtcagg aacgttacga tacttactct ggtcgcgtag    780

ttcgtcactt taaaggttct atggaagagt ggcaggcgat gggcgtaatg aactatgaaa    840

tggaatctgc aaccctgctg accatgtgtg caagtcaggg cctgcgtgcc ggtatggtag    900

cgggtgttat cgttaaccgc acccagcaag agatcccgaa tgctgagacg atgaaacaaa    960

ccgaaagcca tgcggtgaaa atcgtggtgg aagcggcgcg tcgtctgctg tccatgggcg   1020

gtggcagccc gggcattctg gccatggcta ccccacacat taatgcagaa atgggcgatt   1080

tcgctgacgt agttttgatg ccaggcgacc cgctgcgtgc gaagtatatt gctgaaactt   1140

tccttgaaga tgcccgtgaa gtgaacaacg ttcgcggtat gctgggcttc accggtactt   1200
```

-continued

```
acaaaggccg caaaatttcc gtaatgggtc acggtatggg tatcccgtcc tgctccatct   1260
acaccaaaga actgatcacc gatttcggcg tgaagaaaat tatccgcgtg ggttcctgtg   1320
gcgcagttct gccgcacgta aaactgcgcg acgtcgttat cggtatgggt gcctgcaccg   1380
attccaaagt taaccgcatc cgttttaaag accatgactt tgccgctatc gctgacttcg   1440
acatggtgcg taacgcagta gatgcagcta aagcactggg tattgatgct cgcgtgggta   1500
acctgttctc cgctgacctg ttctactctc cggacggcga aatgttcgac gtgatggaaa   1560
aatacggcat tctcggcgtg gaaatggaag cggctggtat ctacggcgtc gctgcagaat   1620
ttggcgcgaa agccctgacc atctgcaccg tatctgacca catccgcact cacgagcaga   1680
ccactgccgc tgagcgtcag actaccttca acgacatgat caaaatcgca ctggaatccg   1740
ttctgctggg cgataaagag taagtcgacc tgcaggcatg caagctttat gcttgtaaac   1800
cgttttgtga aaaaattttt aaaataaaaa aggggacctc tagggtcccc aattaattag   1860
taatataatc tattaaaggt cattcaaaag gtcatccacc ggatcagctt agtaaagccc   1920
tcgctagatt ttaatgcgga tgttgcgatt acttcgccaa ctattgcgat aacaagaaaa   1980
agccagcctt tcatgatata tctcccaatt tgtgtagggc ttattatgca cgcttaaaaa   2040
taataaaagc agacttgacc tgatagtttg gctgtgagca attatgtgct tagtgcatct   2100
aacgcttgag ttaagccgcg ccgcgaagcg gcgtcggctt gaacgaattg ttagacatta   2160
tttgccgact accttggtga tctcgccttt cacgtagtgg acaaattctt ccaactgatc   2220
tgcgcgccga gatgcgccgc gtgcggctgc tggagatggc ggacgcgatg gatatgttct   2280
gccaagggtt ggtttgcgca ttcacagttc tccgcaagaa ttgattggct ccaattcttg   2340
gagtggtgaa tccgttagcg aggtgccgcc ggcttccatt caggtcgagg tggcccggct   2400
ccatgcaccg cgacgcaacg cggggaggca gacaaggtat agggcggcgc ctacaatcca   2460
tgccaacccg ttccatgtgc tcgccgaggc ggcataaatc gccgtgacga tcagcggtcc   2520
agtgatcgaa gttaggctgg taagagccgc gagcgatcct tgaagctgtc cctgatggtc   2580
gtcatctacc tgcctggaca gcatggcctg caacgcgggc atcccgatgc cgccggaagc   2640
gagaagaatc ataatgggga aggccatcca gcctcgcgtc gcgaacgcca gcaagacgta   2700
gcccagcgcg tcggccgcca tgccggcgat aatggcctgc ttctcgccga aacgtttggt   2760
ggcgggacca gtgacgaagg cttgagcgag ggcgtgcaag attccgaata ccgcaagcga   2820
caggccgatc atcgtcgcgc tccagcgaaa gcggtcctcg ccgaaaatga cccagagcgc   2880
tgccggcacc tgtcctacga gttgcatgat aaagaagaca gtcataagtg cggcgacgat   2940
agtcatgccc cgcgcccacc ggaaggagct gactgggttg aaggctctca agggcatcgg   3000
tcgacgctct cccttatgcg actcctgcat taggaagcag cccagtagta ggttgaggcc   3060
gttgagcacc gccgccgcaa ggaatggtgc atgcaaggag atggcgccca acagtccccc   3120
ggccacgggg cctgccacca tacccacgcc gaaacaagcg ctcatgagcc cgaagtggcg   3180
agcccgatct tccccatcgg tgatgtcggc gatataggcg ccagcaaccg cacctgtggc   3240
gccggtgatg ccggccacga tgcgtccggc gtagaggatc cacaggacgg gtgtggtcgc   3300
catgatcgcg tagtcgatag tggctccaag tagcgaagcg agcaggactg ggcggcggcc   3360
aaagcggtcg gacagtgctc cgagaacggg tgcgcataga aattgcatca acgcatatag   3420
cgctagcagc acgccatagt gactggcgat gctgtcggaa tggacgatat cccgcaagag   3480
gcccggcagt accggcataa ccaagcctat gcctacagca tccagggtga cggtgccgag   3540
gatgacgatg agcgcattgt tagatttcat acacggtgcc tgactgcgtt agcaatttaa   3600
```

-continued

```
ctgtgataaa ctaccgcatt aaagctcatg cggatcagtg agggtttgca actgcgggtc   3660
aaggatctgg atttcgatca cggcacgatc atcgtgcggg agggcaaggg ctccaaggat   3720
cgggccttga tgttacccga gagcttggca cccagcctgc gcgagcaggg gaattgatcc   3780
ggtggatgac cttttgaatg acctttaata gattatatta ctaattaatt ggggacccta   3840
gaggtcccct tttttatttt aaaaattttt tcacaaaacg gtttacaagc ataaagcttg   3900
gcactggccg tcgttttaca acgtcgtgac tgggaaaacc ctggcgttac ccaacttaat   3960
cgccttgcag cacatccccc tttcgccagc tggcgtaata gcgaagaggc ccgcaccgat   4020
cgcccttccc aacagttgcg cagcctgaat ggcgaatggc gcctgatgcg gtattttctc   4080
cttacgcatc tgtgcggtat ttcacaccgc atatggtgca ctctcagtac aatctgctct   4140
gatgccgcat agttaagcca gccccgacac ccgccaacac ccgctgacgc gccctgacgg   4200
gcttgtctgc tcccggcatc cgcttacaga caagctgtga ccgtctccgg gagctgcatg   4260
tgtcagaggt tttcaccgtc atcaccgaaa cgcgcgagac gaaagggcct cgtgatacgc   4320
ctatttttat aggttaatgt catgataata atggtttctt agacgtcagg tggcactttt   4380
cggggaaatg tgcgcggaac ccctatttgt ttatttttct aaatacattc aaatatgtat   4440
ccgctcatga gacaataacc ctgataaatg cttcaataat attgaaaaag gaagagtatg   4500
agtattcaac atttccgtgt cgcccttatt ccctttttttg cggcattttg ccttcctgtt   4560
tttgctcacc cagaaacgct ggtgaaagta aaagatgctg aagatcagtt gggtgcacga   4620
gtgggttaca tcgaactgga tctcaacagc ggtaagatcc ttgagagttt tcgccccgaa   4680
gaacgttttc caatgatgag cacttttaaa gttctgctat gtggcgcggt attatcccgt   4740
attgacgccg ggcaagagca actcggtcgc cgcatacact attctcagaa tgacttggtt   4800
gagtactcac cagtcacaga aaagcatctt acggatggca tgacagtaag agaattatgc   4860
agtgctgcca taaccatgag tgataacact gcggccaact tacttctgac aacgatcgga   4920
ggaccgaagg agctaaccgc ttttttgcac aacatggggg atcatgtaac tcgccttgat   4980
cgttgggaac cggagctgaa tgaagccata ccaaacgacg agcgtgacac cacgatgcct   5040
gtagcaatgg caacaacgtt gcgcaaacta ttaactggcg aactacttac tctagcttcc   5100
cggcaacaat taatagactg gatggaggcg gataaagttg caggaccact tctgcgctcg   5160
gcccttccgg ctggctggtt tattgctgat aaatctggag ccggtgagcg tgggtctcgc   5220
ggtatcattg cagcactggg gccagatggt aagccctccc gtatcgtagt tatctacacg   5280
acggggagtc aggcaactat ggatgaacga aatagacaga tcgctgagat aggtgcctca   5340
ctgattaagc attggtaact gtcagaccaa gtttactcat atatacttta gattgattta   5400
aaacttcatt tttaatttaa aaggatctag gtgaagatcc tttttgataa tctcatgacc   5460
aaaatccctt aacgtgagtt ttcgttccac tgagcgtcag accccgtaga aaagatcaaa   5520
ggatcttctt gagatccttt ttttctgcgc gtaatctgct gcttgcaaac aaaaaaacca   5580
ccgctaccag cggtggtttg tttgccggat caagagctac caactctttt tccgaaggta   5640
actggcttca gcagagcgca gataccaaat actgtccttc tagtgtagcc gtagttaggc   5700
caccacttca agaactctgt agcaccgcct acatacctcg ctctgctaat cctgttacca   5760
gtggctgctg ccagtggcga taagtcgtgt cttaccgggt tggactcaag acgatagtta   5820
ccggataagg cgcagcggtc gggctgaacg gggggttcgt gcacacagcc cagcttggag   5880
cgaacgacct acaccgaact gagataccta cagcgtgagc tatgagaaag cgccacgctt   5940
cccgaaggga gaaaggcgga caggtatccg gtaagcggca gggtcggaac aggagagcgc   6000
```

-continued acgagggagc ttccaggggg aaacgcctgg tatctttata gtcctgtcgg gtttcgccac 6060
ctctgacttg agcgtcgatt tttgtgatgc tcgtcagggg ggcggagcct atggaaaaac 6120
gccagcaacg cggccttttt acggttcctg gccttttgct ggccttttgc tcacatgttc 6180
tttcctgcgt tatcccctga ttctgtggat aaccgtatta ccgcctttga gtgagctgat 6240
accgctcgcc gcagccgaac gaccgagcgc agcgagtcag tgagcgagga agcggaaga 6299

<210> SEQ ID NO 11
<211> LENGTH: 2297
<212> TYPE: DNA
<213> ORGANISM: Artificial Sequence
<220> FEATURE:
<223> OTHER INFORMATION: cloning vector derived from pUC18

<400> SEQUENCE: 11
gcgcccaata cgcaaaccgc ctctccccgc gcgttggccg attcattaat gcagaattcg 60
agctcggtac ccggggatcc tctagagtcg acctgcaggc atgcaagctt atggtgcact 120
ctcagtacaa tctgctctga tgccgcatag ttaagccagc cccgacaccc gccaacaccc 180
gctgacgcgc cctgacgggc ttgtctgctc ccggcatccg cttacagaca agctgtgacc 240
gtctccggga gctgcatgtg tcagaggttt tcaccgtcat caccgaaacg cgcgagacga 300
aagggcctcg tgatacgcct atttttatag gttaatgtca tgataataat ggtttcttag 360
acgtcaggtg gcacttttcg gggaaatgtg cgcggaaccc ctatttgttt atttttctaa 420
atacattcaa atatgtatcc gctcatgaga caataaccct gataaatgct tcaataatat 480
tgaaaaagga agagtatgag tattcaacat ttccgtgtcg cccttattcc cttttttgcg 540
gcattttgcc ttcctgtttt tgctcaccca gaaacgctgg tgaaagtaaa agatgctgaa 600
gatcagttgg gtgcacgagt gggttacatc gaactggatc tcaacagcgg taagatcctt 660
gagagttttc gccccgaaga acgttttcca atgatgagca cttttaaagt tctgctatgt 720
ggcgcggtat tatcccgtat tgacgccggg caagagcaac tcggtcgccg catacactat 780
tctcagaatg acttggttga gtactcacca gtcacagaaa agcatcttac ggatggcatg 840
acagtaagag aattatgcag tgctgccata accatgagtg ataacactgc ggccaactta 900
cttctgacaa cgatcggagg accgaaggag ctaaccgctt ttttgcacaa catgggggat 960
catgtaactc gccttgatcg ttgggaaccg gagctgaatg aagccatacc aaacgacgag 1020
cgtgacacca cgatgcctgt agcaatggca acaacgttgc gcaaactatt aactggcgaa 1080
ctacttactc tagcttcccg gcaacaatta atagactgga tggaggcgga taaagttgca 1140
ggaccacttc tgcgctcggc ccttccggct ggctggttta ttgctgataa atctggagcc 1200
ggtgagcgtg ggtctcgcgg tatcattgca gcactggggc cagatggtaa gccctcccgt 1260
atcgtagtta tctacacgac ggggagtcag gcaactatgg atgaacgaaa tagacagatc 1320
gctgagatag gtgcctcact gattaagcat tggtaactgt cagaccaagt ttactcatat 1380
atactttaga ttgatttaaa acttcatttt taatttaaaa ggatctaggt gaagatcctt 1440
tttgataatc tcatgaccaa aatcccttaa cgtgagtttt cgttccactg agcgtcagac 1500
cccgtagaaa agatcaaagg atcttcttga gatccttttt ttctgcgcgt aatctgctgc 1560
ttgcaaacaa aaaaaccacc gctaccagcg gtggtttgtt tgccggatca agagctacca 1620
actctttttc cgaaggtaac tggcttcagc agagcgcaga taccaaatac tgtccttcta 1680
gtgtagccgt agttaggcca ccacttcaag aactctgtag caccgcctac atacctcgct 1740
ctgctaatcc tgttaccagt ggctgctgcc agtggcgata agtcgtgtct taccgggttg 1800

-continued

```
gactcaagac gatagttacc ggataaggcg cagcggtcgg gctgaacggg gggttcgtgc   1860

acacagccca gcttggagcg aacgacctac accgaactga gatacctaca gcgtgagcta   1920

tgagaaagcg ccacgcttcc cgaagggaga aaggcggaca ggtatccggt aagcggcagg   1980

gtcggaacag gagagcgcac gagggagctt ccagggggaa acgcctggta tctttatagt   2040

cctgtcgggt ttcgccacct ctgacttgag cgtcgatttt tgtgatgctc gtcagggggg   2100

cggagcctat ggaaaaacgc cagcaacgcg gcctttttac ggttcctggc cttttgctgg   2160

ccttttgctc acatgttctt tcctgcgtta tcccctgatt ctgtggataa ccgtattacc   2220

gcctttgagt gagctgatac cgctcgccgc agccgaacga ccgagcgcag cgagtcagtg   2280

agcgaggaag cggaaga                                                  2297
```

<210> SEQ ID NO 12
<211> LENGTH: 3031
<212> TYPE: DNA
<213> ORGANISM: Artificial Sequence
<220> FEATURE:
<223> OTHER INFORMATION: udp and deoD cloned into pGM746 without upstream ptac promoter

<400> SEQUENCE: 12

```
gcgcccaata cgcaaaccgc ctctccccgc gcgttggccg attcattaat gcagaattcg     60

agctcggtac ccggggatcc tagcaggagg gaattcttcc atggctaccc cacacattaa    120

tgcagaaatg ggcgatttcg ctgacgtagt tttgatgcca ggcgacccgc tgcgtgcgaa    180

gtatattgct gaaactttcc ttgaagatgc ccgtgaagtg aacaacgttc gcggtatgct    240

gggcttcacc ggtacttaca aaggccgcaa aatttccgta atgggtcacg gtatgggtat    300

cccgtcctgc tccatctaca ccaaagaact gatcaccgat ttcggcgtga agaaaattat    360

ccgcgtgggt tcctgtggcg cagttctgcc gcacgtaaaa ctgcgcgacg tcgttatcgg    420

tatgggtgcc tgcaccgatt ccaaagttaa ccgcatccgt tttaaagacc atgactttgc    480

cgctatcgct gacttcgaca tggtgcgtaa cgcagtagat gcagctaaag cactgggtat    540

tgatgctcgc gtgggtaacc tgttctccgc tgacctgttc tactctccgg acggcgaaat    600

gttcgacgtg atggaaaaat acggcattct cggcgtggaa atggaagcgg ctggtatcta    660

cggcgtcgct gcagaatttg gcgcgaaagc cctgaccatc tgcaccgtat ctgaccacat    720

ccgcactcac gagcagacca ctgccgctga gcgtcagact accttcaacg acatgatcaa    780

aatcgcactg gaatccgttc tgctgggcga taaagagtaa gtcgacctgc aggcatgcaa    840

gcttatggtg cactctcagt acaatctgct ctgatgccgc atagttaagc cagccccgac    900

acccgccaac acccgctgac gcgccctgac gggcttgtct gctcccggca tccgcttaca    960

gacaagctgt gaccgtctcc gggagctgca tgtgtcagag gttttcaccg tcatcaccga   1020

aacgcgcgag acgaaagggc ctcgtgatac gcctattttt ataggttaat gtcatgataa   1080

taatggtttc ttagacgtca ggtggcactt ttcggggaaa tgtgcgcgga acccctattt   1140

gtttattttt ctaaatacat tcaaatatgt atccgctcat gagacaataa ccctgataaa   1200

tgcttcaata atattgaaaa aggaagagta tgagtattca acatttccgt gtcgccctta   1260

ttcccttttt tgcggcattt tgccttcctg tttttgctca cccagaaacg ctggtgaaag   1320

taaaagatgc tgaagatcag ttgggtgcac gagtgggtta catcgaactg gatctcaaca   1380

gcggtaagat ccttgagagt tttcgccccg aagaacgttt tccaatgatg agcactttta   1440

aagttctgct atgtggcgcg gtattatccc gtattgacgc cgggcaagag caactcggtc   1500
```

-continued gccgcataca ctattctcag aatgacttgg ttgagtactc accagtcaca gaaaagcatc 1560
ttacggatgg catgacagta agagaattat gcagtgctgc cataaccatg agtgataaca 1620
ctgcggccaa cttacttctg acaacgatcg gaggaccgaa ggagctaacc gcttttttgc 1680
acaacatggg ggatcatgta actcgccttg atcgttggga accggagctg aatgaagcca 1740
taccaaacga cgagcgtgac accacgatgc ctgtagcaat ggcaacaacg ttgcgcaaac 1800
tattaactgg cgaactactt actctagctt cccggcaaca attaatagac tggatggagg 1860
cggataaagt tgcaggacca cttctgcgct cggcccttcc ggctggctgg tttattgctg 1920
ataaatctgg agccggtgag cgtgggtctc gcggtatcat tgcagcactg gggccagatg 1980
gtaagccctc ccgtatcgta gttatctaca cgacggggag tcaggcaact atggatgaac 2040
gaaatagaca gatcgctgag ataggtgcct cactgattaa gcattggtaa ctgtcagacc 2100
aagtttactc atatatactt tagattgatt taaaacttca tttttaattt aaaaggatct 2160
aggtgaagat cctttttgat aatctcatga ccaaaatccc ttaacgtgag ttttcgttcc 2220
actgagcgtc agaccccgta gaaaagatca aaggatcttc ttgagatcct ttttttctgc 2280
gcgtaatctg ctgcttgcaa acaaaaaaac caccgctacc agcggtggtt tgtttgccgg 2340
atcaagagct accaactctt tttccgaagg taactggctt cagcagagcg cagataccaa 2400
atactgtcct tctagtgtag ccgtagttag gccaccactt caagaactct gtagcaccgc 2460
ctacatacct cgctctgcta atcctgttac cagtggctgc tgccagtggc gataagtcgt 2520
gtcttaccgg gttggactca agacgatagt taccggataa ggcgcagcgg tcgggctgaa 2580
cggggggttc gtgcacacag cccagcttgg agcgaacgac ctacaccgaa ctgagatacc 2640
tacagcgtga gctatgagaa agcgccacgc ttcccgaagg gagaaaggcg gacaggtatc 2700
cggtaagcgg cagggtcgga acaggagagc gcacgaggga gcttccaggg ggaaacgcct 2760
ggtatcttta tagtcctgtc gggtttcgcc acctctgact tgagcgtcga tttttgtgat 2820
gctcgtcagg ggggcggagc ctatggaaaa acgccagcaa cgcggccttt ttacggttcc 2880
tggccttttg ctggcctttt gctcacatgt tctttcctgc gttatcccct gattctgtgg 2940
ataaccgtat taccgccttt gagtgagctg ataccgctcg ccgcagccga acgaccgagc 3000
gcagcgagtc agtgagcgag gaagcggaag a 3031

<210> SEQ ID NO 13
<211> LENGTH: 3128
<212> TYPE: DNA
<213> ORGANISM: Artificial Sequence
<220> FEATURE:
<223> OTHER INFORMATION: deoD cloned downstream ptac promoter

<400> SEQUENCE: 13
gcgcccaata cgcaaaccgc ctctccccgc gcgttggccg attcattaat gcagaattcg 60
agctccgaca tcataacggt tctggcaaat attctgaaat gagctgttga caattaatca 120
tcggctcgta taatgtgtgg aattgtgagc ggataacaat ttcacacagg aggatcctag 180
caggagggaa ttcttccatg gctaccccac acattaatgc agaaatgggc gatttcgctg 240
acgtagtttt gatgccaggc gacccgctgc gtgcgaagta tattgctgaa actttccttg 300
aagatgcccg tgaagtgaac aacgttcgcg gtatgctggg cttcaccggt acttacaaag 360
gccgcaaaat ttccgtaatg ggtcacggta tgggtatccc gtcctgctcc atctacacca 420
aagaactgat caccgatttc ggcgtgaaga aaattatccg cgtgggttcc tgtggcgcag 480
ttctgccgca cgtaaaactg cgcgacgtcg ttatcggtat gggtgcctgc accgattcca 540

-continued

```
aagttaaccg catccgtttt aaagaccatg actttgccgc tatcgctgac ttcgacatgg    600
tgcgtaacgc agtagatgca gctaaagcac tgggtattga tgctcgcgtg ggtaacctgt    660
tctccgctga cctgttctac tctccggacg gcgaaatgtt cgacgtgatg gaaaaatacg    720
gcattctcgg cgtggaaatg gaagcggctg gtatctacgg cgtcgctgca gaatttggcg    780
cgaaagccct gaccatctgc accgtatctg accacatccg cactcacgag cagaccactg    840
ccgctgagcg tcagactacc ttcaacgaca tgatcaaaat cgcactggaa tccgttctgc    900
tgggcgataa agagtaagtc gacctgcagg catgcaagct tatggtgcac tctcagtaca    960
atctgctctg atgccgcata gttaagccag ccccgacacc cgccaacacc cgctgacgcg   1020
ccctgacggg cttgtctgct cccggcatcc gcttacagac aagctgtgac cgtctccggg   1080
agctgcatgt gtcagaggtt ttcaccgtca tcaccgaaac gcgcgagacg aaagggcctc   1140
gtgatacgcc tatttttata ggttaatgtc atgataataa tggtttctta gacgtcaggt   1200
ggcacttttc ggggaaatgt gcgcggaacc cctatttgtt tatttttcta aatacattca   1260
aatatgtatc cgctcatgag acaataaccc tgataaatgc ttcaataata ttgaaaaagg   1320
aagagtatga gtattcaaca tttccgtgtc gcccttattc ccttttttgc ggcattttgc   1380
cttcctgttt ttgctcaccc agaaacgctg gtgaaagtaa aagatgctga agatcagttg   1440
ggtgcacgag tgggttacat cgaactggat ctcaacagcg gtaagatcct tgagagtttt   1500
cgccccgaag aacgttttcc aatgatgagc acttttaaag ttctgctatg tggcgcggta   1560
ttatcccgta ttgacgccgg gcaagagcaa ctcggtcgcc gcatacacta ttctcagaat   1620
gacttggttg agtactcacc agtcacagaa aagcatctta cggatggcat gacagtaaga   1680
gaattatgca gtgctgccat aaccatgagt gataacactg cggccaactt acttctgaca   1740
acgatcggag gaccgaagga gctaaccgct tttttgcaca acatggggga tcatgtaact   1800
cgccttgatc gttgggaacc ggagctgaat gaagccatac caaacgacga gcgtgacacc   1860
acgatgcctg tagcaatggc aacaacgttg cgcaaactat taactggcga actacttact   1920
ctagcttccc ggcaacaatt aatagactgg atggaggcgg ataaagttgc aggaccactt   1980
ctgcgctcgg cccttccggc tggctggttt attgctgata aatctggagc cggtgagcgt   2040
gggtctcgcg gtatcattgc agcactgggg ccagatggta agccctcccg tatcgtagtt   2100
atctacacga cggggagtca ggcaactatg gatgaacgaa atagacagat cgctgagata   2160
ggtgcctcac tgattaagca ttggtaactg tcagaccaag tttactcata tatactttag   2220
attgatttaa aacttcattt ttaatttaaa aggatctagg tgaagatcct ttttgataat   2280
ctcatgacca aaatccctta acgtgagttt tcgttccact gagcgtcaga ccccgtagaa   2340
aagatcaaag gatcttcttg agatcctttt tttctgcgcg taatctgctg cttgcaaaca   2400
aaaaaaccac cgctaccagc ggtggtttgt ttgccggatc aagagctacc aactcttttt   2460
ccgaaggtaa ctggcttcag cagagcgcag ataccaaata ctgtccttct agtgtagccg   2520
tagttaggcc accacttcaa gaactctgta gcaccgccta catacctcgc tctgctaatc   2580
ctgttaccag tggctgctgc cagtggcgat aagtcgtgtc ttaccgggtt ggactcaaga   2640
cgatagttac cggataaggc gcagcggtcg ggctgaacgg ggggttcgtg cacacagccc   2700
agcttggagc gaacgaccta caccgaactg agatacctac agcgtgagct atgagaaagc   2760
gccacgcttc ccgaagggag aaaggcggac aggtatccgg taagcggcag ggtcggaaca   2820
ggagagcgca cgagggagct tccaggggga aacgcctggt atctttatag tcctgtcggg   2880
tttcgccacc tctgacttga gcgtcgattt ttgtgatgct cgtcaggggg gcggagccta   2940
```

-continued

```
tggaaaaacg ccagcaacgc ggccttttta cggttcctgg ccttttgctg gccttttgct   3000

cacatgttct ttcctgcgtt atcccctgat tctgtggata accgtattac cgcctttgag   3060

tgagctgata ccgctcgccg cagccgaacg accgagcgca gcgagtcagt gagcgaggaa   3120

gcggaaga                                                            3128
```

<210> SEQ ID NO 14
<211> LENGTH: 3934
<212> TYPE: DNA
<213> ORGANISM: Artificial Sequence
<220> FEATURE:
<223> OTHER INFORMATION: udp and deoD cloned downstream ptac promoter

<400> SEQUENCE: 14

```
gcgcccaata cgcaaaccgc ctctccccgc gcgttggccg attcattaat gcagaattcg     60

agctccgaca tcataacggt tctggcaaat attctgaaat gagctgttga caattaatca    120

tcggctcgta taatgtgtgg aattgtgagc ggataacaat ttcacacagg aggatcctag    180

caggagggaa ttcttccatg gctaccccac acattaatgc agaaatgggc gatttcgctg    240

acgtagtttt gatgccaggc gacccgctgc gtgcgaagta tattgctgaa actttccttg    300

aagatgcccg tgaagtgaac aacgttcgcg gtatgctggg cttcaccggt acttacaaag    360

gccgcaaaat ttccgtaatg ggtcacggta tgggtatccc gtcctgctcc atctacacca    420

aagaactgat caccgatttc ggcgtgaaga aaattatccg cgtgggttcc tgtggcgcag    480

ttctgccgca cgtaaaactg cgcgacgtcg ttatcggtat gggtgcctgc accgattcca    540

aagttaaccg catccgtttt aaagaccatg actttgccgc tatcgctgac ttcgacatgg    600

tgcgtaacgc agtagatgca gctaaagcac tgggtattga tgctcgcgtg ggtaacctgt    660

tctccgctga cctgttctac tctccggacg gcgaaatgtt cgacgtgatg gaaaaatacg    720

gcattctcgg cgtggaaatg gaagcggctg gtatctacgg cgtcgctgca gaatttggcg    780

cgaaagccct gaccatctgc accgtatctg accacatccg cactcacgag cagaccactg    840

ccgctgagcg tcagactacc ttcaacgaca tgatcaaaat cgcactggaa tccgttctgc    900

tgggcgataa agagtaagtc gacacaggaa acagctatga ccatgattac gaattcgagc    960

tcggtaccat ccatgtccaa gtctgatgtt tttcatctcg gcctcactaa aaacgattta   1020

caaggggcta cgcttgccat cgtccctggc gacccggatc gtgtggaaaa gatcgccgcg   1080

ctgatggata agccggttaa gctggcatct caccgcgaat tcactacctg gcgtgcagag   1140

ctggatggta aacctgttat cgtctgctct accggtatcg gcggcccgtc tacctctatt   1200

gctgttgaag agctggcaca gctgggcatt cgcaccttcc tgcgtatcgg tacaacgggc   1260

gctattcagc cgcatattaa tgtgggtgat gtcctggtta ccacggcgtc tgtccgtctg   1320

gatggcgcga gcctgcactt cgcaccgctg gaattcccgg ctgtcgctga tttcgaatgt   1380

acgactgcgc tggttgaagc tgcgaaatcc attggcgcga caactcacgt tggcgtgaca   1440

gcttcttctg ataccttcta cccaggtcag gaacgttacg atacttactc tggtcgcgta   1500

gttcgtcact ttaaaggttc tatggaagag tggcaggcga tgggcgtaat gaactatgaa   1560

atggaatctg caaccctgct gaccatgtgt gcaagtcagg gcctgcgtgc cggtatggta   1620

gcgggtgtta tcgttaaccg cacccagcaa gagatcccga atgctgagac gatgaaacaa   1680

accgaaagcc atgcggtgaa aatcgtggtg gaagcggcgc gtcgtctgct gtaattctct   1740

taagcttatg gtgcactctc agtacaatct gctctgatgc cgcatagtta agccagcccc   1800

gacacccgcc aacacccgct gacgcgccct gacgggcttg tctgctcccg gcatccgctt   1860
```

-continued

```
acagacaagc tgtgaccgtc tccgggagct gcatgtgtca gaggttttca ccgtcatcac   1920

cgaaacgcgc gagacgaaag ggcctcgtga tacgcctatt tttataggtt aatgtcatga   1980

taataatggt ttcttagacg tcaggtggca cttttcgggg aaatgtgcgc ggaaccccta   2040

tttgtttatt tttctaaata cattcaaata tgtatccgct catgagacaa taaccctgat   2100

aaatgcttca ataatattga aaaaggaaga gtatgagtat tcaacatttc cgtgtcgccc   2160

ttattccctt ttttgcggca ttttgccttc ctgtttttgc tcacccagaa acgctggtga   2220

aagtaaaaga tgctgaagat cagttgggtg cacgagtggg ttacatcgaa ctggatctca   2280

acagcggtaa gatccttgag agttttcgcc ccgaagaacg ttttccaatg atgagcactt   2340

ttaaagttct gctatgtggc gcggtattat cccgtattga cgccgggcaa gagcaactcg   2400

gtcgccgcat acactattct cagaatgact tggttgagta ctcaccagtc acagaaaagc   2460

atcttacgga tggcatgaca gtaagagaat tatgcagtgc tgccataacc atgagtgata   2520

acactgcggc caacttactt ctgacaacga tcggaggacc gaaggagcta accgcttttt   2580

tgcacaacat gggggatcat gtaactcgcc ttgatcgttg ggaaccggag ctgaatgaag   2640

ccataccaaa cgacgagcgt gacaccacga tgcctgtagc aatggcaaca acgttgcgca   2700

aactattaac tggcgaacta cttactctag cttcccggca acaattaata gactggatgg   2760

aggcggataa agttgcagga ccacttctgc gctcggccct tccggctggc tggtttattg   2820

ctgataaatc tggagccggt gagcgtgggt ctcgcggtat cattgcagca ctggggccag   2880

atggtaagcc ctcccgtatc gtagttatct acacgacggg gagtcaggca actatggatg   2940

aacgaaatag acagatcgct gagataggtg cctcactgat taagcattgg taactgtcag   3000

accaagttta ctcatatata ctttagattg atttaaaact tcatttttaa tttaaaagga   3060

tctaggtgaa gatccttttt gataatctca tgaccaaaat cccttaacgt gagttttcgt   3120

tccactgagc gtcagacccc gtagaaaaga tcaaaggatc ttcttgagat cctttttttc   3180

tgcgcgtaat ctgctgcttg caaacaaaaa aaccaccgct accagcggtg gtttgtttgc   3240

cggatcaaga gctaccaact ctttttccga aggtaactgg cttcagcaga gcgcagatac   3300

caaatactgt ccttctagtg tagccgtagt taggccacca cttcaagaac tctgtagcac   3360

cgcctacata cctcgctctg ctaatcctgt taccagtggc tgctgccagt ggcgataagt   3420

cgtgtcttac cgggttggac tcaagacgat agttaccgga taaggcgcag cggtcgggct   3480

gaacgggggg ttcgtgcaca cagcccagct tggagcgaac gacctacacc gaactgagat   3540

acctacagcg tgagctatga gaaagcgcca cgcttcccga agggagaaag gcggacaggt   3600

atccggtaag cggcagggtc ggaacaggag agcgcacgag ggagcttcca gggggaaacg   3660

cctggtatct ttatagtcct gtcgggtttc gccacctctg acttgagcgt cgatttttgt   3720

gatgctcgtc aggggggcgg agcctatgga aaaacgccag caacgcggcc tttttacggt   3780

tcctggcctt ttgctggcct tttgctcaca tgttctttcc tgcgttatcc cctgattctg   3840

tggataaccg tattaccgcc tttgagtgag ctgataccgc tcgccgcagc cgaacgaccg   3900

agcgcagcga gtcagtgagc gaggaagcgg aaga                               3934
```

<210> SEQ ID NO 15
<211> LENGTH: 6046
<212> TYPE: DNA
<213> ORGANISM: Artificial Sequence
<220> FEATURE:
<223> OTHER INFORMATION: udp and deoD cloned downstream ptac promoter -continued

<400> SEQUENCE: 15

```
gcgcccaata cgcaaaccgc ctctccccgc gcgttggccg attcattaat gcagaattcg     60
agctccgaca tcataacggt tctggcaaat attctgaaat gagctgttga caattaatca    120
tcggctcgta taatgtgtgg aattgtgagc ggataacaat ttcacacagg aggatcctag    180
caggagggaa ttcttccatg gctaccccac acattaatgc agaaatgggc gatttcgctg    240
acgtagtttt gatgccaggc gacccgctgc gtgcgaagta tattgctgaa actttccttg    300
aagatgcccg tgaagtgaac aacgttcgcg gtatgctggg cttcaccggt acttacaaag    360
gccgcaaaat ttccgtaatg ggtcacggta tgggtatccc gtcctgctcc atctacacca    420
aagaactgat caccgatttc ggcgtgaaga aaattatccg cgtgggttcc tgtggcgcag    480
ttctgccgca cgtaaaactg cgcgacgtcg ttatcggtat gggtgcctgc accgattcca    540
aagttaaccg catccgtttt aaagaccatg actttgccgc tatcgctgac ttcgacatgg    600
tgcgtaacgc agtagatgca gctaaagcac tgggtattga tgctcgcgtg ggtaacctgt    660
tctccgctga cctgttctac tctccggacg gcgaaatgtt cgacgtgatg gaaaaatacg    720
gcattctcgg cgtggaaatg gaagcggctg gtatctacgg cgtcgctgca gaatttggcg    780
cgaaagccct gaccatctgc accgtatctg accacatccg cactcacgag cagaccactg    840
ccgctgagcg tcagactacc ttcaacgaca tgatcaaaat cgcactggaa tccgttctgc    900
tgggcgataa agagtaagtc gacacaggaa acagctatga ccatgattac gaattcgagc    960
tcggtaccat ccatgtccaa gtctgatgtt tttcatctcg gcctcactaa aaacgattta   1020
caaggggcta cgcttgccat cgtccctggc gacccggatc gtgtggaaaa gatcgccgcg   1080
ctgatggata agccggttaa gctggcatct caccgcgaat tcactacctg gcgtgcagag   1140
ctggatggta aacctgttat cgtctgctct accggtatcg gcggcccgtc tacctctatt   1200
gctgttgaag agctggcaca gctgggcatt cgcaccttcc tgcgtatcgg tacaacgggc   1260
gctattcagc cgcatattaa tgtgggtgat gtcctggtta ccacggcgtc tgtccgtctg   1320
gatggcgcga gcctgcactt cgcaccgctg gaattcccgg ctgtcgctga tttcgaatgt   1380
acgactgcgc tggttgaagc tgcgaaatcc attggcgcga caactcacgt tggcgtgaca   1440
gcttcttctg ataccttcta cccaggtcag gaacgttacg atacttactc tggtcgcgta   1500
gttcgtcact ttaaaggttc tatggaagag tggcaggcga tgggcgtaat gaactatgaa   1560
atggaatctg caaccctgct gaccatgtgt gcaagtcagg gcctgcgtgc cggtatggta   1620
gcgggtgtta tcgttaaccg cacccagcaa gagatcccga atgctgagac gatgaaacaa   1680
accgaaagcc atgcggtgaa aatcgtggtg gaagcggcgc gtcgtctgct gtaattctct   1740
taagctttat gcttgtaaac cgttttgtga aaaaattttt aaaataaaaa aggggacctc   1800
tagggtcccc aattaattag taatataatc tattaaaggt cattcaaaag gtcatccacc   1860
ggatcagctt agtaaagccc tcgctagatt ttaatgcgga tgttgcgatt acttcgccaa   1920
ctattgcgat aacaagaaaa agccagcctt tcatgatata tctcccaatt tgtgtagggc   1980
ttattatgca cgcttaaaaa taataaaagc agacttgacc tgatagtttg gctgtgagca   2040
attatgtgct tagtgcatct aacgcttgag ttaagccgcg ccgcgaagcg gcgtcggctt   2100
gaacgaattg ttagacatta tttgccgact accttggtga tctcgccttt cacgtagtgg   2160
acaaattctt ccaactgatc tgcgcgccga gatgcgccgc gtgcggctgc tggagatggc   2220
ggacgcgatg gatatgttct gccaagggtt ggtttgcgca ttcacagttc tccgcaagaa   2280
ttgattggct ccaattcttg gagtggtgaa tccgttagcg aggtgccgcc ggcttccatt   2340
```

-continued

```
caggtcgagg tggcccggct ccatgcaccg cgacgcaacg cggggaggca gacaaggtat   2400
agggcggcgc ctacaatcca tgccaacccg ttccatgtgc tcgccgaggc ggcataaatc   2460
gccgtgacga tcagcggtcc agtgatcgaa gttaggctgg taagagccgc gagcgatcct   2520
tgaagctgtc cctgatggtc gtcatctacc tgcctggaca gcatggcctg caacgcgggc   2580
atcccgatgc cgccggaagc gagaagaatc ataatgggga aggccatcca gcctcgcgtc   2640
gcgaacgcca gcaagacgta gcccagcgcg tcggccgcca tgccggcgat aatggcctgc   2700
ttctcgccga aacgtttggt ggcgggacca gtgacgaagg cttgagcgag ggcgtgcaag   2760
attccgaata ccgcaagcga caggccgatc atcgtcgcgc tccagcgaaa gcggtcctcg   2820
ccgaaaatga cccagagcgc tgccggcacc tgtcctacga gttgcatgat aaagaagaca   2880
gtcataagtg cggcgacgat agtcatgccc cgcgcccacc ggaaggagct gactgggttg   2940
aaggctctca agggcatcgg tcgacgctct ccccttatgcg actcctgcat taggaagcag   3000
cccagtagta ggttgaggcc gttgagcacc gccgccgcaa ggaatggtgc atgcaaggag   3060
atggcgccca acagtccccc ggccacgggg cctgccacca tacccacgcc gaaacaagcg   3120
ctcatgagcc cgaagtggcg agcccgatct tccccatcgg tgatgtcggc gatataggcg   3180
ccagcaaccg cacctgtggc gccggtgatg ccggccacga tgcgtccggc gtagaggatc   3240
cacaggacgg gtgtggtcgc catgatcgcg tagtcgatag tggctccaag tagcgaagcg   3300
agcaggactg ggcggcggcc aaagcggtcg gacagtgctc cgagaacggg tgcgcataga   3360
aattgcatca acgcatatag cgctagcagc acgccatagt gactggcgat gctgtcggaa   3420
tggacgatat cccgcaagag gcccggcagt accggcataa ccaagcctat gcctacagca   3480
tccagggtga cggtgccgag gatgacgatg agcgcattgt tagatttcat acacggtgcc   3540
tgactgcgtt agcaatttaa ctgtgataaa ctaccgcatt aaagctcatg cggatcagtg   3600
agggtttgca actgcgggtc aaggatctgg atttcgatca cggcacgatc atcgtgcggg   3660
agggcaaggg ctccaaggat cgggccttga tgttacccga gagcttggca cccagcctgc   3720
gcgagcaggg gaattgatcc ggtggatgac cttttgaatg acctttaata gattatatta   3780
ctaattaatt ggggacccta gaggtcccct tttttatttt aaaaattttt tcacaaaacg   3840
gtttacaagc ataaagctta tggtgcactc tcagtacaat ctgctctgat gccgcatagt   3900
taagccagcc ccgacacccg ccaacacccg ctgacgcgcc ctgacgggct tgtctgctcc   3960
cggcatccgc ttacagacaa gctgtgaccg tctccgggag ctgcatgtgt cagaggtttt   4020
caccgtcatc accgaaacgc gcgagacgaa agggcctcgt gatacgccta tttttatagg   4080
ttaatgtcat gataataatg gtttcttaga cgtcaggtgg cacttttcgg ggaaatgtgc   4140
gcggaacccc tatttgttta tttttctaaa tacattcaaa tatgtatccg ctcatgagac   4200
aataaccctg ataaatgctt caataatatt gaaaaaggaa gagtatgagt attcaacatt   4260
tccgtgtcgc ccttattccc ttttttgcgg cattttgcct tcctgttttt gctcacccag   4320
aaacgctggt gaaagtaaaa gatgctgaag atcagttggg tgcacgagtg ggttacatcg   4380
aactggatct caacagcggt aagatccttg agagttttcg ccccgaagaa cgttttccaa   4440
tgatgagcac ttttaaagtt ctgctatgtg gcgcggtatt atcccgtatt gacgccgggc   4500
aagagcaact cggtcgccgc atacactatt ctcagaatga cttggttgag tactcaccag   4560
tcacagaaaa gcatcttacg gatggcatga cagtaagaga attatgcagt gctgccataa   4620
ccatgagtga taacactgcg gccaacttac ttctgacaac gatcggagga ccgaaggagc   4680
taaccgcttt tttgcacaac atgggggatc atgtaactcg ccttgatcgt tgggaaccgg   4740
```

-continued

```
agctgaatga agccatacca aacgacgagc gtgacaccac gatgcctgta gcaatggcaa   4800

caacgttgcg caaactatta actggcgaac tacttactct agcttcccgg caacaattaa   4860

tagactggat ggaggcggat aaagttgcag gaccacttct gcgctcggcc cttccggctg   4920

gctggtttat tgctgataaa tctggagccg gtgagcgtgg gtctcgcggt atcattgcag   4980

cactggggcc agatggtaag ccctcccgta tcgtagttat ctacacgacg gggagtcagg   5040

caactatgga tgaacgaaat agacagatcg ctgagatagg tgcctcactg attaagcatt   5100

ggtaactgtc agaccaagtt tactcatata tactttagat tgatttaaaa cttcattttt   5160

aatttaaaag gatctaggtg aagatccttt ttgataatct catgaccaaa atcccttaac   5220

gtgagttttc gttccactga gcgtcagacc ccgtagaaaa gatcaaagga tcttcttgag   5280

atcctttttt tctgcgcgta atctgctgct tgcaaacaaa aaaaccaccg ctaccagcgg   5340

tggtttgttt gccggatcaa gagctaccaa ctctttttcc gaaggtaact ggcttcagca   5400

gagcgcagat accaaatact gtccttctag tgtagccgta gttaggccac cacttcaaga   5460

actctgtagc accgcctaca tacctcgctc tgctaatcct gttaccagtg gctgctgcca   5520

gtggcgataa gtcgtgtctt accgggttgg actcaagacg atagttaccg gataaggcgc   5580

agcggtcggg ctgaacgggg ggttcgtgca cacagcccag cttggagcga acgacctaca   5640

ccgaactgag atacctacag cgtgagctat gagaaagcgc cacgcttccc gaagggagaa   5700

aggcggacag gtatccggta agcggcaggg tcggaacagg agagcgcacg agggagcttc   5760

caggggggaaa cgcctggtat ctttatagtc ctgtcgggtt tcgccacctc tgacttgagc   5820

gtcgattttt gtgatgctcg tcaggggggc ggagcctatg gaaaaacgcc agcaacgcgg   5880

cctttttacg gttcctggcc ttttgctggc cttttgctca catgttcttt cctgcgttat   5940

cccctgattc tgtggataac cgtattaccg cctttgagtg agctgatacc gctcgccgca   6000

gccgaacgac cgagcgcagc gagtcagtga gcgaggaagc ggaaga                  6046


<210> SEQ ID NO 16
<211> LENGTH: 40
<212> TYPE: DNA
<213> ORGANISM: Artificial Sequence
<220> FEATURE:
<223> OTHER INFORMATION: primer

<400> SEQUENCE: 16

atcggtacca tccatgtcca agtctgatgt ttttcatctc                           40


<210> SEQ ID NO 17
<211> LENGTH: 34
<212> TYPE: DNA
<213> ORGANISM: Artificial Sequence
<220> FEATURE:
<223> OTHER INFORMATION: primer

<400> SEQUENCE: 17

agacggtcga caagagaatt acagcagacg acgc                                 34


<210> SEQ ID NO 18
<211> LENGTH: 37
<212> TYPE: DNA
<213> ORGANISM: Artificial Sequence
<220> FEATURE:
<223> OTHER INFORMATION: primer
```

-continued

<400> SEQUENCE: 18
ctgaattctt ccatggctac cccacacatt aatgcag 37

<210> SEQ ID NO 19
<211> LENGTH: 36
<212> TYPE: DNA
<213> ORGANISM: Artificial Sequence
<220> FEATURE:
<223> OTHER INFORMATION: primer

<400> SEQUENCE: 19
tcatggtcga cttactcttt atcgcccagc agaacg 36

<210> SEQ ID NO 20
<211> LENGTH: 29
<212> TYPE: DNA
<213> ORGANISM: Artificial Sequence
<220> FEATURE:
<223> OTHER INFORMATION: primer

<400> SEQUENCE: 20
attgagctcg acatcataac ggttctggc 29

<210> SEQ ID NO 21
<211> LENGTH: 29
<212> TYPE: DNA
<213> ORGANISM: Artificial Sequence
<220> FEATURE:
<223> OTHER INFORMATION: primer

<400> SEQUENCE: 21
attggatcct gtgtgaaatt gttatccgc 29

<210> SEQ ID NO 22
<211> LENGTH: 27
<212> TYPE: DNA
<213> ORGANISM: Artificial Sequence
<220> FEATURE:
<223> OTHER INFORMATION: primer

<400> SEQUENCE: 22
tccagtcgac acaggaaaca gctatga 27

<210> SEQ ID NO 23
<211> LENGTH: 29
<212> TYPE: DNA
<213> ORGANISM: Artificial Sequence
<220> FEATURE:
<223> OTHER INFORMATION: primer

<400> SEQUENCE: 23
tacgaagctt aagagaatta cagcagacg 29

<210> SEQ ID NO 24
<211> LENGTH: 25
<212> TYPE: DNA
<213> ORGANISM: Artificial Sequence
<220> FEATURE:
<223> OTHER INFORMATION: primer

<400> SEQUENCE: 24
ggccgttaac cgcacccagc aagag 25

<210> SEQ ID NO 25
<211> LENGTH: 25

-continued

```
<212> TYPE: DNA
<213> ORGANISM: Artificial Sequence
<220> FEATURE:
<223> OTHER INFORMATION: primer

<400> SEQUENCE: 25

agccatggac agcagacgac gcgcc                                25


<210> SEQ ID NO 26
<211> LENGTH: 28
<212> TYPE: DNA
<213> ORGANISM: Artificial Sequence
<220> FEATURE:
<223> OTHER INFORMATION: primer

<400> SEQUENCE: 26

gctgtccatg gctaccccac acattaat                             28


<210> SEQ ID NO 27
<211> LENGTH: 27
<212> TYPE: DNA
<213> ORGANISM: Artificial Sequence
<220> FEATURE:
<223> OTHER INFORMATION: primer

<400> SEQUENCE: 27

ccgggttaac tttggaatcg gtgcagg                              27


<210> SEQ ID NO 28
<211> LENGTH: 34
<212> TYPE: DNA
<213> ORGANISM: Artificial Sequence
<220> FEATURE:
<223> OTHER INFORMATION: primer

<400> SEQUENCE: 28

catgggcggt ggcagcccgg gcattctggc catg                      34


<210> SEQ ID NO 29
<211> LENGTH: 11
<212> TYPE: PRT
<213> ORGANISM: Artificial Sequence
<220> FEATURE:
<223> OTHER INFORMATION: amino acid linker

<400> SEQUENCE: 29

Ser Met Gly Gly Gly Ser Pro Gly Ile Leu Ala
1               5                   10
```